United States Patent
Rathod et al.

(10) Patent No.: US 9,102,665 B2
(45) Date of Patent: Aug. 11, 2015

(54) CYSTEINYL LEUKOTRIENE ANTAGONISTS

(75) Inventors: Rajendrasinh Rathod, Baroda (IN);
Tushar Bhatt, Baroda (IN); Kiritkumar Joshi, Baroda (IN); Binaka Dole, Baroda (IN); Kadiyala V. S. N. Murty, Baroda (IN); Rajamannar Thennati, Gujarat (IN)

(73) Assignee: Sun Pharma Advanced Research Company Ltd. (IN)

( * ) Notice: Subject to any disclaimer, the term of this patent is extended or adjusted under 35 U.S.C. 154(b) by 0 days.

(21) Appl. No.: 14/234,961

(22) PCT Filed: Jul. 26, 2012

(86) PCT No.: PCT/IN2012/000521
§ 371 (c)(1),
(2), (4) Date: Jan. 24, 2014

(87) PCT Pub. No.: WO2013/051024
PCT Pub. Date: Apr. 11, 2013

(65) Prior Publication Data
US 2014/0155596 A1    Jun. 5, 2014

(30) Foreign Application Priority Data
Jul. 26, 2011   (IN) .................... 2109/MUM/2011

(51) Int. Cl.
| | | |
|---|---|---|
| *C07D 215/14* | (2006.01) | |
| *C07D 413/10* | (2006.01) | |
| *C07D 215/18* | (2006.01) | |
| *C07D 401/12* | (2006.01) | |
| *C07D 407/10* | (2006.01) | |
| *C07D 407/12* | (2006.01) | |
| *C07D 407/14* | (2006.01) | |
| *C07D 409/12* | (2006.01) | |
| *C07D 241/42* | (2006.01) | |
| *C07D 277/64* | (2006.01) | |
| *C07D 401/10* | (2006.01) | |
| *C07D 401/14* | (2006.01) | |
| *C07D 405/10* | (2006.01) | |

(52) U.S. Cl.
CPC ............ *C07D 413/10* (2013.01); *C07D 215/14* (2013.01); *C07D 215/18* (2013.01); *C07D 241/42* (2013.01); *C07D 277/64* (2013.01); *C07D 401/10* (2013.01); *C07D 401/12* (2013.01); *C07D 401/14* (2013.01); *C07D 405/10* (2013.01); *C07D 407/10* (2013.01); *C07D 407/12* (2013.01); *C07D 407/14* (2013.01); *C07D 409/12* (2013.01)

(58) Field of Classification Search
CPC .. A01B 12/006; C07D 215/14; C07D 215/18;
C07D 241/42; C07D 277/64; C07D 401/10;
C07D 401/12; C07D 401/14; C07D 405/10;
C07D 407/10; C07D 407/12; C07D 407/14;
C07D 413/10
USPC .......................................... 546/159; 514/312
See application file for complete search history.

(56) References Cited

U.S. PATENT DOCUMENTS

| | | | | |
|---|---|---|---|---|
| 5,104,882 | A | * | 4/1992 | Young et al. .................. 514/311 |
| 5,204,358 | A | * | 4/1993 | Young et al. .................. 514/314 |
| 5,565,473 | A | | 10/1996 | Belley et al. |
| 8,007,830 | B2 | | 8/2011 | Down |

FOREIGN PATENT DOCUMENTS

| | | |
|---|---|---|
| WO | WO-9012006 A1 | 10/1990 |
| WO | WO-9808820 A1 | 3/1998 |
| WO | WO-2006058545 A1 | 6/2006 |
| WO | WO-2010148209 A2 | 12/2010 |

OTHER PUBLICATIONS

"International Application Serial No. PCT/IN2012/000521, International Search Report mailed Apr. 3, 2013", 2 pgs.
Patani, George A, et al., "Bioisosterism:? A Rational Approach in Drug Design", Chem. Rev., 96(8), (1996), 3147-3176.

* cited by examiner

*Primary Examiner* — D M Seaman
(74) *Attorney, Agent, or Firm* — Schwegman Lundberg & Woessner, P.A.

(57) ABSTRACT

The present invention relates to novel cysteinyl leukotriene (specifically LTD4) antagonists, mainly to quinolin, quinoxaline or benz[c]thiazole derivatives represented by the general formula (I), or the pharmaceutically acceptable salt thereof, process of preparation thereof, and to the use of the compounds in the preparation of pharmaceutical compositions for the therapeutic treatment of disorders related to cysteinyl leukotriene, in mammals, more specially in humans.

formula (I)

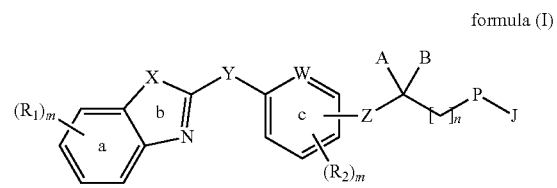

9 Claims, 1 Drawing Sheet

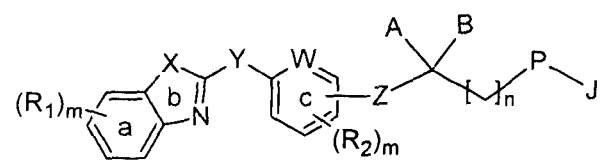
formula (I)

CYSTEINYL LEUKOTRIENE ANTAGONISTS

RELATED APPLICATIONS

This application is a U.S. National Stage filing under 35 U.S.C. 371 from International Patent Application Serial No. PCT/IN2012/000521, filed Jul. 26, 2012 and published on Apr. 11, 2013 as WO 2013 051024 A2, and republished as WO 2013 051024 A3, which claims the benefit of Indian Patent Application No. 2109/MUM/2011 filed on Jul. 26, 2011 which applications and publication are hereby incorporated by reference in their entirety.

FIELD OF INVENTION

The present invention relates to novel cysteinyl leukotriene (specifically LTD4) antagonists, mainly to quinolin, quinoxaline or benz[c]thiazole derivatives represented by the general formula (I) or the pharmaceutically acceptable salt thereof, process of preparation thereof, and to the use of the compounds in the preparation of pharmaceutical compositions for the therapeutic treatment of disorders related to cysteinyl leukotriene, in mammals, more specially in humans.

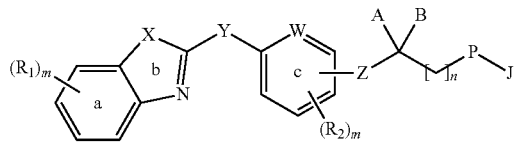

formula (I)

BACKGROUND OF THE INVENTION

The Cysteinyl Leukotriene metabolites such as LTC4, LTD4 and LTE4 are of membrane arachidonic acid origin, and are some of the known mediators (Dahlen et al., *Nature* 288, 484, 1980 and Burke et al., *J. Pharmacol. and Exp. Therap.*, 221, 235, 1983) of allergy and inflammatory born disorders such as allergic rhinitis, bronchial asthma, COPD, atopic dermatitis, urticaria, viral broncholitis, cystic fibrosis, eosinophilic gastro-enteritis, etc. CysLT1 and CysLT2 are the two receptors identified for which these mediators bind and the subsequent receptor mediated adverse responses lead to pathogenic conditions.

U.S. Pat. No. 5,856,322; U.S. Pat. No. 5,565,473; U.S. Pat. No. 5,266,568; U.S. Pat. No. 5,204,358; U.S. Pat. No. 5,104,882; U.S. Pat. No. 5,059,610; U.S. Pat. No. 5,051,427; U.S. Pat. No. 4,920,133; U.S. Pat. No. 4,920,132; EP 0315399; EP 0318093; EP 0399818; WO 1989/004303; WO 2004/043966; Chem. Rev., Article ASAP, DOI: 10.1021/cr100392s, Publication Date (Web): Apr. 28, 2011 etc discloses various leukotriene receptor antagonist.

Selective antagonists of CysLT1 receptor such as Montelukast (Singular; Merck: *Bioorg. Med. Chem. Lett.*, 1995, 5, 283 and *Progress in Medicinal chemistry* Vol 38, Chapter 5, Ed, by F. D. King and A. W. Oxford, 249, 2001), Zafirlukast (Accolate: AstraZeneca: *J. Med. Chem*, 1990, 33, 1781) and Pranlukast (Onon® Ono: *J. Med. Chem.*, 1988, 31, 84) have been commercialized for the treatment of seasonal allergic rhinitis, mild to moderate asthma therapy and are being evaluated for other inflammatory disorders. Since the marketed products have certain limitations for example Zafirlukast has liver microsomal binding leading to drug-drug interactions and Montelukast is being evaluated for the concern of suicidal tendencies in some subjects on prolonged use, there is a need for development of newer structures binding efficiently to the CysLT1 and showing the pharmacological activity with reduced side effect profile. Also there is a need for decreasing the steroid load on children and CysLT1 antagonists are known for their steroid sparing effect in the maintenance of Asthma.

SUMMARY OF THE INVENTION

The present invention relates to novel cysteinyl leukotriene (specifically LTD4) antagonists, mainly to quinolin, quinoxaline or benz[c]thiazole derivatives represented by the general formula (I),

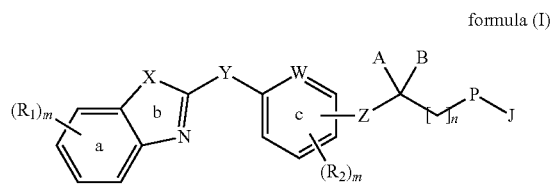

formula (I)

or the pharmaceutically acceptable salt thereof,
wherein,
ring 'a', ring 'b' and ring 'c' are independently an aryl or a heteroaryl ring optionally substituted by one or more identical or different radicals $R_1$ or $R_2$,
$R_1$ and $R_2$ are independently selected from the group consisting of hydrogen, halogen, —OH, —CN, —$NO_2$, —$NH_2$, —$C_{1-10}$-alkyl, —$C_{3-10}$ cycloalkyl, —O—$C_{1-8}$ alkyl (alkoxy), —O—$C_{3-8}$ cycloalkyl (cycloalkoxy), —S—$C_{1-8}$ alkyl (thioalkoxy), —C(O)—$C_{1-8}$ alkyl, —COOH, —C(O)$NH_2$, —C(O)NH—$C_{1-8}$ alkyl, —C(O)N($C_{1-8}$ alkyl)$_2$, —C(O)O—$C_{1-8}$ alkyl, —$C_{1-8}$ haloalkyl (haloalkoxy), —$C_{3-8}$ alkenyl, —$C_{3-8}$ alkynyl, —OC(O)—$NH_2$, —OC(O)—NH($C_{1-8}$ alkyl), —OC(O)—N($C_{1-8}$ alkyl)$_2$, —NH($C_{1-8}$ alkyl), —N($C_{1-8}$ alkyl)$_2$, —NH—$SO_2$—$C_{1-8}$ alkyl, —N($C_{1-8}$ alkyl)-$SO_2$—$C_{1-8}$ alkyl, —NH—C(O)—($C_{1-8}$ alkyl), —N($C_{1-8}$ alkyl)-C(O)—($C_{1-8}$ alkyl), —NH—C(O)O—$C_{1-8}$ alkyl, —N($C_{1-8}$ alkyl)-C(O)O—$C_{1-8}$ alkyl, —NH—C(O)—$NH_2$, —NH—C(O)—NH($C_{1-8}$ alkyl), —N($C_{1-8}$ alkyl)-C(O)—NH ($C_{1-8}$ alkyl), —N($C_{1-8}$ alkyl)-C(O)—N($C_{1-8}$ alkyl)$_2$, —NH—C(O)—NH—$SO_2$—$C_{1-8}$ alkyl, —N($C_{1-8}$ alkyl)-C(O)—$NHSO_2$—$C_{1-8}$ alkyl, —N($C_{1-8}$ alkyl)-C(O)—N($C_{1-8}$ alkyl)-$SO_2$—$C_{1-8}$ alkyl, —S—$C_{1-8}$ alkyl, —S(O)—$C_{1-8}$ alkyl, —$SO_2$—$C_{1-8}$ alkyl, —S-aryl, —S(O)-aryl, $SO_2$-aryl, —$SO_2NH_2$, —$SO_2$NH—($C_{1-8}$ alkyl), —$SO_2$N($C_{1-8}$ alkyl)$_2$;
W represents a group selected from —CH═ or —N═;
X represents a group selected from —CH═CH—, —S—, or —N═CH—;
Y represents a group selected from —CH═CH— or —C≡C—;
Z represents a bond or group selected from —(CH$_2$)$_n$—, —O—CH$_2$— or —CH═CH—;
A is a group selected from hydrogen, —OH, —OR, —SR, —O(CH$_2$)$_n$ aryl, —O(CH$_2$)$_n$ heteroaryl, —OCOR, —OCO-aryl, —SCOR, —SCO-aryl, —NRR', —NRCOR', NRCO-aryl, —NRCO-aryl-COOR, —NRCH$_2$ArCOOR, —NHCH$_2$(CR,R')OH, —NHCOCH$_2$ heteroaryl, —NHCOCH$_2$(CR,R')CH$_2$COOR, —NHCOCH$_2$(P)-aryl-COOR, —NHCOCH$_2$NRR', —NRSO$_2$R', —NRSO$_2$-aryl, —NR-CONRR', —NRCONR'-aryl, —NRCOCH$_2$-aryl-COOR', —NRPO(OR')(OH);

B is a group selected from hydrogen, —OR', —SR, —NRR' and —NRCOR';
or, A and B together can form a substituted or unsubstituted 5 to 8 membered cyclic ring containing at least two heteroatoms selected from oxygen and sulfur;
or, A and B together represent group consisting of C═O, C═S, C═N(OR) or C═NNRR';
P is selected from the group consisting of —O—, —S—, —CH$_2$— and —NR—; or P may form a —CH═CH— moiety with the adjacent carbon atom;
J represents a group selected from aryl-Q, heteroaryl-Q or —(CH$_2$)$_n$Q, wherein Q is a group selected from hydrogen, —CH$_3$, —CF$_3$, OR, —COOR, —CONRR', —CR═CR—COOR'; —OCH$_2$ aryl-COOR, —CH$_2$O-aryl-COOR, —CONHSO$_2$R, —CONHSO$_2$ aryl, —OCH$_2$CONRR', —NHSO$_2$R, —NHSO$_2$ aryl, —NHSO$_2$NHR, —SO$_2$NHR, —SO$_2$NH aryl, —NHCOR, —NHCO(CRR')—COOR, —C(RR')—COOR, tetrazole, —C(RR')OH, —C(RR')CONRR', —CH$_2$NRR' or —OCH$_2$C(RR')OH;
R and R' are independently selected from the group consisting of hydrogen, —C$_{1-6}$ alkyl, —C$_{3-6}$ cycloalkyl, —C$_{1-3}$ alkyl (cycloalkyl), —C$_{3-6}$ alkenyl and —C$_{3-6}$ alkynyl or, R and R' along with the atom to which they are attached, together can form a substituted or unsubstituted 5 to 8 membered cyclic ring;
'n' is an integer selected from 1, 2 or 3;
'm' is an integer selected from 0 to 4, both inclusive;
with the proviso that when P is —CH$_2$—, then A and B both represent groups connected to carbon through heteroatom and when B is hydrogen, then A is —NR—.

One aspect of the invention relates to compounds of general formula (Ia),

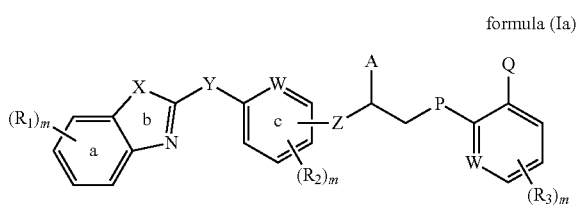

formula (Ia)

or the pharmaceutically acceptable salt thereof,
wherein,
$R_1$, $R_2$ and $R_3$ are independently selected from the group consisting of hydrogen, halogen, —OH, —CN, —NO$_2$, —NH$_2$, —C$_{1-10}$-alkyl, —C$_{3-10}$ cycloalkyl, —O—C$_{1-8}$ alkyl, —O—C$_{1-8}$ alkyl (alkoxy), —O—C$_{3-8}$ cycloalkyl (cycloalkoxy), —S—C$_{1-8}$ alkyl (thioalkoxy), —C(O)—C$_{1-8}$ alkyl, —COOH, —C(O)NH$_2$, —C(O)NH—C$_{1-8}$ alkyl, —C(O)N(C$_{1-8}$ alkyl)$_2$, —C(O)O—C$_{1-8}$ alkyl, —C$_{1-8}$ haloalkyl (haloalkoxy), —C$_{3-8}$ alkenyl, —C$_{3-8}$ alkynyl, —OC(O)—NH$_2$, —OC(O)—NH(C$_{1-8}$ alkyl), —OC(O)—N(C$_{1-8}$ alkyl)$_2$, —NH(C$_{1-8}$ alkyl), —N(C$_{1-8}$ alkyl)$_2$, —NH—SO$_2$—C$_{1-8}$ alkyl, —N(C$_{1-8}$ alkyl)-SO$_2$—C$_{1-8}$ alkyl, —NH—C(O)—(C$_{1-8}$ alkyl), —N(C$_{1-8}$ alkyl)-C(O)—(C$_{1-8}$ alkyl), —NH—C(O)O—C$_{1-8}$ alkyl, —N(C$_{1-8}$ alkyl)-C(O)O—C$_{1-8}$ alkyl, —NH—C(O)—NH$_2$, —NH—C(O)—NH(C$_{1-8}$ alkyl), —N(C$_{1-8}$ alkyl)-C(O)—NH(C$_{1-8}$ alkyl), —N(C$_{1-8}$ alkyl)-C(O)—N(C$_{1-8}$ alkyl)$_2$, —NH—C(O)—NH—SO$_2$—C$_{1-8}$ alkyl, —N(C$_{1-8}$ alkyl)-C(O)—NHSO$_2$—C$_{1-8}$ alkyl, —N(C$_{1-8}$ alkyl)-C(O)—N(C$_{1-8}$ alkyl)-SO$_2$—C$_{1-8}$ alkyl, —S—C$_{1-8}$ alkyl, —S(O)—C$_{1-8}$ alkyl, —SO$_2$—C$_{1-8}$ alkyl, —S-aryl, —S(O)-aryl, SO$_2$-aryl, —SO$_2$NH$_2$, —SO$_2$NH—(C$_{1-8}$ alkyl), —SO$_2$N(C$_{1-8}$ alkyl)$_2$;
W represents a group selected from —CH═ or —N═;

X represents a group selected from —CH═CH—, —S—, or —N═CH—;
Y represents a group selected from —CH═CH— or —C═C—;
A is a group selected from hydrogen, —OH, —OR, —SR, —O(CH$_2$)$_n$ aryl, —O(CH$_2$)$_n$ heteroaryl, —OCOR, —OCO-aryl, —SCOR, —SCO-aryl, —NRR', —NRCOR', —NRCO-aryl, to —NRCO-aryl-COOR, —NRCH$_2$ArCOOR, —NHCH$_2$(CR,R')OH, —NHCOCH$_2$ heteroaryl, —NH-COCH$_2$(CR,R')CH$_2$COOR, —NHCOCH$_2$(P)-aryl-COOR, —NHCOCH$_2$NRR', —NRSO$_2$R', —NRSO$_2$-aryl, —NR-CONRR', —NRCONR'-aryl, —NRCOCH$_2$-aryl-COOR', —NRPO(OR')(OH); with a proviso that when A is —OR or —SR, then is P is selected from —O—, —S— or —NR— and when A is —NR—, P is selected from —O—, —S—, —NR— or —CH$_2$—;
P is selected from the group consisting of —O—, —S—, —CH$_2$— and —NR—; or P may form a —CH═CH— moiety with the adjacent carbon atom;
Q is a group selected from hydrogen, —CH$_3$, —CF$_3$, OR, —COOR, —CONRR', —CR═CR—COOR'; —OCH$_2$ aryl-COOR, —CH$_2$O-aryl-COOR, —CONHSO$_2$R, —CONHSO$_2$ aryl, —OCH$_2$CONRR', —NHSO$_2$R, —NHSO$_2$ aryl, —NHSO$_2$NHR, —SO$_2$NHR, —SO$_2$NH aryl, —NHCOR, —NHCO(CRR')—COOR, —C(RR')—COOR, tetrazole, —C(RR')OH, —C(RR')CONRR', —CH$_2$NRR' or —OCH$_2$C(RR')OH;
R and R' are independently selected from the group consisting of hydrogen, —C$_{1-6}$ alkyl, —C$_{3-6}$ cycloalkyl, —C$_{1-3}$ alkyl (cycloalkyl), —C$_{3-6}$ alkenyl and —C$_{3-6}$ alkynyl or, R and R' along with the atom to which they are attached, together can form a substituted or unsubstituted 5 to 8 membered cyclic ring;
'm' is an integer selected from 0 to 4, both inclusive;
with the proviso that when P is —CH$_2$—, then A is —NR—.

In aspect of the invention relates to compounds of general formula (Ib),

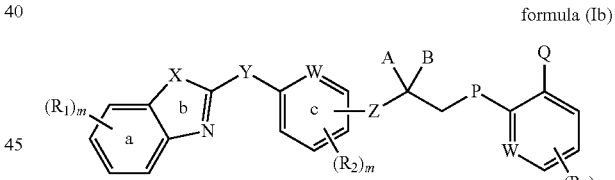

formula (Ib)

or the pharmaceutically acceptable salt thereof,
wherein,
$R_1$, $R_2$ and $R_3$ are independently selected from the group consisting of hydrogen, halogen, —OH, —CN, —NO$_2$, —NH$_2$, —C$_{1-10}$-alkyl, —C$_{3-10}$ cycloalkyl, —O—C$_{1-8}$ alkyl, —O—C$_{1-8}$ alkyl (alkoxy), —O—C$_{3-8}$ cycloalkyl (cycloalkoxy), —S—C$_{1-8}$ alkyl (thioalkoxy), —C(O)—C$_{1-8}$ alkyl, —COOH, —C(O)NH$_2$, —C(O)NH—C$_{1-8}$ alkyl, —C(O)N(C$_{1-8}$ alkyl)$_2$, —C(O)O—C$_{1-8}$ alkyl, —C$_{1-8}$ haloalkyl (haloalkoxy), —C$_{3-8}$ alkenyl, —C$_{3-8}$ alkynyl, —OC(O)—NH$_2$, —OC(O)—NH(C$_{1-8}$ alkyl), —OC(O)—N(C$_{1-8}$ alkyl)$_2$, —NH(C$_{1-8}$ alkyl), —N(C$_{1-8}$ alkyl)$_2$, —NH—SO$_2$—C$_{1-8}$ alkyl, —N(C$_{1-8}$ alkyl)-SO$_2$—C$_{1-8}$ alkyl, —NH—C(O)—(C$_{1-8}$ alkyl), —N(C$_{1-8}$ alkyl)-C(O)—(C$_{1-8}$ alkyl), —NH—C(O)O—C$_{1-8}$ alkyl, —N(C$_{1-8}$ alkyl)-C(O)O—C$_{1-8}$ alkyl, —NH—C(O)—NH$_2$, —NH—C(O)—NH(C$_{1-8}$ alkyl), —N(C$_{1-8}$ alkyl)-C(O)—NH(C$_{1-8}$ alkyl), —N(C$_{1-8}$ alkyl)-C(O)—N(C$_{1-8}$ alkyl)$_2$, —NH—C(O)—NH—SO$_2$—C$_{1-8}$ alkyl, —N(C$_{1-8}$ alkyl)-C(O)—NHSO$_2$—C$_{1-8}$ alkyl, —N($C_{1-8}$ alkyl)-C(O)—N($C_{1-8}$ alkyl)-$SO_2$—$C_{1-8}$ alkyl, —S—$C_{1-8}$ alkyl, —S(O)—$C_{1-8}$ alkyl, —$SO_2$—$C_{1-8}$ alkyl, —S-aryl, —S(O)-aryl, $SO_2$-aryl, —$SO_2NH_2$, —$SO_2$NH—($C_{1-8}$ alkyl), —$SO_2$N($C_{1-8}$ alkyl)$_2$;

W represents a group selected from —CH= or —N=;

X represents a group selected from —CH=CH—, —S—, or —N=CH—;

Y represents a group selected from —CH=CH— or —C≡C—;

A and B are independently selected from —OR', —SR, —NRR' or —NRCOR';

or, A and B together can form a substituted or unsubstituted 5 to 8 membered cyclic ring containing at least two heteroatoms selected from oxygen and sulfur;

or, A and B together represent group consisting of C=O, C=S, C=N(OR) or C=NNRR';

P is selected from the group consisting of —O—, —S—, —$CH_2$— and —NR—; or P may form a —CH=CH— moiety with the adjacent carbon atom;

Q is a group selected from hydrogen, —$CH_3$, —$CF_3$, OR, —COOR, —CONRR', —CR=CR—COOR'; —$OCH_2$ aryl-COOR, —$CH_2$O-aryl-COOR, —$CONHSO_2$R, —$CONHSO_2$ aryl, —$OCH_2$CONRR', —$NHSO_2$R, —$NHSO_2$ aryl, —$NHSO_2$NHR, —$SO_2$NHR, —$SO_2$NH aryl, —NHCOR, —NHCO(CRR')—COOR, —C(RR')—COOR, tetrazole, —C(RR')OH, —C(RR')CONRR', —$CH_2$NRR' or —$OCH_2$C(RR')OH;

R and R' are independently selected from the group consisting of hydrogen, —$C_{1-6}$ alkyl, —$C_{3-6}$ cycloalkyl, —$C_{1-3}$ alkyl (cycloalkyl), —$C_{3-6}$ alkenyl and —$C_{3-6}$ alkynyl or, R and R' along with the atom to which they are attached, together can form a substituted or unsubstituted 5 to 8 membered cyclic ring;

'm' is an, integer selected from 0 to 4, both inclusive;

with the proviso that when P is —$CH_2$—, then A and B both represent groups connected to carbon through heteroatom.

One aspect of the invention relates to compounds of general formula (Ic),

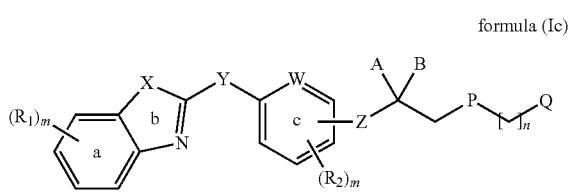

formula (Ic)

or the pharmaceutically acceptable salt thereof, wherein, $R_1$ and $R_2$ are independently selected from the group consisting of hydrogen, halogen, to —OH, —CN, —$NO_2$, —$NH_2$, —$C_{1-10}$-alkyl, —$C_{3-10}$ cycloalkyl, —O—$C_{1-8}$ alkyl (alkoxy), —O—$C_{3-8}$ cycloalkyl (cycloalkoxy), —S—$C_{1-8}$ alkyl (thioalkoxy), —C(O)—$C_{1-8}$ alkyl, —COOH, —C(O)$NH_2$, —C(O)NH—$C_{1-8}$ alkyl, —C(O)N($C_{1-8}$ alkyl)$_2$, —C(O)O—$C_{1-8}$ alkyl, —$C_{1-8}$ haloalkyl (haloalkoxy), —$C_{3-8}$ alkenyl, —$C_{3-8}$ alkynyl, —OC(O)—$NH_2$, —OC(O)—NH($C_{1-8}$ alkyl), —OC(O)—N($C_{1-8}$ alkyl)$_2$, —$NH_2$, —NH($C_{1-8}$ alkyl), —N($C_{1-8}$ alkyl)$_2$, —NH—$SO_2$—$C_{1-8}$ alkyl, —N($C_{1-8}$ alkyl)-$SO_2$—$C_{1-8}$ alkyl, —NH—C(O)—($C_{1-8}$ alkyl), —N($C_{1-8}$ alkyl)-C(O)—($C_{1-8}$ alkyl), —NH—C(O)O—$C_{1-8}$ alkyl, —N($C_{1-8}$ alkyl)-C(O)O—$C_{1-8}$ alkyl, —NH—C(O)—$NH_2$, —NH—C(O)—NH($C_{1-8}$ alkyl), —N($C_{1-8}$ alkyl)-C(O)—NH ($C_{1-8}$ alkyl), —N($C_{1-8}$ alkyl)-C(O)—N($C_{1-8}$ alkyl)$_2$, —NH—C(O)—NH—$SO_2$—$C_{1-8}$ alkyl, —N($C_{1-8}$ alkyl)-C(O)—NH$SO_2$—$C_{1-8}$ alkyl, —N($C_{1-8}$ alkyl)-C(O)—N($C_{1-8}$ alkyl)-$SO_2$—$C_{1-8}$ alkyl, —S—$C_{1-8}$ alkyl, —S(O)—$C_{1-8}$ alkyl, —$SO_2$—$C_{1-8}$ alkyl, —S-aryl, —S(O)-aryl, $SO_2$-aryl, —$SO_2NH_2$, —$SO_2$NH—($C_{1-8}$ alkyl), —$SO_2$N($C_{1-8}$ alkyl)$_2$;

W represents a group selected from —CH= or —N=;

X represents a group selected from —CH=CH—, —S—, or —N=CH—;

Y represents a group selected from —CH=CH— or —C≡C—;

A and B are independently selected from hydrogen, —OR', —SR, —NRR' and —NRCOR';

with a proviso that when B is hydrogen, P is selected from —O—, —S— or —NR—;

or, A and B together can form a substituted or unsubstituted 5 to 8 membered cyclic ring containing at least two heteroatoms selected from oxygen and sulfur;

or, A and B together represent group consisting of C=O, C=S, C=N(OR) or C=NNRR';

P is selected from the group consisting of —O—, —S—, —$CH_2$— and —NR—; or P may form a —CH=CH— moiety with the adjacent carbon atom; with a proviso that when B is hydrogen then P is selected from the group consisting of —O—, —S— and —NR—.

Q is a group selected from hydrogen, —$CH_3$, —$CF_3$, OR, —COOR, —CONRR', —CR=CR—COOR'; —$OCH_2$ aryl-COOR, —$CH_2$O-aryl-COOR, —$CONHSO_2$R, —$CONHSO_2$ aryl, —$OCH_2$CONRR', —$NHSO_2$R, —$NHSO_2$ aryl, —$NHSO_2$NHR, —$SO_2$NHR, —$SO_2$NH aryl, —NHCOR, —NHCO(CRR')—COOR, —C(RR')—COOR, tetrazole, —C(RR')OH, —C(RR')CONRR', —$CH_2$NRR' or —$OCH_2$C(RR')OH;

R and R' are independently selected from the group consisting of hydrogen, —$C_{1-6}$ alkyl, —$C_{3-6}$ cycloalkyl, —$C_{1-3}$ alkyl (cycloalkyl), —$C_{3-6}$ alkenyl and —$C_{3-6}$ alkynyl or, R and R' along with the atom to which they are attached, together can form a substituted or unsubstituted 5 to 8 membered cyclic ring;

'n' is an integer selected from 1, 2 or 3;

'm' is an integer selected from 0 to 4, both inclusive.

The invention also provides the use of compound of formula (I), (Ia), (Ib) or (Ic) or salt or N-oxides thereof for the preparation of pharmaceutical composition comprising compound of formula (I), (Ia), (Ib) or (Ic) or N-oxide thereof and a pharmaceutically acceptable carrier, diluent or excipient thereof.

Further the present invention also provides a method for treatment of disorders related to cysteinyl leukotriene, comprising administering to a mammal in need of such treatment an effective amount of compound of formula (I), (Ia), (Ib) or (Ic) or salt or N-oxides thereof.

DETAILED DESCRIPTION OF THE INVENTION

The present invention relates to novel cysteinyl leukotriene (specifically LTD4) antagonists, represented by the general formula (I),

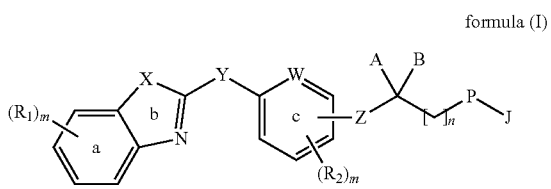

formula (I)

or the pharmaceutically acceptable salt thereof,
wherein,
ring 'a', ring 'b' and ring 'c' are independently an aryl or a heteroaryl ring optionally substituted by one or more identical or different radicals $R_1$ or $R_2$,
$R_1$ and $R_2$ are independently selected from the group consisting of hydrogen, halogen, —OH, —CN, —$NO_2$, —$NH_2$, —$C_{1-10}$-alkyl, —$C_{3-10}$ cycloalkyl, —O—$C_{1-8}$ alkyl (alkoxy), —O—$C_{3-8}$ cycloalkyl (cycloalkoxy), —S—$C_{1-8}$ alkyl (thioalkoxy), —C(O)—$C_{1-8}$ alkyl, —COOH, —C(O)$NH_2$, —C(O)NH—$C_{1-8}$ alkyl, —C(O)N($C_{1-8}$ alkyl)$_2$, —C(O)O—$C_{1-8}$ alkyl, —$C_{1-8}$ haloalkyl (haloalkoxy), —$C_{3-8}$ alkenyl, —$C_{3-8}$ alkynyl, —OC(O)—$NH_2$, —OC(O)—NH($C_{1-8}$ alkyl), —OC(O)—N($C_{1-8}$ alkyl)$_2$, —$NH_2$, —NH($C_{1-8}$ alkyl), —N($C_{1-8}$ alkyl)$_2$, —NH—$SO_2$—$C_{1-8}$ alkyl, —N($C_{1-8}$ alkyl)-$SO_2$—$C_{1-8}$ alkyl, —NH—C(O)—($C_{1-8}$ alkyl), —N($C_{1-8}$ alkyl)-C(O)—($C_{1-8}$ alkyl), —NH—C(O)O—$C_{1-8}$ alkyl, —N($C_{1-8}$ alkyl)-C(O)O—$C_{1-8}$ alkyl, —NH—C(O)—$NH_2$, —NH—C(O)—NH($C_{1-8}$ alkyl), —N($C_{1-8}$ alkyl)-C(O)—NH ($C_{1-8}$ alkyl), —N($C_{1-8}$ alkyl)-C(O)—N($C_{1-8}$ alkyl)$_2$, —NH—C(O)—NH—$SO_2$—$C_{1-8}$ alkyl, —N($C_{1-8}$ alkyl)-C(O)—$NHSO_2$—$C_{1-8}$ alkyl, —N($C_{1-8}$ alkyl)-C(O)—N($C_{1-8}$ alkyl)-$SO_2$—$C_{1-8}$ alkyl, —S—$C_{1-8}$ alkyl, —S(O)—$C_{1-8}$ alkyl, —$SO_2$—$C_{1-8}$ alkyl, —S-aryl, —S(O)-aryl, $SO_2$-aryl, —$SO_2NH_2$, —$SO_2$NH—($C_{1-8}$ alkyl), —$SO_2$N($C_{1-8}$ alkyl)$_2$;
W represents a group selected from —CH= or —N=;
X represents a group selected from —CH=CH—, —S—, or —N=CH—;
Y represents a group selected from —CH=CH— or —C≡C—;
Z represents a bond or group selected from —(CH2)$_n$—, —O—CH2- or —CH=CH—;
A is a group selected from hydrogen, —OH, —OR, —SR, —O(CH$_2$)$_n$ aryl, —O(CH$_2$)$_n$ heteroaryl, —OCOR, —OCO-aryl, —SCOR, —SCO-aryl, —NRR', —NRCOR', —NRCO-aryl, —NRCO-aryl-COOR, —NRCH$_2$ArCOOR, —NHCH$_2$(CR,R')OH, —NHCOCH$_2$ heteroaryl, —NHCOCH$_2$(CR,R')CH$_2$COOR, —NHCOCH$_2$(P)-aryl-COOR, —NHCOCH$_2$NRR', —NRSO$_2$R', —NRSO$_2$-aryl, —NR-CONRR', —NRCONR'-aryl, —NRCOCH$_2$-aryl-COOR', —NRPO(OR')(OH);
B is a group selected from hydrogen, —OR', —SR, —NRR' and —NRCOR';
or, A and B together can form a substituted or unsubstituted 5 to 8 membered cyclic ring containing at least two heteroatoms selected from oxygen and sulfur;
or, A and B together represent group consisting of C=O, C=S, C=N(OR) or C=NNRR';
P is selected from the group consisting of —O—, —S—, —CH$_2$— and —NR—; or P may form a —CH=CH— moiety with the adjacent carbon atom;
J represents a group selected from aryl-Q, heteroaryl-Q or —(CH$_2$)$_n$Q, wherein Q is a group selected from hydrogen, —CH$_3$, —CF$_3$, OR, —COOR, —CONRR', —CR=CR—COOR'; —OCH$_2$ aryl-COOR, —CH$_2$O-aryl-COOR, —CONHSO$_2$R, —CONHSO$_2$ aryl, —OCH$_2$CONRR', —NHSO$_2$R, —NHSO$_2$ aryl, —NHSO$_2$NHR, —SO$_2$NHR, —SO$_2$NH aryl, —NHCOR, —NHCO(CRR')—COOR, —C(RR')—COOR, tetrazole, —C(RR')OH, —C(RR')CONRR', —CH$_2$NRR' or —OCH$_2$C(RR')OH;
R and R' are independently selected from the group consisting of hydrogen, —C$_{1-6}$ alkyl, —C$_{3-6}$ cycloalkyl, —C$_{1-3}$ alkyl (cycloalkyl), —C$_{3-6}$ alkenyl and —C$_{3-6}$ alkynyl or, R and R' along with the atom to which they are attached, together can form a substituted or unsubstituted 5 to 8 membered cyclic ring;

'n' is an integer selected from 1, 2 or 3;
'm' is an integer selected from 0 to 4, both inclusive;
with the proviso that when P is —CH$_2$—, then A and B both represent groups connected to carbon through heteroatom and when B is hydrogen, then A is —NR—.
In one of the preferred embodiment provided are compounds of formula (I) wherein rings 'a' and 'b' comprise a fused hetero-cyclic aromatic ring system, preferably a substituted or unsubstituted quinolin, thiazole or a quinoxaline ring.
In yet another embodiment provided are compounds of formula (I) wherein the substitution pattern in the ring 'c' is (1, 2); (1, 3) or (1, 4) with respect to 'Y' and preferably (1, 3) as disclosed in the specification.
In yet another preferred embodiment provided are compounds of formula (I) wherein W is —CH=.
In yet another preferred embodiment provided are compounds of formula (I) wherein X is —CH=CH—.
In yet another preferred embodiment provided are compounds of formula (I) wherein Y is —CH=CH—.
In yet another preferred embodiment provided are compounds of formula (I) wherein Y is —CH=CH— having trans configuration.
In yet another preferred embodiment provided are compounds of formula (I) wherein Z represents a bond.
In yet another preferred embodiment provided are compounds of formula (I) wherein $R_1$ and $R_2$ are selected from hydrogen and halogen.
In yet another embodiment provided is compound of formula (Ia), formula (Ia)

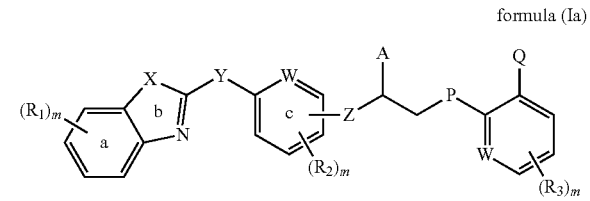

or the pharmaceutically acceptable salt thereof,
wherein,
$R_1$, $R_2$ and $R_3$ are independently selected from the group consisting of hydrogen, halogen, —OH, —CN, —$NO_2$, —$NH_2$, —$C_{1-10}$-alkyl, —$C_{3-10}$ cycloalkyl, —O—$C_{1-8}$ alkyl, —O—$C_{1-8}$ alkyl (alkoxy), —O—$C_{3-8}$ cycloalkyl (cycloalkoxy), —S—$C_{1-8}$ alkyl (thioalkoxy), —C(O)—$C_{1-8}$ alkyl, —COOH, —C(O)$NH_2$, —C(O)NH—$C_{1-8}$ alkyl, —C(O)N($C_{1-8}$ alkyl)$_2$, —C(O)O—$C_{1-8}$ alkyl, —$C_{1-8}$ haloalkyl (haloalkoxy), —$C_{3-8}$ alkenyl, —$C_{3-8}$ alkynyl, —OC(O)—$NH_2$, —OC(O)—NH($C_{1-8}$ alkyl), —OC(O)—N($C_{1-8}$ alkyl)$_2$, —NH($C_{1-8}$ alkyl), —N($C_{1-8}$ alkyl)$_2$, —NH—SO$_2$—$C_{1-8}$ alkyl, —N($C_{1-8}$ alkyl)-SO$_2$—$C_{1-8}$ alkyl, —NH—C(O)—($C_{1-8}$ alkyl), —N($C_{1-8}$ alkyl)-C(O)—($C_{1-8}$ alkyl), —NH—C(O)O—$C_{1-8}$ alkyl, —N($C_{1-8}$ alkyl)-C(O)O—$C_{1-8}$ alkyl, —NH—C(O)—$NH_2$, —NH—C(O)—NH($C_{1-8}$ alkyl), —N($C_{1-8}$ alkyl)-C(O)—NH($C_{1-8}$ alkyl), —N($C_{1-8}$ alkyl)-C(O)—N($C_{1-8}$ alkyl)$_2$, —NH—C(O)—NH—SO$_2$—$C_{1-8}$ alkyl, —N($C_{1-8}$ alkyl)-C(O)—NHSO$_2$—$C_{1-8}$ alkyl, —N($C_{1-8}$ alkyl)-C(O)—N($C_{1-8}$ alkyl)-SO$_2$—$C_{1-8}$ alkyl, —S—$C_{1-8}$ alkyl, —S(O)—$C_{1-8}$ alkyl, —SO$_2$—$C_{1-8}$ alkyl, —S-aryl, —S(O)-aryl, SO$_2$-aryl, —SO$_2$NH$_2$, —SO$_2$NH—($C_{1-8}$ alkyl), —SO$_2$N($C_{1-8}$ alkyl)$_2$;
W represents a group selected from —CH= or —N=;
X represents a group selected from —CH=CH—, —S—, or —N=CH—;

Y represents a group selected from —CH═CH— or —C≡C—;

A is a group selected from hydrogen, —OH, —OR, —SR, —O(CH₂)ₙ aryl, —O(CH₂)ₙ heteroaryl, —OCOR, —OCO-aryl, —SCOR, —SCO-aryl, —NRR', —NRCOR', —NRCO-aryl, —NRCO-aryl-COOR, —NRCH₂ArCOOR, —NHCH₂(CR,R')OH, —NHCOCH₂ heteroaryl, —NHCOCH₂(CR,R')CH₂COOR, —NHCOCH₂(P)-aryl-COOR, —NHCOCH₂NRR', —NRSO₂R', —NRSO₂-aryl, —NR-CONRR', —NRCONR'-aryl, —NRCOCH₂-aryl-COOR', —NRPO(OR')(OH); with a proviso that when A is —OR or —SR, then is P is selected from —O—, —S— or —NR— and when A is —NR—, P is selected from —O—, —S—, —NR— or —CH₂—;

P is selected from the group consisting of —O—, —S—, —CH₂— and —NR—; or P may form a —CH═CH— moiety with the adjacent carbon atom;

Q is a group selected from hydrogen, —CH₃, —CF₃, OR, —COOR, —CONRR', —CR═CR—COOR'; —OCH₂ aryl-COOR, —CH₂O-aryl-COOR, —CONHSO₂R, —CONHSO₂ aryl, —OCH₂CONRR', —NHSO₂R, —NHSO₂ aryl, —NHSO₂NHR, —SO₂NHR, —SO₂NH aryl, —NHCOR, —NHCO(CRR')—COOR, —C(RR')—COOR, tetrazole, —C(RR')OH, —C(RR')CONRR', —CH₂NRR' or —OCH₂C(RR')OH;

R and R' are independently selected from the group consisting of hydrogen, —C₁₋₆ alkyl, —C₃₋₆ cycloalkyl, —C₁₋₃ alkyl (cycloalkyl), —C₃₋₆ alkenyl and —C₃₋₆ alkynyl or, R and R' along with the atom to which they are attached, together can form a substituted or unsubstituted 5 to 8 membered cyclic ring;

'm' is an integer selected from 0 to 4, both inclusive;

with the proviso that when P is —CH₂—, then A is —NR—.

In yet another preferred embodiment provided are compounds of formula (Ia) wherein W is —CH═.

In yet another preferred embodiment provided are compounds of formula (Ia) wherein X is —CH═CH—.

In yet another preferred embodiment provided are compounds of formula (Ia) wherein Y is —CH═CH—.

In yet another preferred embodiment provided are compounds of formula (I) wherein Y is —CH═CH— having trans configuration.

In yet another preferred embodiment provided are compounds of formula (Ia) wherein Z represents a bond.

In yet another preferred embodiment provided are compounds of formula (Ia) wherein R₁ and R₂ are selected from hydrogen and halogen.

In yet another preferred embodiment provided are compounds of formula (Ia) wherein A is —OR or —SR and P is selected from —O—, —S— or —NR—.

In yet another preferred embodiment provided are compounds of formula (Ia) wherein A is —NR— and P is selected from —O—, —S—, —NR— or —CH₂—.

In yet another preferred embodiment provided are compounds of formula (Ia) wherein Q is a group selected from hydrogen, OR, —COOR, —CONRR', —CONHSO₂R, —NHCO(CRR')—COOR, —C(RR')OH, or —OCH₂C(RR')OH and R and R' are as defined above;

In yet another embodiment provided is compound of formula (Ib),

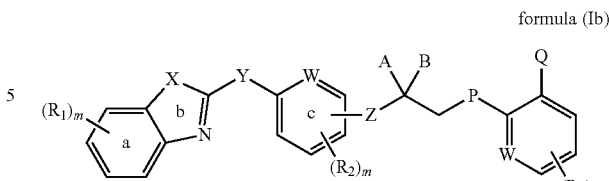

formula (Ib)

or the pharmaceutically acceptable salt thereof,
wherein,

R₁, R₂ and R₃ are independently selected from the group consisting of hydrogen, halogen, —OH, —CN, —NO₂, —NH₂, —C₁₋₁₀-alkyl, —C₃₋₁₀ cycloalkyl, —O—C₁₋₈ alkyl, —O—C₁₋₈ alkyl (alkoxy), —O—C₃₋₈ cycloalkyl (cycloalkoxy), —S—C₁₋₈ alkyl (thioalkoxy), —C(O)—C₁₋₈ alkyl, —COOH, —C(O)NH₂, —C(O)NH—C₁₋₈ alkyl, —C(O)N(C₁₋₈ alkyl)₂, —C(O)O—C₁₋₈ alkyl, —C₁₋₈ haloalkyl (haloalkoxy), —C₃₋₈ alkenyl, —C₃₋₈ alkynyl, —OC(O)—NH₂, —OC(O)—NH(C₁₋₈ alkyl), —OC(O)—N(C₁₋₈ alkyl)₂, —NH(C₁₋₈ alkyl), —N(C₁₋₈ alkyl)₂, —NH—SO₂—C₁₋₈ alkyl, —N(C₁₋₈ alkyl)-SO₂—C₁₋₈ alkyl, —NH—C(O)—(C₁₋₈ alkyl), —N(C₁₋₈ alkyl)-C(O)—(C₁₋₈ alkyl), —NH—C(O)O—C₁₋₈ alkyl, —N(C₁₋₈ alkyl)-C(O)O—C₁₋₈ alkyl, —NH—C(O)—NH₂, —NH—C(O)—NH(C₁₋₈ alkyl), —N(C₁₋₈ alkyl)-C(O)—NH(C₁₋₈ alkyl), —N(C₁₋₈ alkyl)-C(O)—N(C₁₋₈ alkyl)₂, —NH—C(O)—NH—SO₂—C₁₋₈ alkyl, —N(C₁₋₈ alkyl)-C(O)—NHSO₂—C₁₋₈ alkyl, —N(C₁₋₈ alkyl)-C(O)—N(C₁₋₈ alkyl)-SO₂—C₁₋₈ alkyl, —S—C₁₋₈ alkyl, —S(O)—C₁₋₈ alkyl, —SO₂—C₁₋₈ alkyl, —S-aryl, —S(O)-aryl, SO₂-aryl, —SO₂NH₂, —SO₂NH—(C₁₋₈ alkyl), —SO₂N(C₁₋₈ alkyl)₂;

W represents a group selected from —CH═ or —N═;

X represents a group selected from —CH═CH—, —S—, or —N═CH—;

Y represents a group selected from —CH═CH— or —C≡C—;

A and B are independently selected from —OR', —SR, —NRR' or —NRCOR';

or, A and B together can form a substituted or unsubstituted 5 to 8 membered cyclic ring containing at least two heteroatoms selected from oxygen and sulfur;

or, A and B together represent group consisting of C═O, C═S, C═N(OR) or C═NNRR';

P is selected from the group consisting of —O—, —S—, —CH₂— and —NR—; or P may form a —CH═CH— moiety with the adjacent carbon atom;

Q is a group selected from hydrogen, —CH₃, —CF₃, OR, —COOR, —CONRR', —CR═CR—COOR'; —OCH₂ aryl-COOR, —CH₂O-aryl-COOR, —CONHSO₂R, —CONHSO₂ aryl, OCH₂CONRR', —NHSO₂R, —NHSO₂ aryl, —NHSO₂NHR, —SO₂NHR, —SO₂NH aryl, —NH-COR, —NHCO(CRR')—COOR, —C(RR')—COOR, tetrazole, —C(RR')OH, —C(RR')CONRR', —CH₂NRR' or —OCH₂C(RR')OH;

R and R' are independently selected from the group consisting of hydrogen, —C₁₋₆ alkyl, —C₃₋₆ cycloalkyl, —C₁₋₃ alkyl (cycloalkyl), —C₃₋₆ alkenyl and —C₃₋₆ alkynyl or, R and R' along with the atom to which they are attached, together can form a substituted or unsubstituted 5 to 8 membered cyclic ring;

'm' is an integer selected from 0 to 4, both inclusive;

with the proviso that when P is —CH₂—, then A and B both represent groups connected to carbon through heteroatom.

In yet another preferred embodiment provided are compounds of formula (Ib) wherein W is —CH═.

In yet another preferred embodiment provided are compounds of formula (Ib) wherein X is —CH═CH—.

In yet another preferred embodiment provided are compounds of formula (Ib) wherein Y is —CH═CH—.

In yet another preferred embodiment provided are compounds of formula (I) wherein Y is —CH═CH— having trans configuration.

In yet another preferred embodiment provided are compounds of formula (Ib) wherein Z represents a bond.

In yet another preferred embodiment provided are compounds of formula (Ib) wherein $R_1$ and $R_2$ are selected from hydrogen and halogen.

In yet another preferred embodiment provided are compounds of formula (Ib) wherein A and B is —OR' and R' is selected from the group consisting of hydrogen, —$C_{1-6}$ alkyl, —$C_{3-6}$ cycloalkyl, —$C_{3-6}$ alkenyl or —$C_{3-6}$ alkynyl.

In yet another preferred embodiment provided are compounds of formula (Ib) wherein A and B together form a substituted or unsubstituted 5 to 8 membered cyclic ring containing at least two heteroatoms selected from oxygen and sulfur.

In yet another preferred embodiment provided are compounds of formula (Ib) wherein A and B together represent group C═N(OR) and R is selected from the group consisting of hydrogen, —$C_{1-6}$ alkyl, —$C_{3-6}$ cycloalkyl, —$C_{3-6}$ alkenyl or —$C_{3-6}$ alkynyl.

In yet another preferred embodiment provided are compounds of formula (Ib) wherein Q is a group selected from hydrogen, OR, —COOR, —CONRR', —CH$_2$O-aryl-COOR, —C(RR')—COOR, —CH$_2$NRR', tetrazole, —C(RR')OH, or —OCH$_2$C(RR')OH and R and R' are as defined above;

In yet another embodiment provided is compound of formula (Ic),

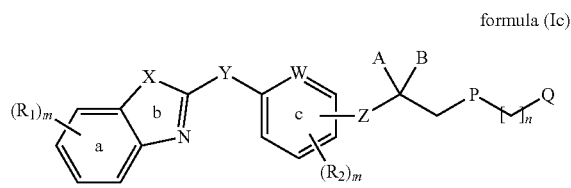

formula (Ic)

or the pharmaceutically acceptable salt thereof,
wherein,
$R_1$ and $R_2$ are independently selected from the group consisting of hydrogen, halogen, —OH, —CN, —NO$_2$, —NH$_2$, —$C_{1-10}$-alkyl, —$C_{3-10}$ cycloalkyl, —O—$C_{1-8}$ alkyl (alkoxy), —O—$C_{3-8}$ cycloalkyl (cycloalkoxy), —S—$C_{1-8}$ alkyl (thioalkoxy), —C(O)—$C_{1-8}$ alkyl, —COOH, —C(O)NH$_2$, —C(O)NH—$C_{1-8}$ alkyl, —C(O)N($C_{1-8}$ alkyl)$_2$, —C(O)O—$C_{1-8}$ alkyl, —$C_{1-8}$ haloalkyl (haloalkoxy), —$C_{3-8}$ alkenyl, —$C_{3-8}$ alkynyl, —OC(O)—NH$_2$, —OC(O)—NH($C_{1-8}$ alkyl), —OC(O)—N($C_{1-8}$ alkyl)$_2$, —NH$_2$, —NH($C_{1-8}$ alkyl), —N($C_{1-8}$ alkyl)$_2$, —NH—SO$_2$—$C_{1-8}$ alkyl, —N($C_{1-8}$ alkyl)-SO$_2$—$C_{1-8}$ alkyl, —NH—C(O)—($C_{1-8}$ alkyl), —N($C_{1-8}$ alkyl)-C(O)—($C_{1-8}$ alkyl), —NH—C(O)O—$C_{1-8}$ alkyl, —N($C_{1-8}$ alkyl)-C(O)O—$C_{1-8}$ alkyl, —NH—C(O)—NH$_2$, —NH—C(O)—NH($C_{1-8}$ alkyl), —N($C_{1-8}$ alkyl)-C(O)—NH ($C_{1-8}$ alkyl), —N($C_{1-8}$ alkyl)-C(O)—N($C_{1-8}$ alkyl)$_2$, —NH—C(O)—NH—SO$_2$—$C_{1-8}$ alkyl, —N($C_{1-8}$ alkyl)-C(O)—NHSO$_2$—$C_{1-8}$ alkyl, —N($C_{1-8}$ alkyl)-C(O)—N($C_{1-8}$ alkyl)-SO$_2$—$C_{1-8}$ alkyl, —S—$C_{1-8}$ alkyl, —S(O)—$C_{1-8}$ to alkyl, —SO$_2$—$C_{1-8}$ alkyl, —S-aryl, —S(O)-aryl, SO$_2$-aryl, —SO$_2$NH$_2$, —SO$_2$NH—($C_{1-8}$ alkyl), —SO$_2$N($C_{1-8}$ alkyl)$_2$;
W represents a group selected from —CH═ or —N═;
X represents a group selected from —CH═CH—, —S—, or —N═CH—;
Y represents a group selected from —CH═CH— or —C≡C—;
A and B are independently selected from hydrogen, —OR', —SR, —NRR' and —NRCOR'; with a proviso that when B is hydrogen, P is selected from —O—, —S— or —NR—;
or, A and B together can form a substituted or unsubstituted 5 to 8 membered cyclic ring containing at least two heteroatoms selected from oxygen and sulfur;
or, A and B together represent group consisting of C═O, C═S, C═N(OR) or C═NNRR';
P is selected from the group consisting of —O—, —S—, —CH$_2$— and —NR—; or P may form a —CH═CH— moiety with the adjacent carbon atom; with a proviso that when B is hydrogen then P is selected from the group consisting of —O—, —S— and —NR—.

Q is a group selected from hydrogen, —CH$_3$, —CF$_3$, OR, —COOR, —CONRR', —CR═CR—COOR'; —OCH$_2$ aryl-COOR, —CH$_2$O-aryl-COOR, —CONHSO$_2$R, —CONHSO$_2$ aryl, —OCH$_2$CONRR', —NHSO$_2$R, —NHSO$_2$ aryl, —NHSO$_2$NHR, —SO$_2$NHR, —SO$_2$NH aryl, —NHCOR, —NHCO(CRR')—COOR, —C(RR')—COOR, tetrazole, —C(RR')OH, —C(RR')CONRR', —CH$_2$NRR' or —OCH$_2$C(RR')OH;
R and R' are independently selected from the group consisting of hydrogen, —$C_{1-6}$ alkyl, —$C_{3-6}$ cycloalkyl, —$C_{1-3}$ alkyl (cycloalkyl), —$C_{3-6}$ alkenyl and —$C_{3-6}$ alkynyl or, R and R' along with the atom to which they are attached, together can form a substituted or unsubstituted 5 to 8 membered cyclic ring;
'm' is an integer selected from 0 to 4, both inclusive.

In yet another preferred embodiment provided are compounds of formula (Ic) wherein W is —CH═.

In yet another preferred embodiment provided are compounds of formula (Ic) wherein X is —CH═CH—.

In yet another preferred embodiment provided are compounds of formula (Ic) wherein Y is —CH═CH—.

In yet another preferred embodiment provided are compounds of formula (I) wherein Y is —CH═CH— having trans configuration.

In yet another preferred embodiment provided are compounds of formula (Ic) wherein Z represents a bond.

In yet another preferred embodiment provided are compounds of formula (Ic) wherein $R_1$ and $R_2$ are selected from hydrogen and halogen.

In addition to the above text, and in the entire disclosure, the terms described have the following meanings unless otherwise indicated.

The following are definitions of the terms used in this specification. The initial definition provided for a group or term herein applies to that group or term throughout the present specification, individually or as part of another group, unless otherwise indicated.

The general terms used herein-before and hereinafter preferably have within the context of this disclosure the following meanings, unless otherwise indicated.

The term "alkyl" refers to a hydrocarbon chain radical that includes solely carbon and to hydrogen atoms in the backbone, either linear or branched, having from one to eight carbon atoms, both inclusive, and which is attached to the rest of the molecule by a single bond, e.g., methyl, ethyl, n-propyl, 1-methylethyl (isopropyl), n-butyl, n-pentyl, and 1,1-dimethylethyl (t-butyl). The term "$C_{1-8}$ alkyl" refers to an alkyl chain, linear or branched having 1 to 8 carbon atoms, both inclusive. Unless set forth or recited to the contrary, all alkyl groups described or claimed herein may be, substituted or unsubstituted.

The term "alkenyl" refers to a hydrocarbon chain containing from 3 to 10 carbon atoms, both inclusive and including at least one carbon-carbon double bond which is not in the 1 position, and may have (E) or (Z) configuration. Non-limiting examples of alkenyl groups include 2-propenyl (allyl), 2-methyl-2-propenyl, and (Z)-2-butenyl. Unless set forth or recited to the contrary, all alkenyl groups described or claimed herein may be straight chain or branched, substituted or unsubstituted.

The term "alkynyl" refers to a hydrocarbyl radical having at least one carbon-carbon triple bond which is not in the 1 position, and having 3 to about 12 carbon atoms, both inclusive (with radicals having 3 to about 10 carbon atoms being preferred).

Non-limiting examples of alkynyl groups include 2-propynyl and 3-butynyl. Unless set, forth or recited to the contrary, all alkynyl groups described or claimed herein may be straight chain or branched, substituted or unsubstituted.

The term "alkoxy" denotes an alkyl group attached via an oxygen linkage to the rest of the molecule. Representative examples of such groups are —$OCH_3$ and —$OC_2H_5$. Unless set forth or recited to the contrary, all alkoxy groups described or claimed herein may be straight chain or branched, substituted or unsubstituted.

The terms "halogen" or "halo" means fluorine, chlorine, bromine or iodine.

Similarly, "haloalkyl" or "haloalkoxy" refers to an alkyl or alkoxy group substituted with one or more halogen atoms.

The term "cycloalkyl" denotes a non-aromatic mono-, or multicyclic ring system of 3 to about 12 carbon atoms. Monocyclic rings include, but are not limited to cyclopropyl, cyclobutyl, cyclopentyl and cyclohexyl. Examples of simple multicyclic cycloalkyl groups include perhydronapthyl, perhydroindenyl etc; bridged multicyclic groups include adamantyl and norbornyl etc, and spriromulticyclic groups for e.g., spiro(4,4)non-2-yl. Unless set forth or recited to the contrary, all cycloalkyl groups described or claimed herein may be substituted or unsubstituted.

The term "cycloalkylalkyl" refers to a cyclic ring-containing radical having 3 to about 8 carbon atoms directly attached to an alkyl group. The cycloalkylalkyl group may be attached to the main structure at any carbon atom in the alkyl group that results in the creation of a stable structure. Non-limiting examples of such groups include cyclopropylmethyl, cyclobutylethyl and cyclopentylethyl. Unless set forth or recited to the contrary, all cycloalkylalkyl groups described or claimed herein may be substituted or unsubstituted.

The term "cycloalkenyl" refers to a cyclic ring-containing radical having 3 to about 8 carbon atoms with at least one carbon-carbon double bond which is not in the 1 position, such as cyclopropenyl, cyclobutenyl and cyclopentenyl. Unless set forth or recited to the contrary, all cycloalkenyl groups described or claimed herein may be substituted or unsubstituted.

The term "aryl" refers to an aromatic radical having 6 to 14 carbon atoms, including monocyclic, bicyclic and tricyclic aromatic systems such as phenyl, naphthyl, tetrahydronapthyl, indanyl and biphenyl. Unless set forth or recited to the contrary, all aryl groups described or claimed herein may be substituted or unsubstituted.

The term "arylalkyl" refers to an aryl group as defined above directly bonded to an alkyl group as defined above, e.g., —$CH_2C_6H_5$ and —$C_2H_4C_6H_5$. Unless set forth or recited to the contrary, all arylalkyl groups described or claimed herein may be substituted or unsubstituted.

The term "heteroaryl" unless otherwise specified refers to substituted or unsubstituted 5 to 14 membered aromatic heterocyclic ring radicals with one or more heteroatom(s) independently selected from N, O or S. The heteroaryl may be a mono-, bi- or tricyclic ring system. The heteroaryl ring radical may be attached to the main structure at any heteroatom or carbon atom that results in the creation of a stable structure. Examples of such heteroaryl ring radicals include, but are not limited to oxazolyl, isoxazolyl, imidazolyl, furyl, indolyl, isoindolyl, pyrrolyl, triazolyl, triazinyl, tetrazoyl, thienyl, thiazolyl, isothiazolyl, pyridyl, pyrimidinyl, pyrazinyl, pyridazinyl, benzofuranyl, benzothiazolyl, benzoxazolyl, benzimidazolyl, benzothienyl, benzopyranyl, carbazolyl, quinolinyl, isoquinolinyl, quinazolinyl, cinnolinyl, naphthyridinyl, pteridinyl, purinyl, quinoxalinyl, quinolinyl, isoquinolinyl, thiadiazolyl, indolizinyl, acridinyl, phenazinyl, imidazo[1,2-a]pyridyl, imidazo[1,2-a]pyridine and phthalazinyl. Unless set forth or recited to the contrary, all heteroaryl groups described or claimed herein may be substituted or unsubstituted.

The term "heteroarylalkyl" refers to a heteroaryl ring radical directly bonded to an alkyl group. The heteroarylalkyl radical may be attached to the main structure at any carbon atom in the alkyl group that results in the creation of a stable structure. Unless set forth or recited to the contrary, all heteroarylalkyl groups described or claimed herein may be substituted or unsubstituted.

Unless otherwise specified, the term "substituted" as used herein refers to a group or moiety having one or more of the substituents attached to the structural skeleton of the group or moiety, including, but not limited to such substituents as deuterium, hydroxy, halogen, carboxyl, cyano, nitro, oxo (=O), thio (=S), alkyl, haloalkoxy, alkenyl, alkynyl, aryl, arylalkyl, cycloalkyl, cycloalkylalkyl, cycloalkenyl, amino, alkylamino, dialkylamino, heteroaryl, heterocyclylalkyl ring, heteroarylalkyl, heterocyclic ring, guanidine, alkylguanidine, —$COOR_X$, —$C(O)R_X$, —$C(S)R_X$, —$C(O)NRxRy$, —(O) $ONRxRy$, —$NRxCONRyRz$, —$N(Rx)SORy$, —$N(Rx)SO_2Ry$, —(=N—N(Rx)Ry), —$NRxC(O)ORy$, —$NRxRy$, —$NRxC(O)Ry$, —$NrxC(S)Ry$, —$NRxC(S)NRyRz$, —$SONRxRy$, —$SO_2NRxRy$, —$OR_X$, —$ORxC(O)NRyRz$, —$ORxC(O)ORy$, —$OC(O)RX$, —$OC(O)NRxRy$, —$RxNRyC(O)Rz$, —$RxORy$, —$RxC(O)ORy$, —$RxC(O)NRyRz$, —$RxC(O)Ry$, —$RxOC(O)Ry$, —$SR_X$, —$SOR_X$, —$SO_2R_X$, and —$ONO_2$, wherein Rx, Ry and Rz are independently selected from hydrogen, alkyl, alkoxy, alkenyl, alkynyl, aryl, arylalkyl, cycloalkyl, cycloalkenyl, amino, alkylamino, dialkylamino, aryl, heteroaryl, heterocyclylalkyl ring, heteroarylalkyl, or substituted or unsubstituted heterocyclic ring.

As mentioned above the term "heterocyclic ring" or "heterocyclyl" unless otherwise specified refers to substituted or unsubstituted non-aromatic 3 to 15 membered ring radical which consists of carbon atoms and from one to five heteroatoms selected from nitrogen, phosphorus, oxygen and sulfur. The heterocyclic ring radical may be a mono-, bi- or tricyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quarternized; also, unless otherwise constrained by the definition the heterocyclic ring or heterocyclyl may optionally contain one or more olefinic bond(s). Examples of such heterocyclic ring radicals include, but are not limited to azepinyl, azetidinyl, benzodioxolyl, benzodioxanyl, chromanyl, dioxolanyl, dioxaphospholanyl, decahydroisoquinolyl, indanyl, indolinyl, isoindolinyl, isochromanyl, isothiazolidinyl, isoxazolidinyl, morpholinyl, oxazolinyl, oxazolidinyl, oxadiazolyl, 2-oxopiperazinyl, 2-oxopiperidinyl, 2-oxopyrrolidinyl, 2-oxoazepinyl, octahydroindolyl, octahydroisoindolyl, perhydroazepinyl, piperazinyl, 4-piperidonyl, pyrrolidinyl, piperidinyl, phenothiazinyl, phenoxazinyl, quinuclidinyl, tetrahydroisquinolyl, tetrahydrofuryl, tetrahydropyranyl, thiazolinyl, thiazolidinyl, thiamorpholinyl, thiamorpholinyl sulfoxide and thiamorpholinyl sulfone. The heterocyclic ring radical may be attached to the main structure at any heteroatom or carbon atom that results in the creation of a stable structure. Unless set forth or recited to the contrary, all heterocyclyl groups described or claimed herein may be substituted or unsubstituted.

The term "heterocyclylalkyl" refers to a heterocyclic ring radical directly bonded to an alkyl group. The heterocyclylalkyl radical may be attached to the main structure at any carbon atom in the alkyl group that results in the creation of a stable structure. Unless set forth or recited to the contrary, all heterocyclylalkyl groups described or claimed herein may be substituted or unsubstituted.

The compounds in this invention may form acidic salts when an amine or a basic function is present on the molecule. The acids derived from either natural or synthetic and may usually contain carboxylic, sulfonic function. Alternatively the acid salts may be prepared from any of the mineral acids such as hydrochloric acid, sulfuric acid, boric acid etc., making them chlorides, sulphates, nitrates, phosphates, borates etc.

The compounds in this invention may also form basic salts when acidic function such as carboxylic, sulphonic, tetrazolyl, and acylaminosuphonates are present on the molecule. The bases required for the salt formation may be derived from either natural or synthetic and may usually contain substituted or unsubstituted primary, secondary, tertiary amine function such as ethyl amine, isopropyl amine, tert butyl amine, trialkyl amines, meglumine etc. Alternatively the basic salts may be prepared to from any of the alkaline or alkaline earth metal derived hydroxides or carbonates such as sodium hydroxide, magnesium hydroxide etc.

Both the acidic and basic salts may be utilized even as in the purification processes for the final products and/the intermediates. If the compounds contain more than one acid function such as in diacids the salts may be formed from one or more bases appropriately to maintain the electrical neutrality.

Some of the compounds described herein relate to compound of formula (I), (Ia), (Ib) or (Ic) are having one or more chiral centers and are referred by racemic mixture of 'R' and 'S' isomers or either of the form depends on the origin or the conditions of their synthesis. Optical isomers may be resolved if necessary. The resolution process may be best done at an intermediate stage or at the final product stage in some cases.

Some of the compounds described herein relate to compound of formula (I), (Ia), (Ib) or (Ic) are having one or more 'alkenes' and may be represented by either 'cis' or 'trans' configurational isomers preferably the 'trans' isomer. In the case of 'oximes' may contain 'syn' or 'anti' configuration or a mixture there of.

The novel compounds presented in this invention can be used for the said purpose either alone or in combination with NSAIDs such as COX-2 inhibitors, H1 antagonists, PDE IV inhibitors or even with steroids in various pathological conditions such as migraine, urticaria, allergic disorders, asthma or COPD. Alternatively these compounds may be used as bronco dilators or even as lipoxinase inhibitors.

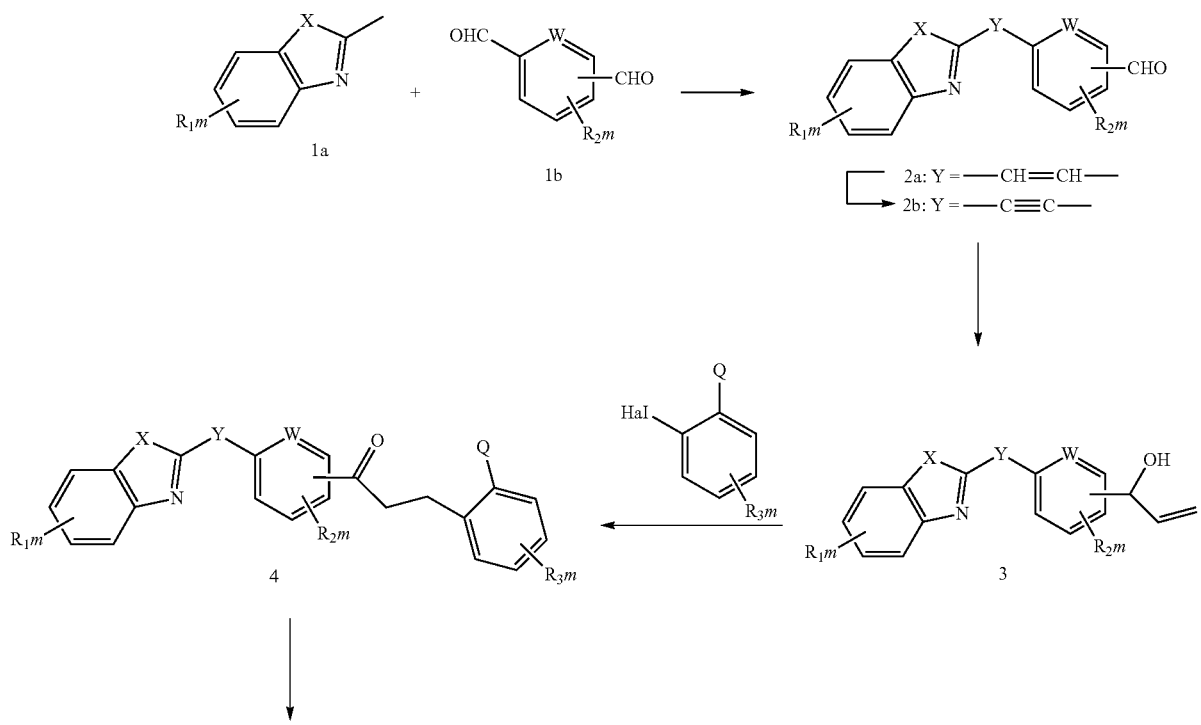

Scheme 1

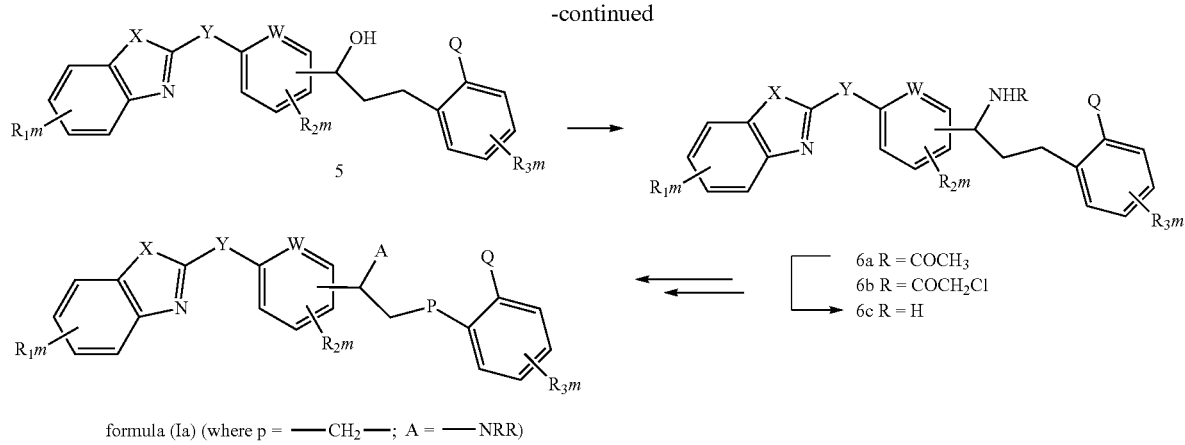

formula (Ia) (where p = —CH$_2$—; A = —NRR)

In one embodiment, in a general synthetic Scheme 1 some of the compounds of the to formula Ia were obtained from the intermediate-alcohol 5. Such a quinoline analogue is described in the literature M. Labelle et. al., Bio. Org. Med. Chem. Lett., 1994, 4, 463 or M. Labelle et. al., ibid, 1995, 5, 293. On Ritter reaction in presence of acetonitrile or chloro-acetonitrile and an acid or a Lewis acid, intermediate 5 converts to acetamide 6a or chloro-acetamide 6b, which on acidic hydrolysis and esterification gives the amine 6c. Acids used in Ritter reaction process are chosen from strong acids such as sulphuric acid, alkyl sulphonic acids, halosulphonic acids, haloalkyl sulphonic acids, mineral acids, organic acids such a trifluoroacetic acid or formic acid etc. Lewis acids/acid salts such as TMS-triflate, scandium triflate, bismuth triflate etc may also be used. A combination of acids may also be used.

Treatment of 6c with various electrophilic reagents such as acid chlorides/acidanhydrides/isocyanates/carbamoyl chlorides/thiocarbomoyl chlorides/alkyl halides/epoxides/sulphonylchlorides etc as exemplified in FIG. 1 will render some of the compounds such as amides/amide acids/carbamates/ureas as represented in (Ia.1 to Ia.86) given in Table 1. The chiral amine derivatives can be prepared by taking chiral version of alcohol 5 or by resolving the racemic amine mixture of 6c using a chiral acid such as tartaric acid/chiral sulfonic acid/mandelic acid etc., as a diastereomeric salt followed by neutralization. Some other derivatives of Table 1 have been synthesized by the treatment of amine 6c with di-aldehydes or di-halides to get the hetero-cyclic derivatives.

FIG. 1

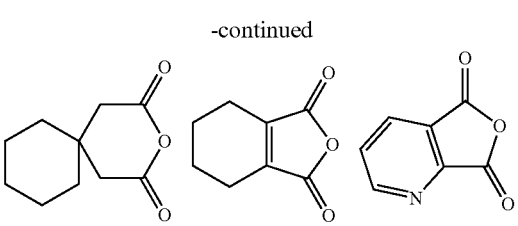

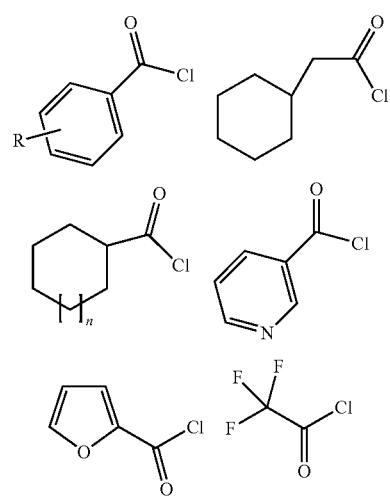

-continued

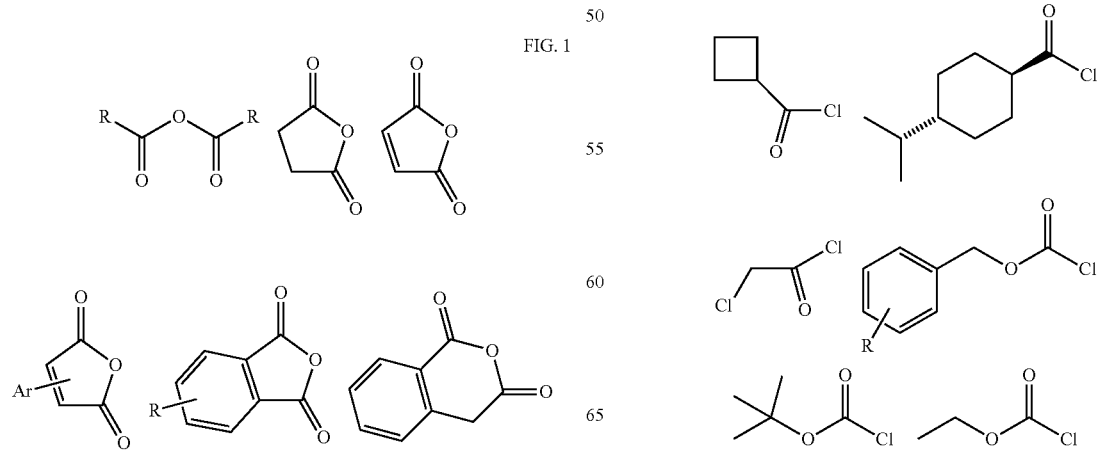

-continued

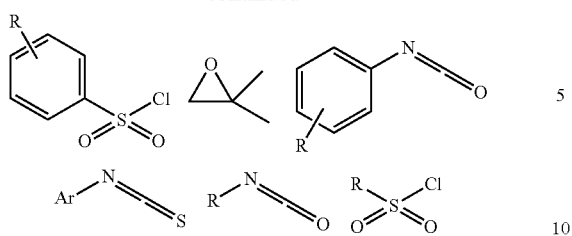
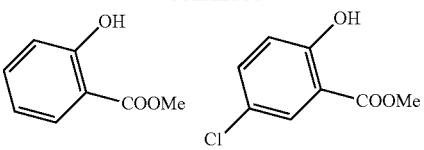

The nucleophilic displacement reaction on chloro-acetamide 6b with selected nucleophiles such as phenol/phenoxides/thiophenols/thiophenoxides/amines/amino acid derivatives as shown in FIG. 2 resulted in some of the derivatives either directly or by following a hydrolysis step as represented in Table-1.

FIG. 2

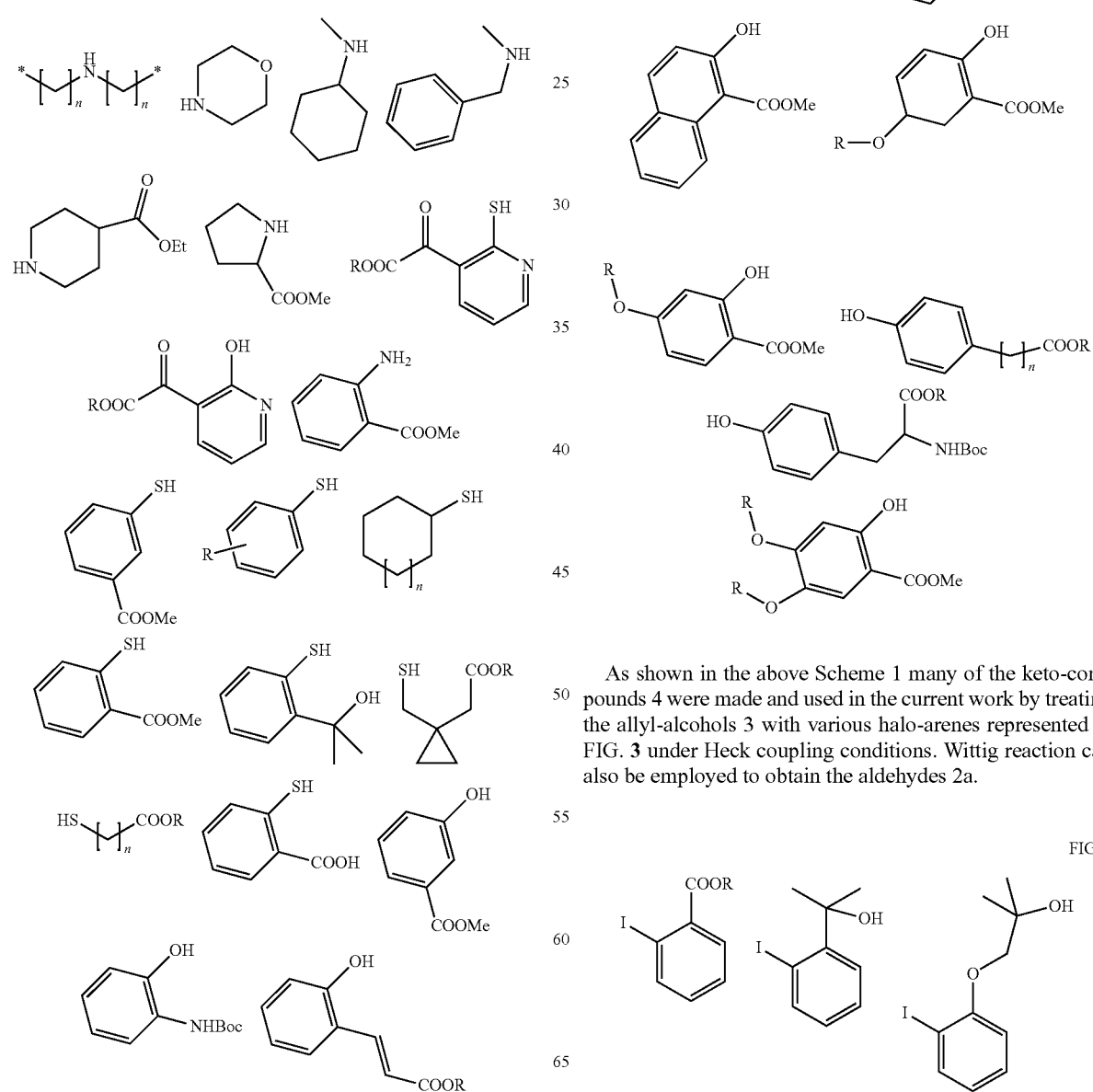

As shown in the above Scheme 1 many of the keto-compounds 4 were made and used in the current work by treating the allyl-alcohols 3 with various halo-arenes represented in FIG. 3 under Heck coupling conditions. Wittig reaction can also be employed to obtain the aldehydes 2a.

FIG. 3

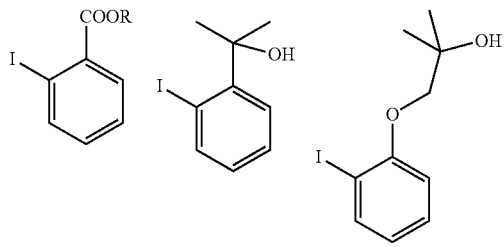

-continued

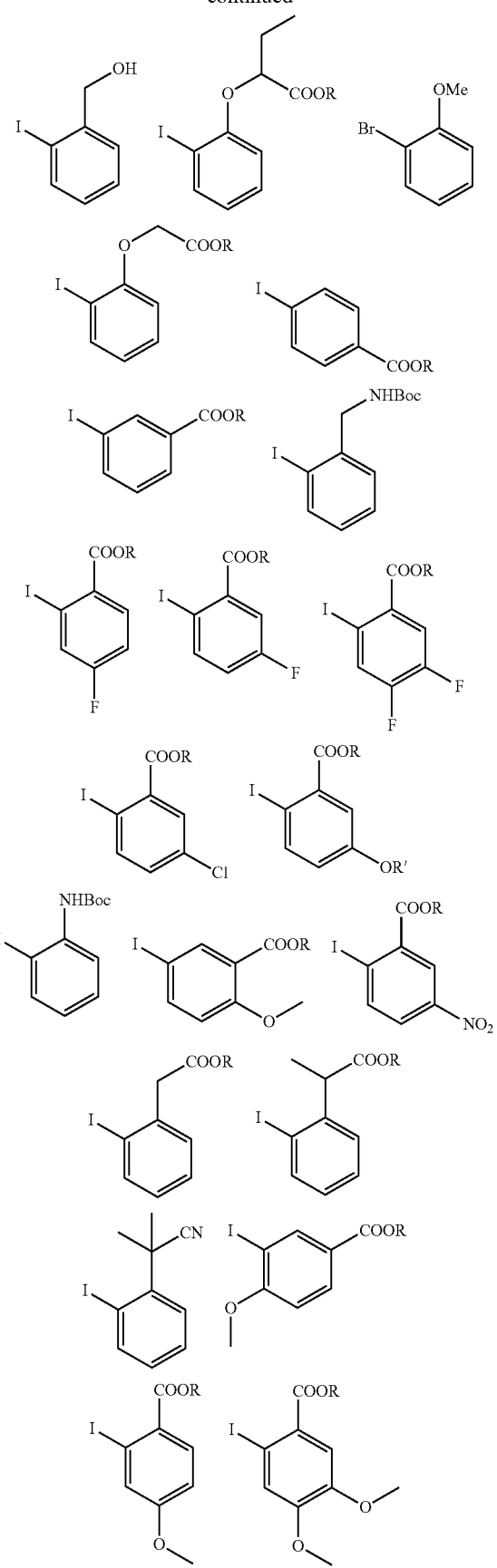
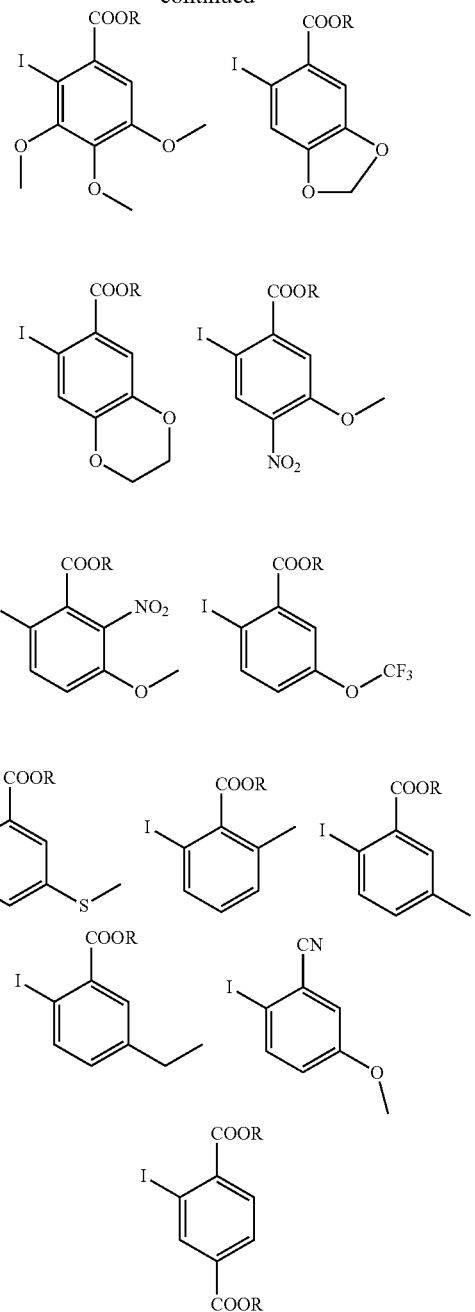

Allyl alcohols 3 required in this work were in-turn obtained from the aldehydes 2a/2b under standard Grignard reaction conditions using vinyl magnesium reagents. Aldehydes such a 2a can be easily synthesized by condensing the 2-methyl substituted chromophores derived from quinolin/quinoxaline/benz(c)thiazole represented as 1a in presence of organic anhydrides such as acetic anhydride/propionic anhydride with aryl dialdehydes 1b at elevated temperatures either with or without a solvent such as hexane, heptane, toluene, xylene etc. Alternative methods of this process Haloarenes, used for the synthesis of the compounds of the present invention can be obtained directly from commercial sources or prepared by involving multi-step synthesis known in the art.

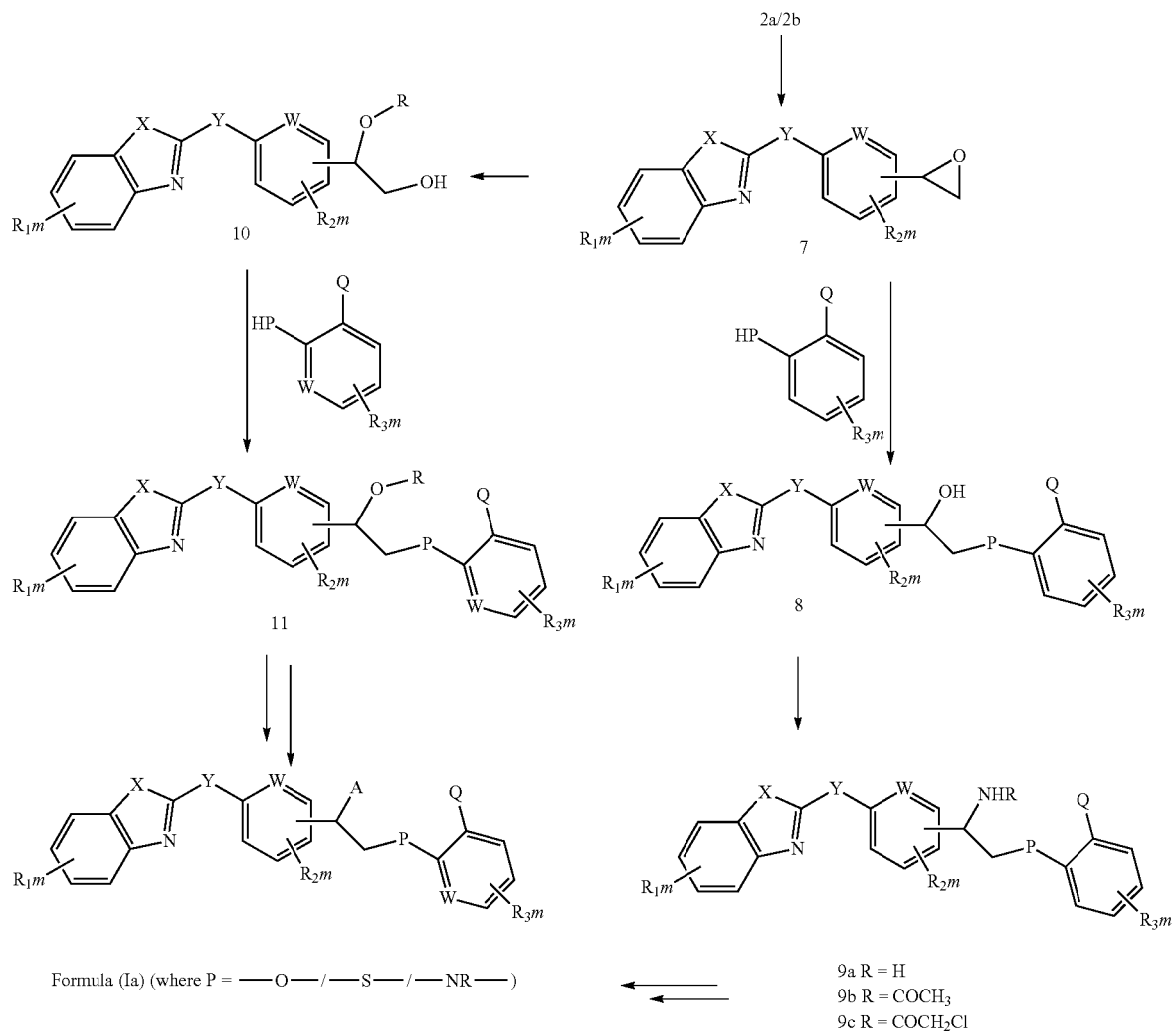

Scheme-2

Formula (Ia) (where P = —O—/—S—/—NR—)

9a R = H
9b R = COCH$_3$
9c R = COCH$_2$Cl

In another embodiment (Scheme 2), aldehydes such as 2a/b derived from substituted or unsubstituted quinaldines/benz[c]thiazoles/quinoxalines (M. Labelle et. al., Bio. Org. Med. Chem. Lett., 1994, 4, 463 or M. Labelle et. al., ibid, 1995, 5, 293) were treated with trialkylsulfoxonium salt/trialkylsulfonium salts to form the epoxides 7 under Corey-Chaykovsky (E. J Corey et. al., *J. Am. Chem. Soc.,* 87, 1353, 1965 and E. J. Corey et. al., *Org. synth.,* 49, 78, 1969) conditions.

Achiral/chiral epoxides 7 were opened under basic condition with nucleophiles derived from phenols/thiophenols (FIG. 2) gave alcohol such as 8 which in-turn were converted to the amines such as 9c in few steps, namely halogenation-azidation-reduction sequence as in Staudinger reaction condition. Alternatively some of the alcohols were converted to the acylamides under Ritter conditions as described earlier. Achiral/chiral epoxides 7 can also be opened under mild acidic/Lewis acidic conditions in presence of various alcohols such as methanol, ethanol, isopropanol pheneethyl alcohol, allyl alcohol, propargyl alcohol, cyclohexanol, cyclopropyl methanol etc. (FIG. 4) to generate beta alkoxy-alcohols such as 10 which upon Mitsunobu reaction (O. Mitsunobu, *Synthesis* 1981, 1 and S. D. Lepore and Y. He, J. Org. Chem., 68, 8261, 2003) with various phenols/thiophenol (selected from FIG. 2) gave compounds such as 11. On basic hydrolysis few compounds may result in either racemic/chiral derivatives of interest as represented in formula (Ia).

FIG. 4

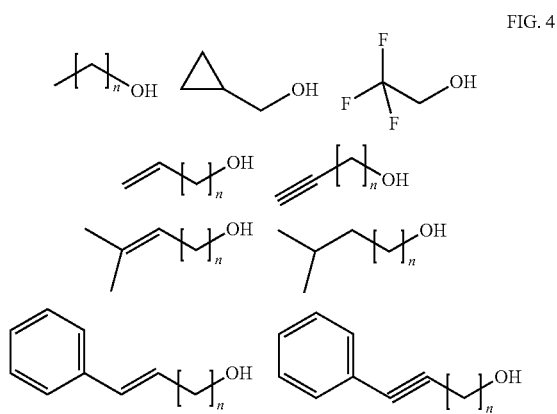

-continued

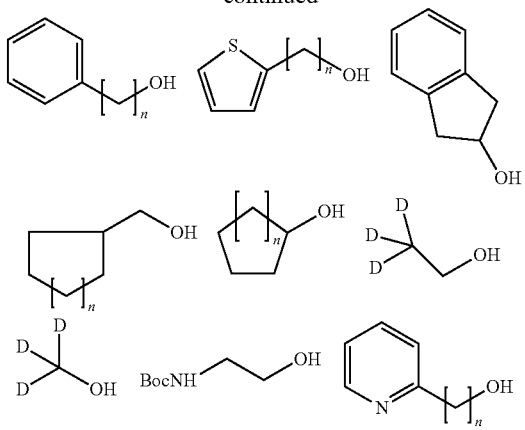

The current invention is not limited to the examples mentioned in the following tables but involves several substituted quinaldines, thiazoles and quinoxaline chromophores such as Quinaldine, 7-chloroquinaldine, 7-fluoroquinaldine, 6-fluoroquinaldine, 7-methoxy-quinaldine, 6,7-dichloroquinalidine, 7,8-dichloroquinaldine, 7-chloro-6-fluoroquinaldine, 6,7-difluoroquinaldine, 2-methyl benzo[c]thiazole, 6-chloro-2-methyl benzo[c]thiazole, 2-methyl-quinoxaline and 7-chloro-2-methylquinoxaline etc.

Oximes 12 and oxime-ethers 13 were also prepared from the keto compound 4 under usual reaction conditions. In yet another embodiment keto compounds such as 4 or 8a were treated with trialkylortho-formate in alcohol/glycols/thioglycols in presence of catalytic acid such as mineral acid, paratoluene sulphonic acid (PTSA), camphor sulphonic acid (CSA), solid acid catalysts such as amberlyst-H+, other resin acids or clays to generate open or cyclic ketals 14 and 15 as shown in Scheme 3 (where U and V represent heteroatoms such as —O—, —S— or —NR—.). Further the Ketals containing ester moieties were hydrolysed under usual basic condition to generate the acid or its derivatives as described in formula (Ib) (see table 2). Some of the prodrugs of the acids were also synthesized and tested for desired activity

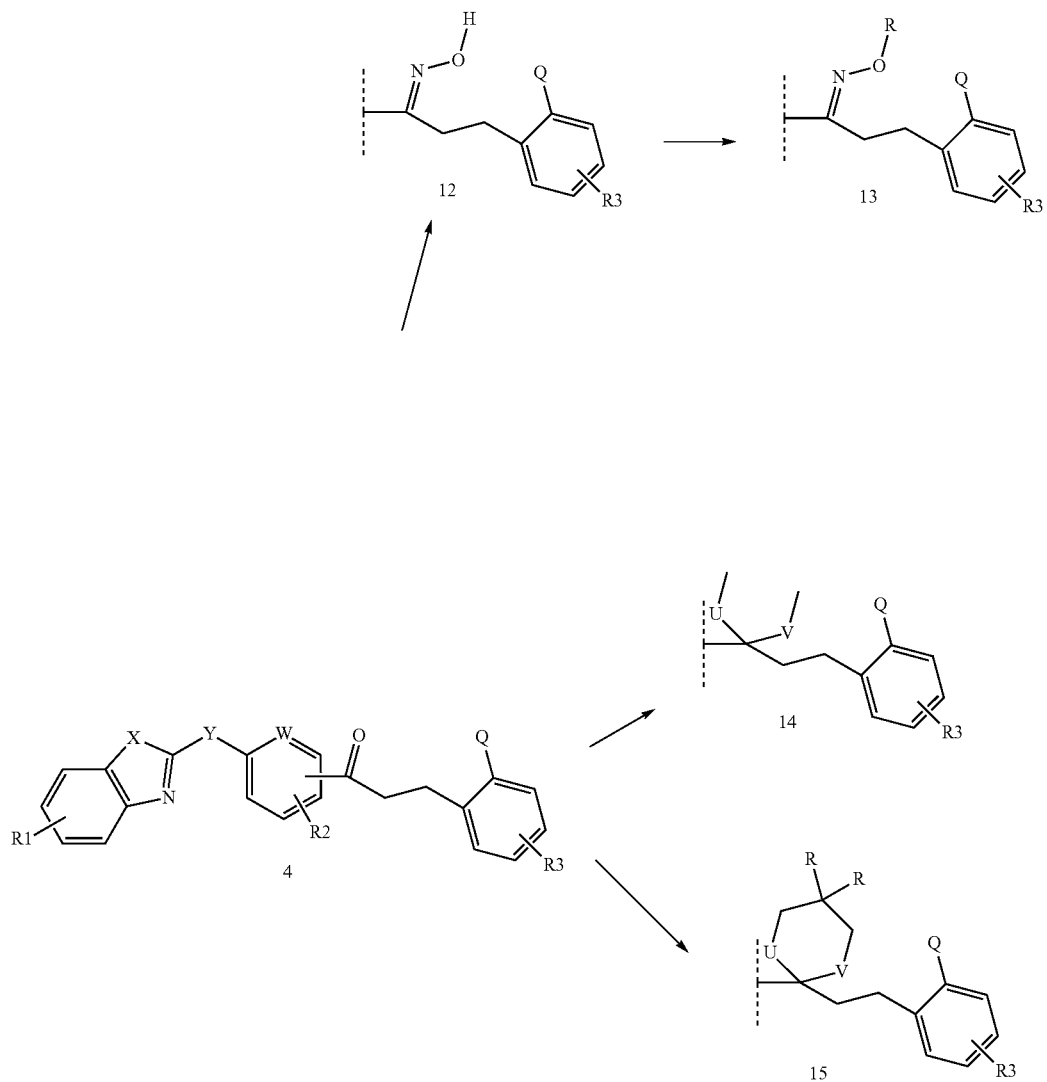

Scheme-3

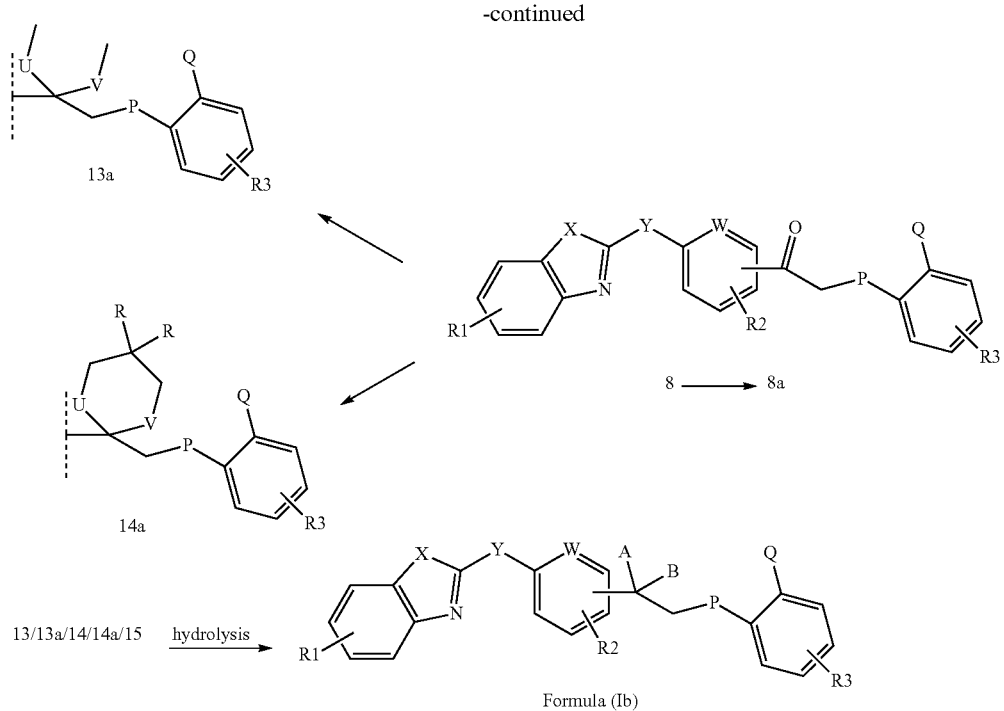
In an extension as in scheme 4 the ether-alcohols 10 can be treated with aliphatic bromo-esters under basic conditions to 16 followed by ester hydrolysis gave some of the compounds depicted in formula (Ic) (presented in table 2).
Scheme-4
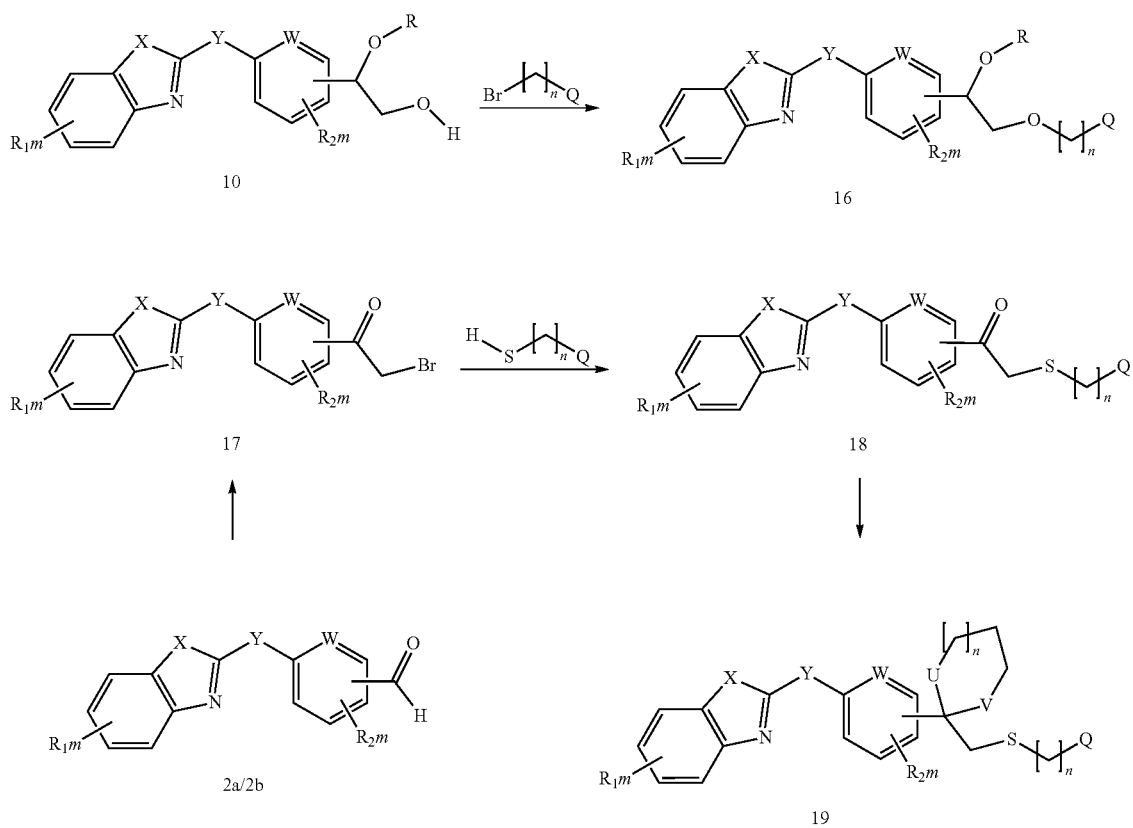

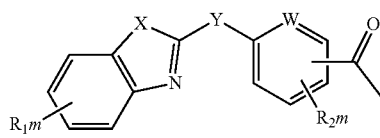

3 → 3a

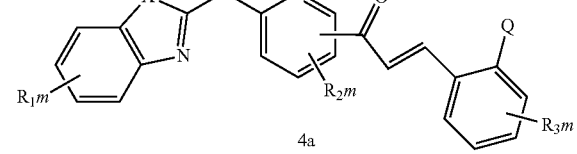

4a

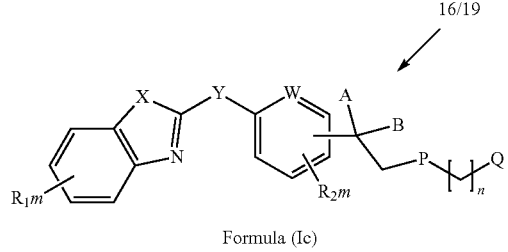

Formula (Ic)

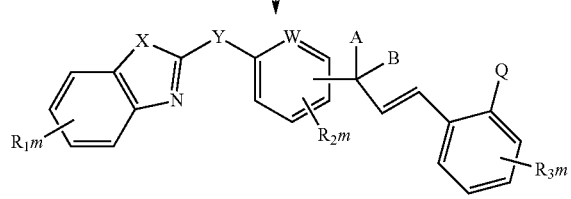

Formula (Ib)

Aldehydes 2a/2b are converted to keto-halide 17 in few steps and then treated with various aliphatic thiol-esters and the obtained structure 18, which on ketalization gave ketal-ester 19. Hydrolysis of ester 19 under usual basic condition resulted in some of the aliphatic compounds of interest as described in either formula (Ic). Similarly some of the ketal derivatives of formula (Ib) are derived from the chalcone 4a obtained from allyl-alcohol 3 by oxidation to 3a and coupling with halo-arenes described in FIG. 3.

The compounds of the present invention can be exemplified by the following non-limiting examples:

TABLE 1

Compounds of Formula (Ia)

| S. No. | Name | Sign of rotation | Mass Analysis |
|---|---|---|---|
| Ia.01 | 2-(3-Acetylamino-3-{3-[(E)-2-(7-chloro-quinolin-2-yl)-vinyl]-phenyl}-propyl)-benzoic acid | ± | 484 (M; 4%)# |
| Ia.02 | 2-(3-[2-(1-Carboxymethyl-cyclopropyl-methyl-sulfanyl)-acetylamino]-3-{3-[(E)-2-(7-chloro quinolin-2-yl)-vinyl]-phenyl}-propyl)-benzoic acid | ± | 629.12 (M + H) |
| Ia.03 | 2-(3-[2-(2-Carboxyethylsulfanyl)acetylamino]-3-{3-[(E)-2-(7-chloro-quinolin-2-yl)-vinyl]-phenyl}-propyl)-benzoic acid methyl ester | ± | 603.1 (M + H) |
| Ia.04 | 2-(3-(3-Carboxy-propionylamino)-3-{3-[(E)-2-(7-chloro-quinolin-2-yl)-vinyl]-phenyl}-propyl)-benzoic acid | ± | 543.11 (M + H) |
| Ia.05 | 2-(3-(3-Carboxy-acryloylamino)-3-{3-[(E)-2-(7-chloro-quinolin-2-yl)-vinyl]-phenyl}-propyl)-benzoic acid | ± | 541.11 (M + H) |
| Ia.06 | 2-{3-{3-[(E)-2-(7-Chloro-quinolin-2-yl)-vinyl]-phenyl}-3-[2-(2-carboxy-phenyl)-acetylamino]-propyl}-benzoic acid | ± | 605.11 (M + H) |
| Ia.07 | 2-[3-{3-[(E)-2-(7-Chloro-quinolin-2-yl)-vinyl]-phenyl}-3-(2-carboxy-benzoylamino)-propyl]-benzoic acid | ± | 591.07 (M + H) |
| Ia.08 | 2-(3-[(1-Carboxycyclopropanecarbonyl)amino]-3-{3-[(E)-2-(7-chloro-quinolin-2-yl)-vinyl]-phenyl}-propyl)-benzoic acid | ± | 555.12 (M + H) |
| Ia.09 | 2-(3-{3-[(E)-2-(7-Chloro-quinolin-2-yl)-vinyl]-phenyl}-3-hexanoylamino-propyl)-benzoic acid | ± | 541.21 (M + H) |
| Ia.10 | 2-(3-Benzenesulfonylamino-3-{3-[(E)-2-(7-chloro-quinolin-2-yl)vinyl]-phenyl}-propyl)-benzoic acid | ± | 581 (M; 1.7%)# |
| Ia.11 | 2-(3-{3-[(E)-2-(7-Chloro-quinolin-2-yl)-vinyl]phenyl}-3-methanesulfonylamino-propyl)-benzoic acid | ± | 520 (M; 3%)# |
| Ia.12 | 2-[3-{3-[(E)-2-(7-Chloro-quinolin-2-yl)-vinyl]-phenyl}-3-(2,2,2-trifluoro-acetylamino)-propyl]-benzoic acid | ± | 538 (M; 21%)# |
| Ia.13 | 2-(3-tert-Butoxycarbonylamino-3-{3-[(E)-2-(7-chloro-quinolin-2-yl)-vinyl]-phenyl}-propyl)-benzoic acid | ± | 542 (M; 4%)# |
| Ia.14 | 2-{3-{3-[(E)-2-(7-Chloro-quinolin-2-yl)-vinyl]-phenyl}-3-[2-(2-carboxy-phenoxy)-acetylamino]-propyl}-benzoic acid | ± | 621.12 (M + H) |
| Ia.15 | 2-[3-{3-[(E)-2-(7-Chloroquinolin-2-yl)vinyl]-phenyl}-3-(ethoxyhydroxy-phosphorylamino)-propyl]-benzoic acid | ± | 551.36 (M + H) |

TABLE 1-continued

Compounds of Formula (Ia)

| S. No. | Name | Sign of rotation | Mass Analysis |
|---|---|---|---|
| Ia.16 | 2-[3-{3-[(E)-2-(7-Chloro-quinolin-2-yl)-vinyl]-phenyl}-3-(2-morpholin-4-yl-acetylamino)-propyl]-benzoic acid | ± | 570.20 (M + H) |
| Ia.17 | 2-[3-{3-[(E)-2-(7-Chloro-quinolin-2-yl)-vinyl]-phenyl}-3-(2-diethylamino-acetylamino)-propyl]-benzoic acid | ± | 556.25 (M + H) |
| Ia.18 | 2-[3-{3-[(E)-2-(7-Chloro-quinolin-2-yl)-vinyl]-phenyl}-3-(cyclopropanecarbonyl-amino)-propyl]-benzoic acid | ± | 511.03 (M + H) |
| Ia.19 | 2-[3-{3-[(E)-2-(7-Chloro-quinolin-2-yl)-vinyl]-phenyl}-3-(cyclopentanecarbonyl-amino)-propyl]-benzoic acid | ± | 539.08 (M + H) |
| Ia.20 | 2-(3-{3-[(E)-2-(7-Chloro-quinolin-2-yl)-vinyl]-phenyl}-3-methoxycarbonylamino-propyl)-benzoic acid | ± | 500 (M; 13%)# |
| Ia.21 | 2-[3-{3-[(E)-2-(7-Chloro-quinolin-2-yl)-vinyl]-phenyl}-3-(cyclobutanecarbonyl-amino)-propyl]-benzoic acid | ± | 524 (M; 1.3%)# |
| Ia.22 | 2-(3-{3-[(E)-2-(7-Chloro-quinolin-2-yl)-vinyl]-phenyl}-3-propionylamino-propyl)-benzoic acid | ± | 498 (M; 4.3%)# |
| Ia.23 | 2-[3-{3-[(E)-2-(7-Chloro-quinolin-2-yl)-vinyl]-phenyl}-3-(cyclohexanecarbonyl-amino)-propyl]-benzoic acid | ± | 553.24 (M + H) |
| Ia.24 | 2-[3-{3-[(E)-2-(7-Chloro-quinolin-2-yl)-vinyl]-phenyl}-3-(2,2-dimethyl-propionylamino)-propyl]-benzoic acid | ± | 526 (M; 1.8%)# |
| Ia.25 | 2-(3-{3-[(E)-2-(7-Chloro-quinolin-2-yl)-vinyl]-phenyl}-3-phenylacetylamino-propyl)-benzoic acid | ± | 5.60 (M; <1%)# |
| Ia.26 | 2-(3-{3-[(E)-2-(7-Chloro-quinolin-2-yl)-vinyl]-phenyl}-3-ethoxycarbonylamino-propyl)-benzoic acid | ± | 515.16 (M + H) |
| Ia.27 | 2-(3-{3-[(E)-2-(7-Chloro-quinolin-2-yl)-vinyl]-phenyl}-3-formylamino-propyl)-benzoic acid | ± | 470 (M; 5%)# |
| Ia.28 | 2-{3-{3-[(E)-2-(7-Chloro-quinolin-2-yl)-vinyl]-phenyl}-3-[(thiophene-2-carbonyl)-amino]-propyl}-benzoic acid | ± | 553.13 (M + H) |
| Ia.29 | 2-{3-{3-[(E)-2-(7-Chloro-quinolin-2-yl)-vinyl]-phenyl}-3-[(furan-2-carbonyl)-amino]-propyl}-benzoic acid | ± | 537.14 (M + H) |
| Ia.30 | 2-[3-{3-[(E)-2-(7-Chloro-quinolin-2-yl)-vinyl]-phenyl}-3-(4-fluoro-benzoylamino)-propyl]-benzoic acid | ± | 565.17 (M + H) |
| Ia.31 | 2-[3-{3-[(E)-2-(7-Chloro-quinolin-2-yl)-vinyl]-phenyl}-3-(3-phenyl-ureido)-propyl]-benzoic acid | ± | 562.07 (M + H) |
| Ia.32 | 2-(3-{3-[(E)-2-(7-Chloro-quinolin-2-yl)-vinyl]-phenyl}-3-pyrrol-1-yl-propyl)-benzoic acid | ± | 492 (M; 24%)# |
| Ia.33 | 2-(2-Acetylamino-2-{3-[(E)-2-(7-chloro-quinolin-2-yl)-vinyl]-phenyl}-ethoxy)-benzoic acid | ± | 487.35 (M + H) |
| Ia.34 | 2-(3-Benzoylamino-3-{3-[(E)-2-(7-chloro-quinolin-2-yl)-vinyl]-phenyl}-propyl)-benzoic acid | ± | 547.24 (M + H) |
| Ia.35 | 2-{3-{3-[(E)-2-(7-Chloro-quinolin-2-yl)-vinyl]-phenyl}-3-[(pyridine-3-carbonyl)-amino]-propyl}-benzoic acid | ± | 548.23 (M + H) |
| Ia.36 | 2-{[1-{3-[(E)-2-(7-Chloro-quinolin-2-yl)-vinyl]-phenyl}-3-(2-diethylcarbamoyl-phenyl)-propyl-carbamoyl]-methyl}-benzoic acid | ± | 660.30 (M + H) |
| Ia.37 | N-[1-{3-[(E)-2-(7-Chloro-quinolin-2-yl)-vinyl]-phenyl}-3-(2-diethylcarbamoyl-phenyl)-propyl]-succinamic acid | ± | 598.31 (M + H) |
| Ia.38 | N-[1-{3-[(E)-2-(7-Chloro-quinolin-2-yl)-vinyl]-phenyl}-3-(2-diethylcarbamoyl-phenyl)-propyl]-phthalamic acid | ± | 646.24 (M + H) |
| Ia.39 | 4-(3-Acetylamino-3-{3-[(E)-2-(7-chloro-quinolin-2-yl)-vinyl]-phenyl}-propyl)-benzoic acid | ± | 486 (M + 1; 11%)# |
| Ia.40 | N-[1-{3-[(E)-2-(7-Chloro-quinolin-2-yl)-vinyl]-phenyl}-3-(2-ethylcarbamoyl-phenyl)-propyl]-succinamic acid | ± | 570.21 (M + H) |
| Ia.41 | 2-{[1-{3-[(E)-2-(7-Chloro-quinolin-2-yl)-vinyl]-phenyl}-3-(2-ethylcarbamoyl-phenyl)-propyl-carbamoyl]-methyl}-benzoic acid | ± | 632.22 (M + H) |
| Ia.42 | N-{1-{3-[(E)-2-(7-Chloro-quinolin-2-yl)-vinyl]-phenyl}-3-[2-(1-hydroxy-1-methyl-ethyl)-phenyl]-propyl}-succinamic acid | ± | 557.21 (M + H) |
| Ia.43 | N-{1-{3-[(E)-2(7Chloroquinolin-2yl)vinyl] phenyl}-3-[2-(1-hydroxy-1-methyl-ethyl)-phenyl]-propyl}-phthalamic acid | ± | 605.20 (M + H) |

TABLE 1-continued

Compounds of Formula (Ia)

| S. No. | Name | Sign of rotation | Mass Analysis |
|---|---|---|---|
| Ia.44 | Thiophene-2-carboxylic acid {1-{3-[(E)-2-(7-chloro-quinolin-2-yl)-vinyl]-phenyl}-3-[2-(1-hydroxy-1-methyl-ethyl)-phenyl]-propyl}-amide | ± | 567.22 (M + H) |
| Ia.45 | 2-({1-{3-[(E)-2-(7-Chloro-quinolin-2-yl)-vinyl]-phenyl}-3-[2-(1-hydroxy-1-methyl-ethyl)-phenyl]-propylcarbamoyl}-methyl)-benzoic acid | ± | 619.22 (M + H) |
| Ia.46 | 2-(3-Benzoylamino-3-{3-[(E)-2-(7-chloro-quinolin-2-yl)-vinyl]-phenyl}-propyl)-N-ethyl-benzamide | ± | 574.44 (M + H) |
| Ia.47 | 2-(3-{3-[(E)-2-(7-Chloro-quinolin-2-yl)-vinyl]-phenyl}-3-phenylacletylamino-propyl)-N-ethyl-benzamide | ± | 588.50 (M + H) |
| Ia.48 | N-[1-{3-[(E)-2-(7-Chloro-quinolin-2-yl)-vinyl]-phenyl}-3-(2-diethylcarbamoyl-phenyl)-propyl]-phthalamic acid methyl ester | ± | 660.45 (M + H) |
| Ia.49 | 2-(3-{3-[(E)-2-(7-Chloro-quinolin-2-yl)-vinyl]-phenyl}-3-dioctylamino-propyl)-benzoic acid | ± | 667.59 (M + H) |
| Ia.50 | 2-(3-Acetylamino-3-{4-[(E)-2-(7-chloro-quinolin-2-yl)-vinyl]-phenyl}-propyl)-benzoic acid | ± | 484.43 (M + H) |
| Ia.51 | 4-{1-{3-[(E)-2-(7-Chloro-quinolin-2-yl)-vinyl]-phenyl}-3-[2-(1-hydroxy-1-methyl-ethyl)-phenyl]-propylcarbamoyl}-butyric acid | ± | 571.47 (M + H) |
| Ia.52 | 2-[3-{3-[(E)-2-(7-Chloro-quinolin-2-yl)-vinyl]-phenyl}-3-(2-hydroxy-2-methyl-propylamino)-propyl]-benzoic acid | ± | 515.51 (M + H) |
| Ia.53 | 2-{(R)-3-{3-[(E)-2-(7-Chloro-quinolin-2-yl)-vinyl]-phenyl}-3-[(thiophene-2-carbonyl)-amino]-propyl}-benzoic acid | + | 553.47 (M + H) |
| Ia.54 | 2-{(R)-3-{3-[(E)-2-(7-Chloro-quinolin-2-yl)-vinyl]-phenyl}-3-[(furan-2-carbonyl)-amino]-propyl}-benzoic acid | − | 537.47 (M + H) |
| Ia.55 | N-[1-{3-[(E)-2-(7-Chloro-quinolin-2-yl)-vinyl]-phenyl}-3-(2-diethylcarbamoyl-phenyl)-propyl]-phthalamic acid ethyl ester | ± | 674.60 (M + H) |
| Ia.56 | N-[(R)-1-{3-[(E)-2-(7-Chloro-quinolin-2-yl)-vinyl]-phenyl}-3-(2-diethylcarbamoyl-phenyl)-propyl]-phthalamic acid | + | 646.59 (M + H) |
| Ia.57 | [1-({1-{3-[(E)-2-(7-Chloro-quinolin-2-yl)-vinyl]-phenyl}-3-[2-(1-hydroxy-1-methyl-ethyl)-phenyl]-propylcarbamoyl}-methyl)-cyclohexyl]-acetic acid | ± | 639.62 (M + H) |
| Ia.58 | 4,5-Dichloro-N-{1-{3-[(E)-2-(7-chloro-quinolin-2-yl)-vinyl]-phenyl}-3-[2-(1-tiydroxy-1-methyl-ethyl)-phenyl]-propyl}-phthalamic acid | ± | 675.47 (M + H) |
| Ia.59 | 2-{1-{3-[(E)-2-(7-Chloro-quinolin-2-yl)-vinyl]-phenyl}-3-[2-(1-hydroxy-1-methyl-ethyl)-phenyl]-propylcarbamoyl}-benzenesulfonic acid | ± | 641.55 (M + H) |
| Ia.60 | ({1-{3-[(E)-2-(7-Chloro-quinolin-2-yl)-vinyl]-phenyl}-3-[2-(1-hydroxy-1-methyl-ethyl)-phenyl]-propylcarbamoyl}-methoxy)-acetic acid | ± | 573.50 (M + H) |
| Ia.61 | N-{1-{3-[(E)-2-(7-Chloro-quinolin-2-yl)-vinyl]-phenyl}-3-[2-(1-hydroxy-1-methyl-ethyl)-phenyl]-propyl}-2-hydroxy-benzamide | ± | 577.53 (M + H) |
| Ia.62 | 2-(3-{3-[(E)-2-(7-Chloro-quinolin-2-yl)-vinyl]-phenyl}-3-piperidin-1-yl-propyl)-benzoic acid | ± | 511.50 (M + H) |
| Ia.63 | 1-(3-(2-Carboxy-phenyl)-1-{3-[(E)-2-(7-chloro-quinolin-2-yl)-vinyl]-phenyl}propyl)piperidine-4-carboxylic acid | ± | 555.52 (M + H) |
| Ia.64 | 3-({1-{3-[(E)-2-(7-Chloro-quinolin-2-yl)-vinyl]-phenyl}-3-[2-(1-hydroxy-1-methyl-ethyl)-phenyl]-propylcarbamoyl}-methylsulfanyl)-propionic acid | ± | 589.09 (M + H) |
| Ia.65 | 2-({1-{3-[(E)-2-(7-Chloro-quinolin-2-yl)-vinyl]-phenyl}-3-[2-(1-hydroxy-1-methyl-ethyl)-phenyl]-propylcarbamoyl}-methylsulfanyl)-benzoic acid | ± | 651.10 (M + H) |
| Ia.66 | 2-{(S)-{3-{3-[(E)-2-(7-Chloro-quinolin-2-yl)-vinyl]-phenyl}-3-[(furan-2-carbonyl)-amino]-propyl}-benzoic acid | + | 537.08 (M + H) |
| Ia.67 | N-[(S)-1-{3-[(E)-2-(7-Chloro-quinolin-2-yl)-vinyl]-phenyl}-3-(2-diethylcarbamoyl-phenyl)-propyl]-phthalamic acid | − | 646.18 (M + H) |
| Ia.68 | N-[(S)-1-{3-[(E)-2-(7-Chloro-quinolin-2-yl)-vinyl]-phenyl}-3-(2-diethylcarbamoyl-phenyl)-propyl]-phthalamic acid methyl ester | − | 660.20 (M + H) |
| Ia.69 | 2-{(S)-3-{3-[(E)-2-(7-Chloro-quinolin-2-yl)-vinyl]-phenyl}-3-[(thiophene-2-carbonyl)-amino]-propyl}-benzoic acid | − | 553.07 (M + H) |

TABLE 1-continued

Compounds of Formula (Ia)

| S. No. | Name | Sign of rotation | Mass Analysis |
|---|---|---|---|
| Ia.70 | N-[(R)-1-{3-[(E)-2-(7-Chloro-quinolin-2-yl)-vinyl]-phenyl}-3-(2-diethylcarbamoyl-phenyl)-propyl]-phthalamic acid methyl ester | + | 660.20 (M + H) |
| Ia.71 | 2-(2-{1-{3-[(E)-2-(7-Chloro-quinolin-2-yl)-vinyl]-phenyl}-3-[2-(1-hydroxy-1-methyl-ethyl)-phenyl]-propylcarbamoyl}-vinyl)-benzoic acid methyl ester | ± | 645.16 (M + H) |
| Ia.72 | N-{1-{3-[(E)-2-(7-Chloro-quinolin-2-yl)-vinyl]-phenyl}-3-[2-(2-hydroxy-2-methyl-propoxy)-phenyl]-propyl}-phthalamic acid | ± | 635.15 (M + H) |
| Ia.73 | N-{1-{3-[(E)-2-(7-Chloro-quinolin-2-yl)-vinyl]-phenyl}-3-[2-(pyrrolidine-1-carbonyl)-phenyl]-propyl}-phthalamic acid | ± | 644.17 (M + H) |
| Ia.74 | Furan-2-carboxylic acid {1-{3-[(E)-2-(7-chloro-quinolin-2-yl)-vinyl]-phenyl}-3-[2-(pyrrolidine-1-carbonyl)-phenyl]-propyl}-amide | ± | 590.10 (M + H) |
| Ia.75 | N-[1-{3-[(E)-2-(7-Chloro-quinolin-2-yl)-vinyl]-phenyl}-3-(2-diethylcarbamoyl-phenyl)-propyl]-N-methyl-phthalamic acid | ± | 660.20 (M + H) |
| Ia.76 | 2-{3-{3-[(E)-2-(7-Chloro-quinolin-2-yl)-vinyl]-phenyl}-3-[(furan-2-carbonyl)-methyl-amino]-propyl}-benzoic acid | ± | 551.26 (M + H) |
| Ia.77 | 2-[3-{3-[(E)-2-(7-Chloro-quinolin-2-yl)-vinyl]-phenyl}-3-(2-carboxy-benzylamino)-propyl]-benzoic acid methyl ester | ± | 573.14 (M + H − 18) |
| Ia.78 | 2-[3-{3-[(E)-2-(7-Chloro-quinolin-2-yl)-vinyl]-phenyl}-3-(2-carboxy-benzylamino)-propyl]-benzoic acid | ± | 559.13 (M + 1 − 18) |
| Ia.79 | 2-(3-[(2-Carboxy-cyclohex-1-enecarbonyl)-amino]-3-{3-[(E)-2-(7-chloro-quinolin-2-yl)-vinyl]-phenyl}-propyl)-benzoic acid methyl ester | ± | 609.10 (M + H) |
| Ia.80 | 2-(3-[(2-Carboxy-cyclopent-1-enecarbonyl)-amino]-3-{3-[(E)-2-(7-chloro-quinolin-2-yl)-vinyl]-phenyl}-propyl)-benzoic acid methyl ester | ± | 595.24 (M + H) |
| Ia.81 | 2-(3-(3-Carboxy-3-phenyl-acryloylamino)-3-{3-[(E)-2-(7-chloro-quinolin-2-yl)-vinyl]-phenyl}-propyl)-benzoic acid methyl ester | ± | 631.22 (M + H) |
| Ia.82 | 2-(3-(3-Carboxy-2,3-diphenyl-acryloylamino)-3-{3-[(E)-2-(7-chloro-quinolin-2-yl)-vinyl]-phenyl}-propyl)-benzoic acid methyl ester | ± | 707.27 (M + H) |
| Ia.83 | Furan-2-carboxylic acid [1-{3-[(E)-2-(7-chloro-quinolin-2-yl)-vinyl]-phenyl}-3-(2-diethyl-carbamoyl-phenyl)-propyl]-methyl-amide | ± | 606.15 (M + H) |
| Ia.84 | 2-[3-{3-[(E)-2-(7-Chloro-quinolin-2-yl)-vinyl]-phenyl}-3-(1,3-dihydro-isoindol-2-yl)-propyl]-benzoic acid | ± | 545.14 (M + H) |
| Ia.85 | 2-[3-{3-[(E)-2-(7-Chloro-quinolin-2-yl)-vinyl]-phenyl}-3-(1-oxo-1,3-dihydro-isoindol-2-yl)-propyl]-N,N-diethyl-benzamide | ± | 614.34 (M + H) |
| Ia.86 | 2-{1-{3-[(E)-2-(7-Chloro-quinolin-2-yl)-vinyl]-phenyl}-3-[2-(1-hydroxy-1-methyl-ethyl)-phenyl]-propyl}-2,3-dihydro-isoindol-1-one | ± | 573.31 (M + H) |
| Ia.87 | 2-(2-Acetylamino-2-{3-[(E)-2-(7-chloro-quinolin-2-yl)-vinyl]-phenyl}-ethylsulfanyl)-benzoic acid | ± | 503.32 (M + H) |
| Ia.88 | 2-(2-{3-[(E)-2-(7-Chloro-quinolin-2-yl)-vinyl]-phenyl}-2-methoxy-ethoxy)-benzoic acid | ± | 460.34 (M + H) |
| Ia.89 | N-[2-(2-{3-[(E)-2-(7-Chloro-quinolin-2-yl)-vinyl]-phenyl}-2-methoxy-ethoxy)-phenyl]-succinamic acid | ± | 531.39 (M + H) |
| Ia.90 | 3-[2-(2-{3-[(E)-2-(7-Chloro-quinolin-2-yl)-vinyl]-phenyl}-2-methoxy-ethoxy)-phenylcarbamoyl]-acrylic acid | ± | 529.34 (M + H) |
| Ia.91 | 2-(3-{3-[(E)-2-(7-Chloro-quinolin-2-yl)-vinyl]-phenyl}-3-[1,2,4]triazol-1-yl-propyl)-benzoic acid | ± | 494.98 (M + H) |
| Ia.92 | 2-(2-{3-[(E)-2-(7-Chloro-quinolin-2-yl)-vinyl]-phenyl}-2-ethoxy-ethoxy)-5-dimethylamino-benzoic acid | ± | 517.04 (M + H) |
| Ia.93 | 2-(2-{3-[(E)-2-(7-Chloro-quinolin-2-yl)-vinyl]-phenyl}-2-ethoxy-ethoxy)-benzoic acid | ± | 474.11 (M + H) |
| Ia.94 | 2-(2-{3-[(E)-2-(7-Chloro-quiolin-2-yl)-vinyl]-phenyl}-2-isopropoxy-ethoxy)-benzoic acid | ± | 488.37 (M + H) |
| Ia.95 | 2-(2-Butoxy-2-{3-[(E)-2-(7-chloro-quinolin-2-yl)-vinyl]-phenyl}-ethoxy)-benzoic acid | ± | 502.38 (M + H) |
| Ia.96 | 2-(2-{3-[(E)-2-(7-Chloro-quinolin-2-yl)-vinyl]-phenyl}-2-cyclopropylmethoxy-ethoxy)-benzoic acid | ± | 500.36 (M + H) |

TABLE 1-continued

Compounds of Formula (Ia)

| S. No. | Name | Sign of rotation | Mass Analysis |
|---|---|---|---|
| Ia.97 | 2-[2-{3-[(E)-2-(7-Chloro-quinolin-2-yl)-vinyl]-phenyl}-2-(2,2,2-trifluoro-ethoxy)-ethoxy]-benzoic acid | ± | 528.09 (M + H) |
| Ia.98 | 2-(2-Allyloxy-2-{3-[(E)-2-(7-chloro-quinolin-2-yl)-vinyl]-phenyl}-ethoxy)-benzoic acid | ± | 486.31 (M + H) |
| Ia.99 | 2-(2-Acetylamino-2-{3-[(E)-2-(7-chloro-quinolin-2-yl)-vinyl]-phenyl}-ethoxy)-benzoic acid | ± | 487.35 (M + H) |
| Ia.100 | 2-(2-Cyclopropylmethoxy-2-{3-[(E)-2-(6,7-difluoro-quinolin-2-yl)-vinyl]-phenyl}-ethoxy)-5-methoxy-benzoic acid | ± | 532.19 (M + H) |
| Ia.101 | 3-[2-(2-{3-[(E)-2-(7-Chloro-quinolin-2-yl)-vinyl]-phenyl}-2-methoxy-ethoxy)-phenyl]-acrylic acid | ± | 486.36 (M + H) |
| Ia.102 | 5-Chloro-2-(2-{3-[(E)-2-(7-chloro-quinolin-2-yl)-vinyl]-phenyl}-2-methoxy-ethoxy)-benzoic acid | ± | 494.31 (M + H) |
| Ia.103 | 2-(2-{4-[(E)-2-(7-Chloro-quinolin-2-yl)-vinyl]-phenyl}-2-ethoxy-ethoxy)-benzoic acid | ± | 474.07 (M + H) |
| Ia.104 | 2-(2-Allyloxy-2-{4-[(E)-2-(7-chloro-quinolin-2-yl)-vinyl]-phenyl}-ethoxy)-benzoic acid | ± | 486.35 (M + H) |
| Ia.105 | N-{1-{3-[(E)-2-(7-Chloro-quinolin-2-yl)-vinyl]-phenyl}-2-[2-(1-hydroxy-1-methyl-ethyl)-phenoxy]-ethyl}-phthalamic acid | ± | 607.38 (M + H) |
| Ia.106 | (1-{1-{3-[(E)-2-(7-Chloro-quinolin-2-yl)-vinyl]-phenyl}-2-[2-(1-hydroxy-1-methyl-ethyl)-phenoxy]-ethylsulfanylmethyl}-cyclopropyl)-acetic acid | ± | 635.17 (M + H) |
| Ia.107 | 2-(2-{3-[(E)-2-(7-Chloro-quinolin-2-yl)-vinyl]-phenyl}-2-methoxy-ethylsulfanyl)-benzoic acid | ± | 476.30 (M + H) |
| Ia.108 | {1-{3-[(E)-2-(7-Chloro-quinolin-2-yl)-vinyl]-phenyl}-2-[2-(1-hydroxy-1-methyl-ethyl)-phenoxy]-ethylsulfanyl}-acetic acid | ± | 516.11 (M + H) |
| Ia.109 | 2-{1-{3-[(E)-2-(7-Chloro-quinolin-2-yl)-vinyl]-phenyl}-2-[2-(1-hydroxy-1-methyl-ethyl)-phenoxy]-ethylcarbamoyl}-cyclopent-1-enecarboxylic acid | ± | 597.38 (M + H) |
| Ia.110 | 2-[2-{3-[(E)-2-(7-Chloro-quinolin-2-yl)-vinyl]-phenyl}-2-(2-carboxy-benzoylamino)-ethylsulfanyl]-benzoic acid methyl ester | ± | 623.30 (M + H) |
| Ia.111 | 2-{2-{3-[(E)-2-(7-Chloro-quinolin-2-yl)-vinyl]-phenyl}-2-[(furan-2-carbonyl)-amino]-ethylsulfanyl}-benzoic acid | ± | 555.10 (M + H) |
| Ia.112 | 2-(2-[(2-Carboxy-cyclohex-1-enecarbonyl)-amino]-2-{3-[2-(7-chloro-quinolin-2-yl)-vinyl]-phenyl}-ethylsulfanyl)-benzoic acid methyl ester | ± | 627.37 (M + H) |
| Ia.113 | 2-{2-{3-[(E)-2-(7-Chloro-quinolin-2-yl)-vinyl]-phenyl}-2-[(thiophene-2-carbonyl)-amino]-ethylsulfanyl}-benzoic acid | ± | 571.30 (M + H) |
| Ia.114 | 2-(2-[(2-Carboxy-cyclopent-1-enecarbonyl)-amino]-2-{3-[(E)-2-(7-chloro-quinolin-2-yl)-vinyl]-phenyl}-ethylsulfanyl)-benzoic acid | ± | 599.11 (M + H) |
| Ia.115 | 2-(2-{3-[(E)-2-(7-Chloro-quinolin-2-yl)-vinyl]-phenyl}-2-ethoxy-ethylsulfanyl)-benzoic acid | ± | 490.33 (M + H) |
| Ia.116 | 2-(2-tert-Butyl-phenoxy)-1-{3-[(E)-2-(7-chloro-quinolin-2-yl)-vinyl]-phenyl}-ethanol | ± | 460.40 (M + H) |
| Ia.117 | 2-(2-tert-Butyl-phenylsulfanyl)-1-{3-[(E)-2-(7-chloro-quinolin-2-yl)-vinyl]-phenyl}-ethanol | ± | 476.37 (M + H) |
| Ia.118 | 2-(2-Acetoxy-2-{3-[(E)-2-(7-chloro-quinolin-2-yl)-vinyl]-phenyl}-ethylsulfanyl)-benzoic acid | ± | 504.31 (M + H) |
| Ia.119 | [2-(2-{3-[(E)-2-(7-Chloro-quinolin-2-yl)-vinyl]-phenyl}-2-ethoxy-ethoxy)-phenyl]-pyrrolidin-1-yl-methanone | ± | 527.42 (M + H) |
| Ia.120 | 2-(2-{3-[(E)-2-(7-Chloro-quinolin-2-yl)-vinyl]-phenyl}-2-propionyloxy-ethylsulfanyl)-benzoic acid | ± | 518.40 (M + H) |
| Ia.121 | [2-(2-{3-[(E)-2-(7-Chloro-quinolin-2-yl)-vinyl]-phenyl}-2-methoxy-ethylsulfanyl)-phenyl]-pyrrolidin-1-yl-methanone | ± | 529.39 (M + H) |
| Ia.122 | [2-(2-{3-[(E)-2-(7-Chloro-quinolin-2-yl)-vinyl]-phenyl}-2-methoxy-ethoxy)-phenyl]-pyrrolidin-1-yl-methanone | ± | 513.42 (M + H) |
| Ia.123 | Cyclopropanecarboxylic acid 1-{3-[(E)-2-(7-chloro-quinolin-2-yl)-vinyl]-phenyl}-2-[2-(pyrrolidine-1-carbonyl)-phenylsulfanyl]-ethyl ester | ± | 583.39 (M + H) |
| Ia.124 | [2-(2-{3-[(E)-2-(7-Chloro-quinolin-2-yl)-vinyl]-phenyl}-2-hydroxy-ethylsulfanyl)-phenyl]-pyrrolidin-1-yl-methanone | ± | 515.34 (M + H) |
| Ia.125 | Acetic acid 1-{3-[(E)-2-(7-chloro-quinolin-2-yl)-vinyl]-phenyl}-2-[2-(pyrrolidine-1-carbonyl)-phenylsulfanyl]-ethyl ester | ± | 557.37 (M + H) |

TABLE 1-continued

Compounds of Formula (Ia)

| S. No. | Name | Sign of rotation | Mass Analysis |
|---|---|---|---|
| Ia.126 | Benzoic acid 1-{3-[(E)-2-(7-chloro-quinolin-2-yl)-vinyl]-phenyl}-2-[2-(pyrrolidine-1-carbonyl)-phenylsulfanyl]-ethyl ester | ± | 619.33 (M + H) |
| Ia.127 | 2-(2-{3-[(E)-2-(7-Chloro-quinolin-2-yl)-vinyl]-phenyl}-2-prop-2-ynyloxy-ethoxy)-benzoic acid | ± | 484.43 (M + H) |
| Ia.128 | 2-[2-{3-[(E)-2-(7-Chloro-quinolin-2-yl)-vinyl]-phenyl}-2-(2-methyl-allyloxy)-ethoxy]-benzoic acid | ± | 500.36 (M + H) |
| Ia.129 | 2-(2-{3-[(E)-2-(7-Chloro-quinolin-2-yl)-vinyl]-phenyl}-2-cyclohexyloxy-ethoxy)-benzoic acid | ± | 528.36 (M + H) |
| Ia.130 | 2-[2-{3-[(E)-2-(7-Chloro-quinolin-2-yl)-vinyl]-phenyl}-2-(3-methyl-but-2-enyloxy)-ethoxy]-benzoic acid | ± | 514.35 (M + H) |
| Ia.131 | 2-[2-{3-[(E)-2-(7-Chloro-quinolin-2-yl) vinyl] phenyl}-2-(indan-2-yloxy)-ethoxy]-benzoic acid | ± | 562.17 (M + H) |
| Ia.132 | 2-[2-{3-[(E)-2-(7-Chloro-quinolin-2-yl)-vinyl]-phenyl}-2-(3-methyl-butoxy)-ethoxy]-benzoic acid | ± | 516.41 (M + H) |
| Ia.133 | 2-(2-But-3-ynyloxy-2-{3-[(E)-2-(7-chloro-quinolin-2-yl)-vinyl]-phenyl}-ethoxy)-benzoic acid | ± | 498.38 (M + H) |
| Ia.134 | 2-[2-{3-[(E)-2-(7-Chloro-quinolin-2-yl)-vinyl]-phenyl}-2-(3-phenyl-allyloxy)-ethoxy]-benzoic acid | ± | 562.38 (M + H) |
| Ia.135 | 2-(2-{3-[(E)-2-(7-Chloro-quinolin-2-yl)-vinyl]-phenyl}-2-pentyloxy-ethoxy)-benzoic acid | ± | 516.40 (M + H) |
| Ia.136 | 2-[2-{3-[(E)-2-(7-Chloro-quinolin-2-yl)-vinyl]-phenyl}-2-(3-phenyl-propoxy)-ethoxy]-benzoic acid | ± | 564.38 (M + H) |
| Ia.137 | 2-(2-{3-[(E)-2-(7-Chloro-quinolin-2-yl)-vinyl]-phenyl}-2-cyclopentyloxy-ethoxy)-benzoic acid | ± | 514.03 (M + H) |
| Ia.138 | 2-[2-{3-[(E)-2-(7-Chloro-quinolin-2-yl)-vinyl]-phenyl}-2-(4-phenyl-butoxy)-ethoxy]-benzoic acid | ± | 578.39 (M + H) |
| Ia.139 | 2-(2-{3-[(E)-2-(7-Chloro-quinolin-2-yl)-vinyl]-phenyl}-2-phenethyloxy-ethoxy)-benzoic acid | ± | 550.38 (M + H) |
| Ia.140 | 2-[2-{3-[(E)-2-(7-Chloro-quinolin-2-yl)-vinyl]-phenyl}-2-(3-phenyl-prop-2-ynyloxy)-ethoxy]-benzoic acid | ± | 560.14 (M + H) |
| Ia.141 | 2-(2-{3-[(E)-2-(7-Chloro-quinolin-2-yl)-vinyl]-phenyl}-2-hex-2-ynyloxy-ethoxy)-benzoic acid | ± | 514.39 (M + H) |
| Ia.142 | 2-(2-{3-[(E)-2-(7-Chloro-quinolin-2-yl)-vinyl]-phenyl}-2-hex-5-ynyloxy-ethoxy)-benzoic acid | ± | 526.38 (M + H) |
| Ia.143 | 2-[2-{3-[(E)-2-(7-Chloro-quinolin-2-yl)-vinyl]-phenyl}-2-(2-thiophen-2-yl-ethoxy)-ethoxy]-benzoic acid | ± | 556.33 (M + H) |
| Ia.144 | 2-(2-{3-[(E)-2-(7-Chloro-quinolin-2-yl)-vinyl]-phenyl}-2-cyclohexylmethoxy-ethoxy)-benzoic acid | ± | 542.17 (M + H) |
| Ia.145 | 2-(2-{3-[(E)-2-(7-Chloro-quinolin-2-yl)-vinyl]-phenyl}-2-cyclobutylmethoxy-ethoxy)-benzoic acid | ± | 514.39 (M + H) |
| Ia.146 | 2-[2-{3-[(E)-2-(7-Chloro-quinolin-2-yl)-vinyl]-phenyl}-2-(thiophen-2-ylmethoxy)-ethoxy]-benzoic acid | ± | 542.29 (M + H) |
| Ia.147 | 2-(2-{3-[(E)-2-(7-Chloro-quinolin-2-yl)-vinyl]-phenyl}-2-prop-2-ynyloxy-ethoxy)-benzoic acid ethyl ester hydrochloride salt | ± | 512.38 (M + H − 36.5) |
| Ia.148 | 2-(2-{3-[(E)-2-(7-Chloro-quinolin-2-yl)-vinyl]-phenyl}-2-pent-4-ynyloxy-ethoxy)-benzoic acid ethyl ester hydrochloride salt | ± | 540.39 (M + H − 36.5) |
| Ia.149 | 2-[2-{3-[(E)-2-(7-Chloro-quinolin-2-yl)-vinyl]-phenyl}-2-(thiophen-2-ylmethoxy)-ethoxy]-benzoic acid ethyl ester hydrochloride salt | ± | 570.13 (M + 1 − 36) |
| Ia.150 | 2-(2-{3-[(E)-2-(7-Chloro-quinolin-2-yl)-vinyl]-phenyl}-2-prop-2-ynyloxy-ethoxy)-5-fluoro-benzoic acid | ± | 501.95 (M + H) |
| Ia.151 | 2-(2-{3-[(E)-2-(7-Chloro-quinolin-2-yl)-vinyl]-phenyl}-2-prop-2-ynyloxy-ethoxy)-4-fluoro-benzoic acid | ± | 502.30 (M + H) |
| Ia.152 | 2-(2-{3-[(E)-2-(7-Chloro-quinolin-2-yl)-vinyl]-phenyl}-2-ethoxy-ethoxy)-5-methoxy-benzoic acid | ± | 504.07 (M + H) |
| Ia.153 | 2-(2-{3-[(E)-2-(7-Chloro-quinolin-2-yl)-vinyl]-phenyl}-2-prop-2-ynyloxy-ethoxy)-5-methoxy-benzoic acid | ± | 514.05 (M + H) |
| Ia.154 | 2-(2-{3-[(E)-2-(7-Chloro-quinolin-2-yl)-vinyl]-phenyl}-2-prop-2-ynyloxy-ethoxy)-5-ethyl-benzoic acid | ± | 512.07 (M + H) |
| Ia.155 | 2-(2-{3-[(E)-2-(7-Chloro-quinolin-2-yl)-vinyl]-phenyl}-2-ethoxy-ethoxy)-5-ethyl-benzoic acid | ± | 502.07 (M + H) |
| Ia.156 | N-[2-(2-{3-[(E)-2-(7-Chloro-quinolin-2-yl)-vinyl]-phenyl}-2-ethoxy-ethoxy)-5-methoxy-benzoyl]-benzenesulfonamide | ± | 643.07 (M + H) |

TABLE 1-continued

Compounds of Formula (Ia)

| S. No. | Name | Sign of rotation | Mass Analysis |
|---|---|---|---|
| Ia.157 | N-[2-(2-{3-[(E)-2-(7-Chloro-quinolin-2-yl)-vinyl]-phenyl}-2-ethoxy-ethoxy)-5-methoxy benzoyl]-methanesulfonamide | ± | 581.01 (M + H) |
| Ia.158 | 2-(3-Acetylamino-3-{3-[(E)-2-(7-chloro-quinolin-2-yl)-vinyl]-phenyl}-propyl)-5-methoxy-benzoic acid | ± | 515.07 (M + H) |
| Ia.159 | 2-(3-{3-[(E)-2-(7-Chloro-quinolin-2-yl)-vinyl]-phenyl}-3-phenylacetylamino-propyl)-5-methoxy-benzoic acid | ± | 591.08 (M + H) |
| Ia.160 | 2-(2-{3-[(E)-2-(7-Chloro-quinolin-2-yl)-vinyl]-phenyl}-2-cyclopentyloxy-ethoxy)-5-methoxy-benzoic acid | ± | 528.09 (M + H) |
| Ia.161 | 2-(2-{3-[(E)-2-(7-Chloro-quinolin-2-yl)-vinyl]-phenyl}-2-cyclopropylmethoxy-ethoxy)-5-methoxy-benzoic acid | ± | 530.12 (M + H) |
| Ia.162 | (S)-2-tert-Butoxycarbonylamino-3-[4-(2-{3-[(E)-2-(7-chloro-quinolin-2-yl)-vinyl]-phenyl}-2-ethoxy-ethoxy)-phenyl]-propionic acid, (RS mixture) | DM | 617.45 (M + H) |
| Ia.163 | [4-(2-{3-[(E)-2-(7-Chloro-quinolin-2-yl)-vinyl]-phenyl}-2-ethoxy-ethoxy)-3-methoxy-phenyl]-acetic acid | ± | 532.16 (M + H) |
| Ia.164 | 2-(2-{3-[(E)-2-(7-Chloro-quinolin-2-yl)-vinyl]-phenyl}-2-ethoxy-ethoxy)-4-methoxy-benzoic acid | ± | 504.12 (M + H) |
| Ia.165 | 2-(2-{3-[(E)-2-(7-Chloro-quinolin-2-yl)-vinyl]-phenyl}-2-imidazol-1-yl-ethoxy)-benzoic acid | ± | 494.07 (M + H) |
| Ia.166 | 2-((S)-2-{3-[(E)-2-(7-Chloro-quinolin-2-yl)-vinyl]-phenyl}-2-ethoxy-ethoxy)-5-methoxy-benzoic acid | + | 503.99 (M + H) |
| Ia.167 | 2-((R)-2-{3-[(E)-2-(7-Chloro-quinolin-2-yl)-vinyl]-phenyl}-2-ethoxy-ethoxy)-5-methoxy-benzoic acid | − | 503.99 (M + H) |
| Ia.168 | 2-(2-{3-[(E)-2-(7-Chloro-quinolin-2-yl)-vinyl]-phenyl}-2-ethoxy-ethoxy)-5-ethoxy-benzoic acid | ± | 518.11 (M + H) |
| Ia.169 | 2-(2-{3-[(E)-2-(7-Chloro-quinolin-2-yl)-vinyl]-phenyl}-2-ethoxy-ethoxy)-5-cyclopropyl-methoxy-benzoic acid | ± | 544.14 (M + H) |
| Ia.170 | 2-(2-{3-[(E)-2-(6,7-Difluoro-quinolin-2-yl)-vinyl]-phenyl}-2-ethoxy-ethoxy)-5-methoxy-benzoic acid | ± | 506.15 (M + H) |
| Ia.171 | 2-(2-{3-[(E)-2-(7-Chloro-quinolin-2-yl)-vinyl]-phenyl}-2-ethoxy-ethoxy)-5-triduetereo methoxy-benzoic acid | ± | 507.09 (M + H) |
| Ia.172 | 2-(2-{3-[(E)-2-(7-Chloro-quinolin-2-yl)-vinyl]-phenyl}-2-cyclopropylmethoxy-ethoxy)-5-triduetereo methoxy-benzoic acid | ± | 533.05 (M + H) |
| Ia.173 | [2-(2-{3-[(E)-2-(7-Chloro-quinolin-2-yl)-vinyl]-phenyl}-2-ethoxy-ethoxy)-5-methoxy-phenyl]-pyrrolidin-1-yl-methanone | ± | 557.08 (M + H) |
| Ia.174 | 2-(2-{3-[(E)-2-(7-Chloro-quinolin-2-yl)-vinyl]-phenyl}-2-triduetereo methoxy-ethoxy)-5-methoxy-benzoic acid | ± | 493.03 (M + H) |
| Ia.175 | [2-(2-{3-[(E)-2-(7-Chloro-quinolin-2-yl)-vinyl]-phenyl}-2-cyclopropylmethoxy-ethoxy)-5-methoxy-phenyl]-pyrrolidin-1-yl-methanone | ± | 583.12 (M + H) |
| Ia.176 | 2-(2-Cyclopropylmethoxy-2-{3-[(E)-2-(7-methoxy-Ia.uinolin-2-yl)-vinyl]-phenyl}-ethoxy)-5-methoxy-benzoic aclid | ± | 526.10 (M + H) |
| Ia.177 | 2-(2-{3-[(E)-2-(7-Chloro-quinolin-2-yl)-vinyl]-phenyl}-2-ethylsulfanyl-ethoxy)-5-methoxy-benzoic acid | ± | 520.02 (M + H) |
| Ia.178 | 2-(2-Ethoxy-2-{3-[(E)-2-(7-methoxy-quinolin-2-yl)-vinyl]-phenyl}-ethoxy)-5-methoxy-benzoic acid | ± | 500.07 (M + H) |
| Ia.179 | 2-(2-{3-[(E)-2-(7-Chloro-quinolin-2-yl)-vinyl]-phenyl}-2-ethoxy-ethoxy)-5-methoxy-N-methyl-benzamide | ± | 517.07 (M + H) |
| Ia.180 | 2-(2-{3-Bromo-5-[(E)-2-(7-chloro-quinolin-2-yl)-vinyl]-phenyl}-2-ethoxy-ethoxy)-5-methoxy-benzoic acid | ± | 583.96 (M + H) |
| Ia.181 | 2-{2-Ethoxy-2-[3-((E)-2-quinolin-2-yl-vinyl)-phenyl]-ethoxy}-5-methoxy-benzoic acid | ± | — |
| Ia.182 | 2-{2-Cyclopropylmethoxy-2-[3-((E)-2-quinolin-2-yl-vinyl)-phenyl]-ethoxy}-5-methoxy-benzoic acid | ± | 496.16 (M + H) |
| Ia.183 | 2-((S)-2-{3-[(E)-2-(7-Chloro-quinolin-2-yl)-vinyl]-phenyl}-2-cyclopropylmethoxy-ethoxy)-5-methoxy-benzoic acid | + | 530.08 (M + H) |
| Ia.184 | 2-((R)-2-{3-[(E)-2-(7-Chloro-quinolin-2-yl)-vinyl]-phenyl}-2-cyclopropylmethoxy-ethoxy)-5-methoxy-benzoic acid | − | 530.08 (M + H) |

TABLE 1-continued

Compounds of Formula (Ia)

| S. No. | Name | Sign of rotation | Mass Analysis |
|---|---|---|---|
| Ia.185 | 2-((S)-2-{3-[(E)-2-(7-Chloro-quinolin-2-yl)-vinyl]-phenyl}-2-prop-2-ynyloxy-ethoxy)-5-methoxy-benzoic acid | + | 514.04 (M + H) |
| Ia.186 | 2-((R)-2-{3-[(E)-2-(7-Chloro-quinolin-2-yl)-vinyl]-phenyl}-2-prop-2-ynyloxy-ethoxy)-5-methoxy-benzoic acid | − | 514.04 (M + H) |
| Ia.187 | 2-((S)-2-{3-[(E)-2-(6,7-Difluoro-quinolin-2-yl)-vinyl]-phenyl}-2-ethoxy-ethoxy)-5-methoxybenzoic acid | + | 506.08 (M + H) |
| Ia.188 | 2-((R)-2-{3-[(E)-2-(6,7-Difluoro-quinolin-2-yl)-vinyl]-phenyl}-2-ethoxy-ethoxy)-5-methoxy-benzoic acid | − | 506.08 (M + H) |
| Ia.189 | 2-{(S)-2-Ethoxy-2-[3-((E)-2-quinolin-2-yl-vinyl)-phenyl]-ethoxy}-5-methoxy-benzoic acid | + | 470.16 (M + H) |
| Ia.190 | 2-{(R)-2-Ethoxy-2-[3-((E)-2-quinolin-2-yl-vinyl)-phenyl]-ethoxy}-5-methoxy-benoic acid | − | 470.17 (M + H) |
| Ia.191 | 2-(2-{3-[(E)-2-(7-Chloro-quinolin-2-yl)-vinyl]-phenyl}-2-isobutoxy-ethoxy)-5-methoxy-benzoic acid | ± | 532.10 (M + H) |
| Ia.192 | 2-{2-[3-((E)-2-Benzothiazol-2-yl-vinyl)-phenyl]-2-ethoxy-ethoxy}-5-methoxy-benzoic acid | ± | 476.08 (M + H) |
| Ia.193 | 2-{2-[3-((E)-2-Benzothiazol-2-yl-vinyl)-phenyl]-2-cyclopropylmethoxy-ethoxy}-5-methoxy-benzoic acid | ± | 502.09 (M + H) |
| Ia.194 | 2-((R)--{3-[(E)-2-(7-Chloro-quinolin-2-yl)-vinyl]-phenyl}-2-ethoxy-ethylamino)-5-methoxy-benzoic acid | | 503.11 (M + H) |
| Ia.195 | 2-((R)-2-{3-[(E)-2-(7-Chloro-quinolin-2-yl)-vinyl]-phenyl}-2-ethoxy-ethoxy)-5-hydroxymethyl-benzoic acid | | 504.10 (M + H) |
| Ia.196 | 2-((R)-2-{3-[(E)-2-(7-Chloro-quinolin-2-yl)-vinyl]-phenyl}-2-isobutoxy-ethoxy)-5-methoxy-benzoic acid | − | 532.13 (M + H) |
| Ia.197 | 2-((R)-2-{3-[(E)-2-(7-Chloro-quinolin-2-yl)-vinyl]-phenyl}-2-ethoxy-ethoxy)-5-formyl-benzoic acid | − | 502.09 (M + H) |
| Ia.198 | 2-((R)-2-{3-[(E)-2-(7-Chloro-quinolin-2-yl)-vinyl]-phenyl}-2-methoxy-ethoxy)-5-methoxy-benzoic acid | − | 490.11 (M + H) |
| Ia.199 | 2-{2-[3-(7-Chloro-quinolin-2-ylethynyl)-phenyl]-2-ethoxy-ethoxy}-5-methoxy-benzoic acid | ± | 502.07 (M + H) |
| Ia.200 | 2-[(R)-2-{3-[(E)-2-(7-Chloro-quinolin-2-yl)-vinyl]-phenyl}-2-(2,2,2-trifluoro-ethoxy)-ethoxy]-5-methoxy-benzoic acid | − | 558.13 (M + H) |
| Ia.201 | 2-[(S)-2-{3-[(E)-2-(7-Chloro-quinolin-2-yl)-vinyl]-phenyl}-2-(2-fluoro-ethoxy)-ethoxy]-5-methoxy-benzoic acid | + | 522.11 (M + H) |
| Ia.202 | 2-[(R)-2-{3-[(E)-2-(7-Chloro-quinolin-2-yl)-vinyl]-phenyl}-2-(2-fluoro-ethoxy)-ethoxy]-5-methoxy-benzoic acid | − | 522.11 (M + H) |
| Ia.203 | 2-(2-(2-Chloro-ethoxy)-2-{3-[(E)-2-(7-chloro-quinolin-2-yl)-vinyl]-phenyl}-ethoxy)-5-methoxy-benzoic acid | ± | 538.05 (M + H) |
| Ia.204 | 2-(2-{3-[(E)-2-(7-Chloro-quinolin-2-yl)-vinyl]-phenyl}-2-ethoxy-ethoxy)-nicotinic acid | ± | 475.07 (M + H) |
| Ia.205 | 2-(2-{3-[(E)-2-(7-Chloro-quinolin-2-yl)-vinyl]-phenyl}-2-ethoxy-ethylsulfanyl)-nicotinic acid | ± | 491.03 (M + H) |
| Ia.206 | 2-((R)-2-{3-[(E)-2-(7-Chloro-quinolin-2-yl)-vinyl]-phenyl}-2-ethoxy-ethoxy)-5-fluoromethoxy-benzoic acid | − | 522.13 (M + H) |
| Ia.207 | 2-((R)-2-{3-[(E)-2-(7-Chloro-quinolin-2-yl)-vinyl]-phenyl}-2-prop-2-ynyloxy-ethoxy)-5-fluoro-methoxy-benzoic acid | − | 532.13 (M + H) |
| Ia.208 | 2-(2-{3-[(E)-2-(7-Chloro-quinolin-2-yl)-vinyl]-phenyl}-2-methoxy-ethoxy)-5-fluoromethoxy-benzoic acid | ± | 508.07 (M + H) |
| Ia.209 | 2-(2-{6-[(E)-2-(7-Chloro-quinolin-2-yl)-vinyl]-pyridin-2-yl}-2-ethoxy-ethoxy)-5-methoxy-benzoic acid | ± | 505.07 (M + H) |
| Ia.210 | 2-(2-{6-[(E)-2-(7-Chloro-quinolin-2-yl)-vinyl]-pyridin-2-yl}-2-cyclopropylmethoxy-ethoxy)-5-methoxy-benzoic acid | ± | 530.11 (M + H) |
| Ia.211 | 2-(2-{3-[(E)-2-(6,7-Difluoro-quinolin-2-yl)-vinyl]-phenyl}-2-ethoxy-ethoxy)-5-fluoromethoxy-benzoic acid | ± | 524.13 (M + H) |
| Ia.212 | 2-(2-{6-[(E)-2-(7-Chloro-quinolin-2-yl)-vinyl]-pyridin-2-yl}-2-methoxy-ethoxy)-5-methoxy-benzoic acid | ± | 491.06 (M + H) |
| Ia.213 | 2-(2-{3-[(E)-2-(7-Chloro-quinolin-2-yl)-vinyl]-phenyl}-2-prop-2-ynyloxy-ethoxy)-5-prop-2-ynyloxy-benzoic Acid | ± | 538.19 (M + H) |
| Ia.214 | 2-((R)-2-{3-[(E)-2-(7-Chloro-quinolin-2-yl)-vinyl]-phenyl}-2-ethoxy-ethoxy)-5-triduetereo-methoxy-benzoic acid | − | 507.21 (M + H) |

TABLE 1-continued

Compounds of Formula (Ia)

| S. No. | Name | Sign of rotation | Mass Analysis |
|---|---|---|---|
| Ia.215 | 5-[1-[2-(2-{3-[(E)-2-(7-Chloro-quinolin-2-yl)-vinyl]-phenyl}-2-ethoxy-ethoxy)-5-methoxy-phenyl]-meth-(Z)-ylidene]-thiazolidine-2,4-dione | ± | 587.01 (M + H) |
| Ia.216 | 2-((R)-2-{3-[(E)-2-(7-Chloro-quinolin-2-yl)-vinyl]-phenyl}-2-prop-2-ynyloxy-ethoxy)-5-triduetereo methoxy-benzoic acid | − | 517.21 (M + H) |
| Ia.217 | 2-((R)-2-{3-[(E)-2-(7-Chloro-quinolin-2-yl)-vinyl]-phenyl}-2-cyclopropylmethoxy-ethoxy)-5-triduetereomethoxy-benzoic Acid | − | 533.25 (M + H) |
| Ia.218 | 2-((S)-2-{3-[(E)-2-(7-Chloro-quinolin-2-yl)-vinyl]-phenyl}-2-cyclopropylmethoxy-ethoxy)-5-triduetereomethoxy-benzoic acid | + | 533.22 (M + H) |
| Ia.219 | 2-((S)-2-{3-[(E)-2-(6,7-Difluoro-quinolin-2-yl)-vinyl]-phenyl}-2-ethoxy-ethoxy)-5-triduetereo-methoxy-benzoic acid | + | 509.1 (M + H) |
| Ia.220 | 2-((R)-2-{3-[(E)-2-(6,7-Difluoro-quinolin-2-yl)-vinyl]-phenyl}-2-ethoxy-ethoxy)-5-triduetereo-methoxy-benzoic acid | − | 509.12 (M + H) |
| Ia.221 | 2-((S)-2-{3-[(E)-2-(7-Chloro-quinolin-2-yl)-vinyl]-phenyl}-2-methoxy-ethoxy)-5-Triduetereo methoxy-benzoic acid | + | 493.16 (M + H) |
| Ia.222 | 2-((R)-2-{3-[(E)-2-(7-Chloro-quinolin-2-yl)-vinyl]-phenyl}-2-methoxy-ethoxy)-5-Triduetereo methoxy-benzoic acid | − | 493.18 (M + H) |
| Ia.223 | 2-((S)-2-{3-[(E)-2-(7-Chloro-quinolin-2-yl)-vinyl]-phenyl}-2-cyclopropylmethoxy-ethoxy)-5-fluoromethoxy-benzoic acid | + | 548.09 (M + H) |
| Ia.224 | 2-((R)-2-{3-[(E)-2-(7-Chloro-quinolin-2-yl)-vinyl]-phenyl}-2-cyclopropylmethoxyethoxy)-5-fluoro-methoxy-benzoic acid | − | 548.07 (M + H) |
| Ia.225 | 2-((S)-2-{3-[(E)-2-(6,7-Difluoro-quinolin-2-yl)-vinyl]-phenyl}-2-prop-2-ynyloxy-ethoxy)-5-methoxy-benzoic acid | + | 516.12 (M + H) |
| Ia.226 | 2-((R)-2-{3-[(E)-2-(6,7-Difluoro-quinolin-2-yl)-vinyl]-phenyl}-2-prop-2-ynyloxy-ethoxy)-5-methoxy-benzoic acid | − | 516.13 (M + H) |
| Ia.227 | 2-((S)-2-{3-[(E)-2-(6,7-Difluoro-quinolin-2-yl)-vinyl]-phenyl}-2-ethoxy-ethoxy)-5-fluoromethoxy-benzoic acid | + | 524.13 (M + H) |
| Ia.228 | 2-((R)-2-{3-[(E)-2-(6,7-Difluoro-quinolin-2-yl)-vinyl]-phenyl}-2-ethoxy-ethoxy)-5-fluoromethoxy-benzoic acid | − | 524.12 (M + H) |
| Ia.229 | 2-((S)-2-{3-[(E)-2-(7-Chloro-quinolin-2-yl)-vinyl]-phenyl}-2-isobutoxy-ethoxy)-5-Triduetereo methoxy-benzoic acid | + | 535.12 (M + H) |
| Ia.230 | 2-((R)-2-{3-[(E)-2-(7-Chloro-quinolin-2-yl)-vinyl]-phenyl}-2-isobutoxy-ethoxy)-5-Triduetereo methoxy-benzoic acid | − | 535.12 (M + H) |
| Ia.231 | (1-{(S)-1-{3-[(E)-2-(7-Chloro-quinolin-2-yl)vinyl]-phenyl}-2-[2-(1-hydroxy-1-methyl-ethyl)-4-methoxy-phenoxy]-ethylsulfanylmethyl}-cyclopropyl)-acetic acid | + | 618.11 (M + H) |
| Ia.232 | 2-((S)-2-Cyclopropylmethoxy-2-{3-[(E)-2-(6,7-difluoro-quinolin-2-yl)-vinyl]-phenyl}-ethoxy)-5-methoxy-benzoic acid | + | 532.13 (M + H) |
| Ia.233 | 2-((R)-2-Cyclopropylmethoxy-2-{3-[(E)-2-(6,7-difluoro-quinolin-2-yl)-vinyl]-phenyl}-ethoxy)-5-methoxy-benzoic acid | − | 532.13 (M + H) |
| Ia.234 | 2-(2-{3-[(E)-2-(7-Chloro-quinolin-2-yl)-vinyl]-phenyl}-2-ethoxy-ethoxy)-naphthalene-1-carboxylic acid | ± | 524.1 (M + H) |
| Ia.235 | 2-((R)-2-{3-[(E)-2-(7-Chloro-quinolin-2-yl)-vinyl]-phenyl}-2-ethoxy-ethoxy)-5-triduetromethoxy-benzoic acid ethyl ester hydrochloride | − | 535.18 (M + H) |
| Ia.236 | 2-((R)-2-{3-[(E)-2-(7-Chloro-quinolin-2-yl)-vinyl]-phenyl}-2-ethoxy-ethoxy)-5-methoxy-benzoic acid ethyl ester hydrochloride | − | 532.13 (M + H) |
| Ia.237 | 3,5-Dichloro-2-(2-{3-[(E)-2-(7-chloro-quinolin-2-yl)-vinyl]-phenyl}-2-ethoxy-ethoxy)-benzoic acid | ± | 543.98 (M + H) |
| Ia.238 | 2-((R)-2-Cyclopropylmethoxy-2-{3-[(E)-2-(7-fluoro-quinolin-2-yl)-vinyl]-phenyl}-ethoxy)-5-methoxy-benzoic acid | − | 514.16 (M + H) |
| Ia.239 | 2-((S)-2-Cyclopropylmethoxy-2-{3-[(E)-2-(7-fluoro-quinolin-2-yl)-vinyl]-phenyl}-ethoxy)-5-methoxy-benzoic acid | + | 514.16 (M + H) |

TABLE 1-continued

Compounds of Formula (Ia)

| S. No. | Name | Sign of rotation | Mass Analysis |
|---|---|---|---|
| Ia.240 | 2-((S)-2-{3-[(E)-2-(7-Chloro-6-fluoro-quinolin-2-yl)-vinyl]-phenyl}-2-cyclopropyl methoxy-ethoxy)-5-methoxy-benzoic acid | + | 548.12 (M + H) |
| Ia.241 | 2-((R)-2-{3-[(E)-2-(7-Chloro-6-fluoro-quinolin-2-yl)-vinyl]-phenyl}-2-cyclopropyl methoxy-ethoxy)-5-methoxy-benzoic acid | − | 548.12 (M + H) |
| Ia.242 | 2-((S)-2-Cyclopropylmethoxy-2-{3-[(E)-2-(6,7-difluoro-quinolin-2-yl)-vinyl]-phenyl}-ethoxy)-5-fluoromethoxy-benzoic acid | + | 550.16 (M + H) |
| Ia.243 | 2-((R)-2-Cyclopropylmethoxy-2-{3-[(E)-2-(6,7-difluoro-quinolin-2-yl)-vinyl]-phenyl}-ethoxy)-5-fluoromethoxy-benzoic acid | − | 550.16 (M + H) |
| Ia.244 | 2-((S)-2-{3-[(E)-2-(7-Chloro-6-fluoro-quinolin-2-yl)-vinyl]-phenyl}-2-prop-2-ynyloxy-ethoxy)-5-methoxy-benzoic acid | + | 532.1 (M + H) |
| Ia.245 | 2-((R)-2-{3-[(E)-2-(7-Chloro-6-fluoro-quinolin-2-yl)-vinyl]-phenyl}-2-prop-2-ynyloxy-ethoxy)-5-methoxy-benzoic acid | − | 532.08 (M + H) |
| Ia.246 | 2-((E)-(S)-4-{3-[(E)-2-(7-Chloro-quinolin-2-yl)-vinyl]-phenyl}-2-cyclopropyl methoxy-but-3-enyloxy)-5-methoxy-benzoic acid | + | 556.14 (M + H)* |
| Ia.247 | 2-((E)-(R)-4-{3-[(E)-2-(7-Chloro-quinolin-2-yl)-vinyl]-phenyl}-2-cyclopropyl methoxy-but-3-enyloxy)-5-methoxy-benzoic acid | − | 556.14 (M + H)* |
| Ia.248 | 2-((S)-2-Cyclopropylmethoxy-2-{3-[(E)-2-(7-fluoro-quinolin-2-yl)-vinyl]-phenyl}-ethoxy)-5-fluoro-methoxy-benzoic acid | + | 532.1 (M + H) |
| Ia.249 | 2-((R)-2-Cyclopropylmethoxy-2-{3-[(E)-2-(7-fluoro-quinolin-2-yl)-vinyl]-phenyl}-ethoxy)-5-fluoro-methoxy-benzoic acid | − | 532.15 (M + H) |
| Ia.250 | 2-((S)-2-{3-[(E)-2-(7-Fluoro-quinolin-2-yl)-vinyl]-phenyl}-2-prop-2-ynyloxy-ethoxy)-5-methoxy-benzoic acid | + | 498.16 (M + H) |
| Ia.251 | 2-((R)-2-{3-[(E)-2-(7-Fluoro-quinolin-2-yl)-vinyl]-phenyl}-2-prop-2-ynyloxy-ethoxy)-5-methoxy-benzoic acid | − | 498.14 (M + H) |
| Ia.252 | 2-((S)-2-Cyclopropylmethoxy-2-{3-[(E)-2-(6-fluoro-quinolin-2-yl)-vinyl]-phenyl}-ethoxy)-5-methoxy-benzoic acid | + | 514.22 (M + H) |
| Ia.253 | 2-((R)-2-Cyclopropylmethoxy-2-{3-[(E)-2-(6-fluoro-quinolin-2-yl)-vinyl]-phenyl}-ethoxy)-5-methoxy-benzoic acid | − | 514.2 (M + H) |
| Ia.254 | 2-((R)-2-Cyclopropylmethoxy-2-{3-[(E)-2-(6,7-dichloro-quinolin-2-yl)-vinyl]-phenyl}-ethoxy)-5-methoxy-benzoic acid | − | 564.06 (M + H) |
| Ia.255 | 2-((S)-2-Cyclopropylmethoxy-2-{3-[(E)-2-(6,7-dichloro-quinolin-2-yl)-vinyl]-phenyl}-ethoxy)-5-methoxy-benzoic acid | + | 564.12 (M + H) |
| Ia.256 | 2-((S)-3-{3-[(E)-2-(7-Chloro-quinolin-2-yl)-vinyl]-phenoxy}-2-cyclo propylmethoxy-propoxy)-5-methoxy-benzoic acid | + | 560.16 (M + H)* |
| Ia.257 | 2-((R)-3-{3-[(E)-2-(7-Chloro-quinolin-2-yl)-vinyl]-phenoxy}-2-cyclopropylmethoxy-propoxy)-5-methoxy-benzoic acid | − | 560.16 (M + H)* |
| Ia.258 | 2-((R)-2-{3-[(E)-2-(6-Fluoro-quinolin-2-yl)-vinyl]-phenyl}-2-prop-2-ynyloxy-ethoxy)-5-methoxy-benzoic acid | − | 498.16 (M + H) |
| Ia.259 | 2-((S)-2-{3-[(E)-2-(6-Fluoro-quinolin-2-yl)-vinyl]-phenyl}-2-prop-2-ynyloxy-ethoxy)-5-methoxy-benzoic acid | + | 498.15 (M + H) |
| Ia.260 | 2-((S)-2-{3-[(E)-2-(6,7-Dichloro-quinolin-2-yl)-vinyl]-phenyl}-2-prop-2-ynyloxy-ethoxy)-5-methoxy-benzoic acid | + | 548.1 (M + H) |
| Ia.261 | 2-((R)-2-{3-[(E)-2-(6,7-Dichloro-quinolin-2-yl)-vinyl]-phenyl}-2-prop-2-ynyloxy-ethoxy)-5-methoxy-benzoic acid | − | 548.07 (M + H) |
| Ia.262 | 2-[(S)-2-{3-[(E)-2-(6,7-Dichloro-quinolin-2-yl)-vinyl]-phenyl}-2-(2-methyl-allyloxy)-ethoxy]-5-methoxy-benzoic acid | + | 564.18 (M + H) |
| Ia.263 | 2-[(R)-2-{3-[(E)-2-(6,7-Dichloro-quinoline-2-yl)-vinyl]-phenyl}-2-(2-methyl-allyloxy)-ethoxy]-5-methoxy-benzoic acid | − | 564.07 (M + H) |
| Ia.264 | 2-[(S)-2-{3-[(E)-2-(6,7-Dichloro-quinolin-2-yl)-vinyl]-phenyl}-2-(2-fluoro-ethoxy)-ethoxy]-5-methoxy-benzoic acid | + | 556.06 (M + H) |

TABLE 1-continued

Compounds of Formula (Ia)

| S. No. | Name | Sign of rotation | Mass Analysis |
|---|---|---|---|
| Ia.265 | 2-[(R)-2-{3-[(E)-2-(6,7-Dichloro-quinolin-2-yl)-vinyl]-phenyl}-2-(2-fluoro-ethoxy)-ethoxy]-5-methoxy-benzoic acid | − | 556.08 (M + H) |
| Ia.266 | 2-[(S)-2-{3-[(E)-2-(6,7-Dichloro-quinolin-2-yl)-vinyl]-phenyl}-2-(2,2,2-trifluroethoxy)-ethoxy]-5-methoxy-benzoic acid | + | 592.03 (M + H) |
| Ia.267 | 2-[(R)-2-{3-[(E)-2-(6,7-Dichloro-quinolin-2-yl)-vinyl]-phenyl}-2-(2,2,2-trifluoroethoxy)-ethoxy]-5-methoxy-benzoic acid | − | 592.04 (M + H) |
| Ia.268 | 2-((S)-2-Cyclopropylmethoxy-2-{3-[(E)-2-(7,8-dichloro-quinolin-2-yl)-vinyl]-phenyl}-ethoxy)-5-methoxy-benzoic acid | + | 564.05 (M + H) |
| Ia.269 | 2-((R)-2-Cyclopropylmethoxy-2-{3-[(E)-2-(7,8-dichloro-quinolin-2-yl)-vinyl]-phenyl}-ethoxy)-5-methoxy-benzoic | − | 564.05 (M + H) |
| Ia.270 | 2-[(S)-2-{3-[(E)-2-(7-Chloro-6-fluoro-quinolin-2-yl)-vinyl]-phenyl}-2-(2-fluoro-ethoxy)-ethoxy]-5-methoxy-benzoic acid | + | 540.04 (M + H) |
| Ia.271 | 2-[(R)-2-{3-[(E)-2-(7-Chloro-6-fluoro-quinolin-2-yl)-vinyl]-phenyl}-2-(2-fluoro-ethoxy)-ethoxy]-5-methoxy-benzoic acid | − | 540.06 (M + H) |
| Ia.272 | 2-[(S)-2-{3-[(E)-2-(7-Chloro-6-fluoro-quinolin-2-yl)-vinyl]-phenyl}-2-(2-methyl-allyloxy)-ethoxy]-5-methoxy-benzoic acid | + | 548.16 (M + H) |
| Ia.273 | 2-[(R)-2-{3-[(E)-2-(7-Chloro-6-fluoro-quinolin-2-yl)-vinyl]-phenyl}-2-(2-methyl-allyloxy)-ethoxy]-5-methoxy-benzoic acid | − | 548.16 (M + H) |
| Ia.274 | 2-[(S)-2-{3-[(E)-2-(7-Chloro-6-fluoro-quinolin-2-yl)-vinyl]-phenyl}-2-(2,2,2-trifluoro-ethoxy)-ethoxy]-5-methoxy-benzoic acid | + | 576.27 (M + H) |
| Ia.275 | 2-[(R)-2-{3-[(E)-2-(7-Chloro-6-fluoro-quinolin-2-yl)-vinyl]-phenyl}-2-(2,2,2-trifluoro-ethoxy)-ethoxy]-5-methoxy-benzoic acid | − | 576.27 (M + H) |
| Ia.276 | 2-[(S)-2-{3-[(E)-2-(7-Chloro-quinolin-2-yl)-vinyl]-phenyl}-2-(2-methyl-allyloxy)-ethoxy]-5-methoxy-benzoic acid | + | 530.09 (M + H) |
| Ia.277 | 2-[(R)-2-{3-[(E)-2-(7-Chloro-quinolin-2-yl)-vinyl]-phenyl}-2-(2-methyl-allyloxy)-ethoxy]-5-methoxy-benzoic acid | − | 530.09 (M + H) |
| Ia.278 | 2-{2-(2-Fluoro-ethoxy)-2-[3-((E)-2-quinoxalin-2-yl-vinyl)-phenyl]-ethoxy}-5-methoxy-benzoic acid | ± | 489.12 (M + H) |
| Ia.279 | 2-{(S)-2-Cyclopropylmethoxy-2-[3-((E)-2-quinoxalin-2-yl-vinyl)-phenyl]-ethoxy}-5-methoxy-benzoic acid | + | 497.2 (M + H) |
| Ia.280 | 2-{(R)-2-Cyclopropylmethoxy-2-[3-((E)-2-quinoxalin-2-yl-vinyl)-phenyl]-ethoxy}-5-methoxy-benzoic acid | − | 497.2 (M + H) |
| Ia-281 | 2-((R)-2-{3-[(Z)-2-(7-Chloro-6-fluoro-quinolin-2-yl)-vinyl]-phenyl}-2-cyclopropyl methoxy-ethoxy)-5-methoxy-benzoic acid | − | 548.35 (M + H) |
| Ia-282 | 2-((R)-2-{3-[(Z)-2-(7-Chloro-quinolin-2-yl)-vinyl]-phenyl}-2-prop-2-ynyloxy-ethoxy)-5-methoxy-benzoic acid | − | 514.33 (M + H) | l#Mass was determined in CI mode. Configurations assigned are relative.

TABLE 2

Compounds of Formula (Ib) and (Ic)

| S. No. | Name | Sign of Rotation | Mass (+) |
|---|---|---|---|
| Ib.01 | 2-[2-(2-{3-[(E)-2-(7-Chloro-quinolin-2-yl)-vinyl]-phenyl}-[1,3]dithian-2-yl)-ethyl]-benzoic acid | | 532.34 (M + H) |
| Ib.02 | 2-[2-(2-{3-[(E)-2-(7-Chloro-quinolin-2-yl)-vinyl]-phenyl}-[1,3]dithiolan-2-yl)-ethyl]-benzoic acid | | 518.08 (M + H) |
| Ib.03 | 2-[2-(2-{3-[(E)-2-(7-Chloro-quinolin-2-yl)-vinyl]-phenyl}-[1,3]dioxan-2-yl)-ethyl]-benzoic acid | | 500.37 (M + H) |
| Ib.04 | 2-[2-(2-{3-[(E)-2-(7-Chloro-quinolin-2-yl)-vinyl]-phenyl}-[1,3]dioxolan-2-yl)-ethyl]-benzoic acid | | 486.31 (M + H) |
| Ib.05 | 2-[2-(2-{3-[(E)-2-(7-Chloro-quinolin-2-yl)-vinyl]-phenyl}-[1,3]dioxolan-2-yl)-ethyl]-benzoic acid ethyl ester | | 514.39 (M + H) |

TABLE 2-continued

Compounds of Formula (Ib) and (Ic)

| S. No. | Name | Sign of Rotation | Mass (+) |
|---|---|---|---|
| Ib.06 | 2-[2-(2-{3-[(E)-2-(7-Chloro-quinolin-2-yl)-vinyl]-phenyl}-[1,3]dioxolan-2-yl)-ethyl]-benzoic acid 4-hydroxy-but-2-ynyl ester | | 554.15 (M + H) |
| Ib.07 | 2-[2-(2-{3-[(E)-2-(7-Chloro-quinolin-2-yl)-vinyl]-phenyl}-[1,3]dioxolan-2-yl)-ethyl]-benzoic acid 1-acetoxy-ethyl ester | ± | 526.16 (M + H) |
| Ib.08 | 2-[2-(2-{3-[(E)-2-(7-Chloro-quinolin-2-yl)-vinyl]-phenyl}-[1,3]dioxolan-2-yl)-ethyl]-benzoic acid isopropoxycarbonyloxymethyl ester | | 602.36 (M + H) |
| Ib.09 | 2-[2-(2-{3-[(E)-2-(7-Chloro-quinolin-2-yl)-vinyl]-phenyl}-[1,3]dioxolan-2-yl)-ethyl]-benzoic acid 2,2-dimethyl-propionyloxymethyl ester | | 600.40 (M + H) |
| Ib.10 | 2-[2-(2-{3-[(E)-2-(7-Chloro-quinolin-2-yl)-vinyl]-phenyl}-[1,3]dioxolan-2-yl)-ethyl]-benzoic acid isopropyl ester | | 528.41 (M + H) |
| Ib.11 | 2-[2-(2-{3-[(E)-2-(7-Chloro-quinolin-2-yl)-vinyl]-phenyl}-[1,3]dioxolan-2-yl)-ethyl]-benzoic acid 5-methyl-2-oxo-[1,3]dioxol-4-ylmethyl ester | | 598.34 (M + H) |
| Ib.12 | 2-[2-(2-{3-[(E)-2-(7-Chloro-quinolin-2-yl)-vinyl]-phenyl}-[1,3]dioxolan-2-yl)-ethyl]-benzoic acid 2-morpholin-4-yl-ethyl ester | | — |
| Ib.13 | 2-[2-(2-{3-[(E)-2-(7-Chloro-quinolin-2-yl)-vinyl]-phenyl}-[1,3]dioxolan-2-yl)-ethyl]-benzoic acid methyl ester | | 500.38 (M + H) |
| Ib.14 | 2-[2-(2-{3-[(E)-2-(7-Chloro-quinolin-2-yl)-vinyl]-phenyl}-[1,3]dioxolan-2-yl)-ethyl]-benzoic acid cyclopropylmethyl ester | | 540.42 (M + H) |
| Ib.15 | 2-[2-(2-{3-[(E)-2-(7-Chloro-quinolin-2-yl)-vinyl]-phenyl}-[1,3]dioxolan-2-yl)-ethyl]-benzoic acid isobutyl ester | | 542.42 (M + H) |
| Ib.16 | 2-[2-(2-{3-[(E)-2-(7-Chloro-quinolin-2-yl)-vinyl]-phenyl}-[1,3]dioxolan-2-yl)-ethyl]-benzoic acid cyclohexyl ester | | 568.12 (M + H) |
| Ib.17 | 2-[2-(2-{3-[(E)-2-(7-Chloro-quinolin-2-yl)-vinyl]-phenyl}-[1,3]dioxolan-2-yl)-ethyl]-benzoic acid cyclobutylmethyl ester | | 554.11 (M + H) |
| Ib.18 | 2-[2-(2-{3-[(E)-2-(7-Chloro-quinolin-2-yl)-vinyl]-phenyl}-[1,3]dioxolan-2-yl)-ethyl]-benzoic acid cyclopentyl ester | | 554.07 (M + H) |
| Ib.19 | 2-[2-(2-{3-[(E)-2-(7-Chloro-quinolin-2-yl)-vinyl]-phenyl}-[1,3]dioxolan-2-yl)-ethyl]-benzoic acid allyl ester | | 526.07 (M + H) |
| Ib.20 | 2-[2-(2-{3-[(E)-2-(7-Chloro-quinolin-2-yl)-vinyl]-phenyl}-[1,3]dioxolan-2-yl)-ethyl]-benzoic acid prop-2-ynyl ester | | 524.04 (M + H) |
| Ib.21 | 2-[2-(2-{3-[(E)-2-(7-Chloro-quinolin-2-yl)-vinyl]-phenyl}-[1,3]dioxolan-2-yl)-ethyl]benzoic acid 3-methyl-oxetan-3-ylmethyl ester | | 570.04 (M + H) |
| Ib.22 | 2-[2-(2-{3-[(E)-2-(7-Chloro-quinolin-2-yl)-vinyl]-phenyl}-[1,3]dioxolan-2-yl)-ethyl]-benzoic acid 2,2,2-trifluoro-ethyl ester | | 567.97 (M + H) |
| Ib.23 | 2-[2-(2-{3-[(E)-2-(7-Chloro-quinolin-2-yl)-vinyl]-phenyl}-[1,3]dioxolan-2-yl)-ethyl]-benzoic acid 2-fluoro-1-fluoromethyl-ethyl ester | | 564.16 (M + H) |
| Ib.24 | 2-[2-(2-{3-[(E)-2-(7-Chloro-quinolin-2-yl)-vinyl]-phenyl}-[1,3]dioxolan-2-yl)-ethyl]-benzoic acid benzyl ester | | 576.20 (M + H) |
| Ib.25 | 2-[2-(2-{3-[(E)-2-(7-Chloro-quinolin-2-yl)-vinyl]-phenyl}-5,5-dimethyl-[1,3]dioxan-2-yl)-ethyl]-benzoic acid methyl ester | | 542.43 (M + H) |
| Ib.26 | 2-[2-(2-{3-[(E)-2-(7-Chloro-quinolin-2-yl)-vinyl]-phenyl}-5,5-dimethyl-[1,3]dioxan-2-yl)-ethyl]-benzoic acid | | 528.41 (M + H) |
| Ib.27 | 2-[2-(2-{3-[(E)-2-(7-Chloro-quinolin-2-yl)-vinyl]-phenyl}-5,5-dimethyl-[1,3]dioxan-2-yl)-ethyl]-benzoic acid ethyl ester | | 556.45 (M + H) |
| Ib.28 | 2-[2-(2-{3-[(E)-2-(7-Chloro-quinolin-2-yl)-vinyl]-phenyl}-5,5-dimethyl-[1,3]dioxan-2-yl)-ethyl]-benzoic acid isopropyl ester | | 570.52 (M + H) |
| Ib.29 | 2-{2-[2-(2-{3-[(E)-2-(7-Chloro-quinolin-2-yl)-vinyl]-phenyl}-[1,3]dioxolan-2-yl)-ethyl]-phenyl}-propan-2-ol | | 500.46 (M + H) |
| Ib.30 | {2-[2-(2-{3-[(E)-2-(7-Chloro-quinolin-2-yl)-vinyl]-phenyl}-[1,3]dioxolan-2-yl)-ethyl]-phenyl}-piperidin-1-yl-methanone | | 553.19 (M + H) |

TABLE 2-continued

Compounds of Formula (Ib) and (Ic)

| S. No. | Name | Sign of Rotation | Mass (+) |
|---|---|---|---|
| Ib.31 | 2-[2-(2-{3-[(E)-2-(7-Chloro-quinolin-2-yl)-vinyl]-phenyl}-[1,3]dioxolan-2-yl)-ethyl]-N,N-dipropyl-benzamide | | 569.45 (M + H) |
| Ib.32 | {2-[2-(2-{3-[(E)-2-(7-Chloro-quinolin-2-yl)-vinyl]-phenyl}-[1,3]dioxolan-2-yl)-ethyl]-phenyl}-morpholin-4-yl-methanone | | 555.17 (M + H) |
| Ib.33 | 2-[2-(2-{3-[(E)-2-(7-Chloro-quinolin-2-yl)-vinyl]-phenyl}-[1,3]dioxolan-2-yl)-ethyl]-isopropyl-N-methyl-benzamide | | 541.21 (M + H) |
| Ib.34 | 2-[2-(2-{3-[(E)-2-(7-Chloro-quinolin-2-yl)-vinyl]-phenyl}-[1,3]dioxolan-2-yl)-ethyl]-N-ethyl-N-methyl-benzamide | | 527.40 (M + H) |
| Ib.35 | 2-[2-(2-{3-[(E)-2-(7-Chloro-quinolin-2-yl)-vinyl]-phenyl}-[1,3]dioxolan-2-yl)-ethyl]-N,N-diethyl-benzamide | | 541.17 (M + H) |
| Ib.36 | {2-[2-(2-{3-[(E)-2-(7-Chloro-quinolin-2-yl)-vinyl]-phenyl}-[1,3]dioxolan-2-yl)-ethyl]-phenyl}-pyrrolidin-1-yl-methanone | | 539.12 (M + H) |
| Ib.37 | {2-[2-(2-{3-[(E)-2-(7-Chloro-quinolin-2-yl)-vinyl]-phenyl}-[1,3]dioxolan-2-yl)-ethyl]-phenoxy}-acetic acid 2-hydroxy-ethyl ester | | 560.37 (M + H) |
| Ib.38 | 2-[2-(2-{3-[(E)-2-(7-Chloro-quinolin-2-yl)-vinyl]-phenyl}-[1,3]dioxolan-2-yl)-ethyl]-phenoxy}-acetic acid | | 516.34 (M + H) |
| Ib.39 | 2-(2-{3-[(E)-2-(7-Chloro-quinolin-2-yl)-vinyl]-phenyl}-5,5-dimethyl-[1,3]dioxan-2-ylmethylsulfanyl)-benzoic acid | | 546.31 (M + H) |
| Ib.40 | 2-[2-(2-{3-[(E)-2-(7-Chloro-quinolin-2-yl)-vinyl]-phenyl}-[1,3]dioxolan-2-yl)-ethyl]-6-methyl-benzoic acid ethyl ester | | 528.36 (M + H) |
| Ib.41 | 2-(2-{3-[(E)-2-(7-Chloro-quinolin-2-yl)-vinyl]-phenyl}-[1,3]dioxolan-2-ylmethylsulfanyl)-benzoic acid methyl ester | | 518.30 (M + H) |
| Ib.42 | 2-(2-{3-[(E)-2-(7-Chloro-quinolin-2-yl)-vinyl]-phenyl}-[1,3]dioxolan-2-ylmethylsulfanyl)-benzoic acid | | 504.29 (M + H) |
| Ib.43 | 2-(2-{3-[(E)-2-(7-Chloro-quinolin-2-yl)-vinyl]-phenyl}-[1,3]dioxolan-2-ylmethylsulfanyl)-benzoic acid ethyl ester | | 532.33 (M + H) |
| Ib.44 | 4-[2-(2-{3-[(E)-2-(7-Chloro-quinolin-2-yl)-vinyl]-phenyl}-[1,3]dioxolan-2-yl)-ethyl]-benzoic acid ethyl ester | | — |
| Ib.45 | 2-{2-[2-(2-{3-[(E)-2-(7-Chloro-quinolin-2-yl)-vinyl]-phenyl}-[1,3]dioxolan-2-yl)-ethyl]-phenoxy}-1-pyrrolidin-1-yl-ethanone | | 569.11 (M + H) |
| Ib.46 | 3-[2-(2-{3-[(E)-2-(7-Chloro-quinolin-2-yl)-vinyl]-phenyl}-[1,3]dioxolan-2-yl)-ethyl]-benzoic acid ethyl ester | | 514.39 (M + H) |
| Ib.47 | 2-[2-(2-{3-[(E)-2-(7-Chloro-quinolin-2-yl)-vinyl]-phenyl}-[1,3]dioxolan-2-yl)-ethyl]-4-fluoro-benzoic acid ethyl ester | | 532.36 (M + H) |
| Ib.48 | 3-[2-(2-{3-[(E)-2-(7-Chloro-quinolin-2-yl)-vinyl]-phenyl}-[1,3]dioxolan-2-yl)-ethyl]-benzoic acid | | 486.37 (M + H) |
| Ib.49 | 2-[2-(2-{3-[(E)-2-(7-Chloro-quinolin-2-yl)-vinyl]-phenyl}-[1,3]dioxolan-2-yl)-ethyl]-4-fluoro-benzoic acid | | 504.35 (M + H) |
| Ib.50 | N-{2-[2-(2-{3-[(E)-2-(7-Chloro-quinolin-2-yl)-vinyl]-phenyl}-[1,3]dioxolan-2-yl)-ethyl]-benzyl}-succinamic acid | | 571.08 (M + H) |
| Ib.51 | N-{2-[2-(2-{3-[(E)-2-(7-Chloro-quinolin-2-yl)-vinyl]-phenyl}-[1,3]dioxolan-2-yl)-ethyl]-benzyl}-phthalamic acid | | 619.12 (M + H) |
| Ib.52 | 1-{2-[2-(2-{3-[(E)-2-(7-Chloro-quinolin-2-yl)-vinyl]-phenyl}-[1,3]dioxolan-2-yl)-ethyl]-benzyl}-piperidine-4-carboxylic acid ethyl ester | | 611.17 (M + H) |
| Ib.53 | 1-{2-[2-(2-{3-[(E)-2-(7-Chloro-quinolin-2-yl)-vinyl]-phenyl}-[1,3]dioxolan-2-yl)-ethyl]-benzyl}-piperidine-4-carboxylic acid | | 583.38 (M + H) |
| Ib.54 | 2-[2-(2-{3-[(E)-2-(7-Chloro-quinolin-2-yl)-vinyl]-phenyl}-5,5-dimethyl-[1,3]dioxan-2-yl) ethyl]-4-fluoro-benzoic acid ethyl ester | | 574.39 (M + H) |
| Ib.55 | 2-[2-(2-{3-[(E)-2-(7-Chloro-quinolin-2-yl)-vinyl]-phenyl}-[1,3]dioxolan-2-yl)-ethyl]-5-fluoro-benzoic acid ethyl ester | | 532.31 (M + H) |

TABLE 2-continued

Compounds of Formula (Ib) and (Ic)

| S. No. | Name | Sign of Rotation | Mass (+) |
|---|---|---|---|
| Ib.56 | 2-[2-(2-{3-[(E)-2-(7-Chloro-quinolin-2-yl)-vinyl]-phenyl}-[1,3]dioxan-2-yl)-ethyl]-4-fluoro-benzoic acid ethyl ester | | 546.33 (M + H) |
| Ib.57 | 2-[2-(2-{3-[(E)-2-(7-Chloro-quinolin-2-yl)-vinyl]-phenyl}-[1,3]dioxan-2-yl)-ethyl]-4-fluoro-benzoic acid | | 518.35 (M + H) |
| Ib.58 | 2-[2-(2-{3-[(E)-2-(7-Chloro-quinolin-2-yl)-vinyl]-phenyl}-[1,3]oxathiolan-2-yl)-ethyl]-benzoic acid methyl ester | ± | 516.33 (M + H) |
| Ib.59 | 2-[2-(2-{3-[(E)-2-(7-Chloro-quinolin-2-yl)-vinyl]-phenyl}-[1,3]oxathiolan-2-yl)-ethyl]-benzoic acid | ± | 502.32 (M + H) |
| Ib.60 | 2-[2-(2-{3-[(E)-2-(7-Chloro-quinolin-2-yl)-vinyl]-phenyl}-[1,3]oxathiolan-2-yl)-ethyl]-benzoic acid ethyl ester | ± | 530.34 (M + H) |
| Ib.61 | 2-[2-(2-{3-[(E)-2-(7-Chloro-quinolin-2-yl)-vinyl]-phenyl}-[1,3]dioxolan-2-yl)-ethyl]-5-hydroxy-benzoic acid ethyl ester | | 530.34 (M + H) |
| Ib.62 | 2-[2-(2-{3-[(E)-2-(7-Chloro-quinolin-2-yl)-vinyl]-phenyl}-[1,3]dioxolan-2-yl)-ethyl]-5-methoxy-benzoic acid ethyl ester | | 544.36 (M + H) |
| Ib.63 | 5-Acetoxy-2-[2-(2-{3-[(E)-2-(7-chloro-quinolin-2-yl)-vinyl]-phenyl}-[1,3]dioxolan-2-yl)-ethyl]-benzoic acid ethyl ester | | 572.34 (M + H) |
| Ib.64 | 2-[2-(2-{3-[(E)-2-(7-Chloro-quinolin-2-yl)-vinyl]-phenyl}-[1,3]dioxolan-2-yl)-ethyl]-5-hydroxy-benzoic acid | | 502.32 (M + H) |
| Ib.65 | 1-{2-[2-(2-{3-[(E)-2-(7-Chloro-quinolin-2-yl)-vinyl]-phenyl}-5,5-dimethyl-[1,3]dioxan-2-yl)-ethyl]-benzyl}-piperidine-4-carboxylic acid ethyl ester | | 653.17 (M + H) |
| Ib.66 | 1-{2-[2-(2-{3-[(E)-2-(7-Chloro-quinolin-2-yl)-vinyl]-phenyl}-5,5-dimethyl-[1,3]dioxan-2-yl)-ethyl]-benzyl}-piperidine-4-carboxylic acid | | 625.20 (M + H) |
| Ib.67 | 2-[2-(2-{3-[(E)-2-(7-Chloro-quinolin-2-yl)-vinyl]-phenyl}-[1,3]dioxolan-2-yl)-ethyl]-5-methoxy-benzoic acid | | 516.37 (M + H) |
| Ib.68 | 2-[2-(2-{3-[(E)-2-(7-Chloro-quinolin-2-yl)-vinyl]-phenyl}-[1,3]dioxolan-2-yl)-vinyl]-benzoic acid methyl ester | | 498.33 (M + H) |
| Ib.69 | 2-[2-(2-{3-[(E)-2-(7-Chloro-quinolin-2-yl)-vinyl]-phenyl}-[1,3]dioxolan-2-yl)-vinyl]-benzoic acid | | 484.36 (M + H) |
| Ib.70 | 2-{2-[2-(2-{3-[(E)-2-(7-Chloro-quinolin-2-yl)-vinyl]-phenyl}-[1,3]dioxolan-2-yl)-ethyl]-phenoxy}-butyric acid | ± | 544.36 (M + H) |
| Ib.71 | 2-{2-[2-(2-{3-[(E)-2-(7-Chloro-quinolin-2-yl)-vinyl]-phenyl}-5,5-dimethyl-[1,3]dioxan-2-yl)-ethyl]-phenoxy}-butyric acid ethyl ester | ± | 614.16 (M + H) |
| Ib.72 | 2-{2-[2-(2-{3-[2-(7-Chloro-quinolin-2-yl)-vinyl]-phenyl}-5,5-dimethyl-[1,3]dioxan-2-yl)-ethyl]-phenoxy}-butyric acid | ± | 586.40 (M + H) |
| Ib.73 | 2-{2-[2-(2-{3-[(E)-2-(7-Chloro-quinolin-2-yl)-vinyl]-phenyl}-5,5-dimethyl-[1,3]dioxan-2-yl)-ethyl]-benzyloxy}-benzoic acid ethyl ester | | 648.43 (M + H) |
| Ib.74 | 2-{2-[2-(2-{3-[(E)-2-(7-Chloro-quinolin-2-yl)-vinyl]-phenyl}-5,5-dimethyl-[1,3]dioxan-2-yl)-ethyl]-benzyloxy}-benzoic acid | | 634.58 (M + H) |
| Ib.75 | 2-{2-[2-(2-{3-[(E)-2-(7-Chloro-quinolin-2-yl)-vinyl]-phenyl}-[1,3]dioxolan-2-yl)-ethyl]-benzyloxy}-benzoic acid methyl ester | | 606.53 (M + H) |
| Ib.76 | 2-{2-[2-(2-{3-[(E)-2-(7-Chloro-quinolin-2-yl)-vinyl]-phenyl}-[1,3]dioxolan-2-yl)-ethyl]-benzyloxy}-benzoic acid | | 592.55 (M + H) |
| Ib.77 | 2-[2-(2-{3-[(E)-2-(7-Chloro-quinolin-2-yl)-vinyl]-phenyl}-[1,3]dioxolan-2-yl)-vinyl]-5-hydroxy-benzoic acid ethyl ester | | 528.41 (M + H) |
| Ib.78 | 2-[2-(2-{3-[(E)-2-(7-Chloro-quinolin-2-yl)-vinyl]-phenyl}-[1,3]dioxolan-2-yl)-vinyl]-5-hydroxy-benzoic acid | | 500.36 (M + H) |
| Ib.79 | 2-[2-(2-{3-[(E)-2-(7-Chloro-quinolin-2-yl)-vinyl]-phenyl}-[1,3]dioxolan-2-yl)-vinyl]-5-methoxy-benzoic acid | | 514.41 (M + H) |
| Ib.80 | 2-[2-(2-{3-[(E)-2-(7-Chloro-quinolin-2-yl)-vinyl]-phenyl}-[1,3]dioxolan-2-yl)-ethyl]-5-iso-propoxy-benzoic acid | | 544.45 (M + H) |

TABLE 2-continued

Compounds of Formula (Ib) and (Ic)

| S. No. | Name | Sign of Rotation | Mass (+) |
|---|---|---|---|
| Ib.81 | 2-[2-(2-{3-[(E)-2-(7-Chloro-quinolin-2-yl)-vinyl]-phenyl}-[1,3]dioxolan-2-yl)-ethyl]-5-propoxy-benzoic acid | | 544.46 (M + H) |
| Ib.82 | 5-Butoxy-2-[2-(2-{3-[(E)-2-(7-chloro-quinolin-2-yl)-vinyl]-phenyl}-[1,3]dioxolan-2-yl)-ethyl]-benzoic acid | | 558.42 (M + H) |
| Ib.83 | 2-{2-[2-(2-{3-[(E)-2-(7-Chloro-quinolin-2-yl)-vinyl]-phenyl}-[1,3]dioxolan-2-yl)-ethyl]-phenyl}-isobutyramide | | 527.25 (M + H) |
| Ib.84 | 2-[2-(2-{3-[(E)-2-(7-Chloro-quinolin-2-yl)-vinyl]-phenyl}-[1,3]dioxolan-2-yl)-ethyl]-5-pentyl-oxy-benzoic acid | | 572.28 (M + H) |
| Ib.85 | 2-[2-(2-{3-[(E)-2-(7-Chloro-quinolin-2-yl)-vinyl]-phenyl}-[1,3]dioxolan-2-yl)-ethyl]-5-cyclopentyloxy-benzoic acid | | 570.25 (M + H) |
| Ib.86 | 2-[2-(2-{3-[(E)-2-(7-Chloro-quinolin-2-yl)-vinyl]-phenyl}-[1,3]dioxolan-2-yl)-ethyl]-5-ethoxy-benzoic acid | | 530.20 (M + H) |
| Ib.87 | 2-[2-(2-{3-[(E)-2-(7-Chloro-quinolin-2-yl)-vinyl]-phenyl}-[1,3]dioxolan-2-yl)-ethyl]-5-cyclo-hexyloxy-benzoic acid | | 584.18 (M + H) |
| Ib.88 | 2-[2-(2-{3-[(E)-2-(7-Chloro-quinolin-2-yl)-vinyl]-phenyl}-[1,3]dioxolan-2-yl)-ethyl]-5-fluoro-benzoic acid | | 504.08 (M + H) |
| Ib.89 | 5-Benzyloxy-2-[2-(2-{3-[(E)-2-(7-chloro quinolin-2-yl)-vinyl]-phenyl}-[1,3]dioxolan-2-yl)-ethyl-benzoic acid | | 592.17 (M + H) |
| Ib.90 | 2-{2-[2-(2-{3-[(E)-2-(7-Chloro-quinolin-2-yl)-vinyl]-phenyl}-[1,3]dioxolan-2-yl)-ethyl]-phenyl}-propionic acid | ± | 514.18 (M + H) |
| Ib.91 | 2-{2-[2-(2-{3-[(E)-2-(7-Chloro-quinolin-2-yl)-vinyl]-phenyl}-5,5-dimethyl-[1,3]dioxan-2-yl)-ethyl]-phenyl}-propionic acid | ± | 556.13 (M + H) |
| Ib.92 | 5-[2-(2-{3-[(E)-2-(7-Chloro-quinolin-2-yl)-vinyl]-phenyl}-[1,3]dioxolan-2-yl)-ethyl]-2-methoxy-benzoic acid | | 516.15 (M + H) |
| Ib.93 | 2-[2-(2-{3-[(E)-2-(7-Chloro-quinolin-2-yl)-vinyl]-phenyl}-[1,3]dioxolan-2-yl)-ethyl]-5-prop-2-ynyloxy-benzoic acid | | 540.18 (M + H) |
| Ib.94 | 2-[2-(2-{3-[(E)-2-(7-Chloro-quinolin-2-yl)-vinyl]-phenyl}-[1,3]dioxolan-2-yl)-ethyl]-5-cyclo-propylmethoxy-benzoic acid | | 556.06 (M + H) |
| Ib.95 | 2-(3-{3-[(E)-2-(7-Chloro-quinolin-2-yl)-vinyl]-phenyl}-3,3-dimethoxy-propyl)-benzoic acid | | 456.08 (M − 32) |
| Ib.96 | 2-(3-{3-[(E)-2-(7-Chloro-quinolin-2-yl)-vinyl]-phenyl}-3,3-diethoxy-propyl)-benzoic acid | | 502.27 (M − 14) |
| Ib.97 | 2-(3-{3-[(E)-2-(7-Chloro-quinolin-2-yl)-vinyl]-phenyl}-3,3-diethoxy-propyl)-5-methoxy-benzoic acid | | 486.04 (M − 60) |
| Ib.98 | 4-Chloro-2-[2-(2-{3-[(E)-2-(7-chloro-quinolin-2-yl)-vinyl]-phenyl}-[1,3]dioxolan-2-yl)-ethyl]-benzoic acid | | 520.24 (M + H) |
| Ib.99 | 2-[2-(2-{3-[(E)-2-(7-Chloro-quinolin-2-yl)-vinyl]-phenyl}-[1,3]dioxolan-2-yl)-ethyl]-5-nitro-benzoic acid | | 531.25 (M + H) |
| Ib.100 | 2-(3-{3-[(E)-2-(7-Chloro-quinolin-2-yl)-vinyl]-phenyl}-3,3-dimethoxy-propyl)-5-methoxy-benzoic acid | | 472.28 (M + 1 − 46) |
| Ib.101 | [2-(3-{3-[(E)-2-(7-Chloro-quinolin-2-yl)-vinyl]-phenyl}-3,3-diethoxy-propyl)-phenyl]-acetic acid | | 516.36 (M + 1 − 15) |
| Ib.102 | 2-[2-(2-{3-[(E)-2-(7-Chloro-quinolin-2-yl)-vinyl]-phenyl}-[1,3]dioxolan-2-yl)-ethyl]-4-methoxy-benzoic acid | | 516.34 (M + H) |
| Ib.103 | 2-[2-(2-{3-[(E)-2-(7-Chloro-quinolin-2-yl)-vinyl]-phenyl}-[1,3]dioxolan-2-yl)-ethyl]-4,5-dimethoxy-benzoic acid | | 546.35 (M + H) |
| Ib.104 | [2-(3-{3-[(E)-2-(7-Chloro-quinolin-2-yl)-vinyl]-phenyl}-3,3-dimethoxy-propyl)-phenyl]-acetic acid | | 502.13 (M + H) |
| Ib.105 | 2-[2-(2-{3-[(E)-2-(7-Chloro-quinolin-2-yl)-vinyl]-phenyl}-[1,3]dioxan-2-yl)-ethyl]-4,5-dimethoxy-benzoic acid | | 560.04 (M + H) |
| Ib.106 | 2-(3-{3-[(E)-2-(7-Chloro-quinolin-2-yl)-vinyl]-phenyl}-3,3-dimethoxy-propyl)-4,5-dimethoxy-benzoic acid | | 548.09 (M + H) |

TABLE 2-continued

Compounds of Formula (Ib) and (Ic)

| S. No. | Name | Sign of Rotation | Mass (+) |
|---|---|---|---|
| Ib.107 | 3-[2-(2-{3-[(E)-2-(7-Chloro-quinolin-2-yl)-vinyl]-phenyl}-[1,3]dioxolan-2-yl)-ethyl]-4-methoxy-benzoic acid | | 516.09 (M + H) |
| Ib.108 | 2-(3-{3-[(E)-2-(7-Chloro-quinolin-2-yl)-vinyl]-phenyl}-3,3-diethoxy-propyl)-4,5-dimethoxy-benzoic acid | | 516.11 (M + 1 − 60) |
| Ib.109 | 5-Chloro-2-(3-{3-[(E)-2-(7-chloro-quinolin-2-yl)-vinyl]-phenyl}-3,3-dimethoxy-propyl)-benzoic acid | | 522.06 (M + H) |
| Ib.110 | 5-Chloro-2-(3-{3-[(E)-2-(7-chloro-quinolin-2-yl)-vinyl]-phenyl}-3,3-diethoxy-propyl)-benzoic acid | | 522.04 (M + 1 − 28) |
| Ib.111 | 5-Chloro-2-[2-(2-{3-[(E)-2-(7-chloro-quinolin-2-yl)-vinyl]-phenyl}-[1,3]dioxolan-2-yl)-ethyl}-benzoic acid | | 520.06 (M + H) |
| Ib.112 | 5-Chloro-2-[2-(2-{3-[(E)-2-(7-chloro-quinolin-2-yl)-vinyl]-phenyl}-5,5-dimethyl-[1,3]dioxan-2-yl)-ethyl]-benzoic acid | | 562.03 (M + H) |
| Ib.113 | 2-[2-(2-{3-[(E)-2-(7-Chloro-quinolin-2-yl)-vinyl]-phenyl}-[1,3]dioxolan-2-yl)-ethyl]-3,4,5-trimethoxy-benzoic acid | | 576.04 (M + H) |
| Ib.114 | 2-(3-{3-[(E)-2-(7-Chloro-quinolin-2-yl)-vinyl]-phenyl}-3,3-dimethoxy-propyl)-3,4,5-tri-methoxy-benzoic acid | | 532.05 (M + 1 − 46) |
| Ib.115 | 5-Chloro-2-[2-(2-{3-[(E)-2-(7-chloro-quinolin-2-yl)-vinyl]-phenyl}-[1,3]dioxan-2-yl)-ethyl]-benzoic acid | | 534.05 (M + H) |
| Ib.116 | 2-[2-(2-{3-[(E)-2-(7-Chloro-quinolin-2-yl)-vinyl]-phenyl}-5,5-dimethyl-[1,3]dioxan-2-yl)-ethyl]-5-methyl-benzoic acid | | 542.11 (M + H) |
| Ib.117 | 2-[2-(2-{3-[(E)-2-(7-Chloro-quinolin-2-yl)-vinyl]-phenyl}-[1,3]dioxolan-2-yl)-ethyl]-5-methyl-benzoic acid | | 500.13 (M + H) |
| Ib.118 | 2-(3-{3-[(E)-2-(7-Chloro-quinolin-2-yl)-vinyl]-phenyl}-3,3-dimethoxy-propyl)-5-methyl-benzoic acid | | 502.11 (M + H) |
| Ib.119 | 2-[2-(2-{3-[(E)-2-(7-Chloro-quinolin-2-yl)-vinyl]-phenyl}-[1,3]dioxolan-2-yl)-ethyl]-5-methyl-benzoic acid | | 514.12 (M + H) |
| Ib.120 | 2-[2-(2-{3-[(E)-2-(7-Chloro-quinolin-2-yl)-vinyl]-phenyl}-[1,3]dioxolan-2-yl)-ethyl]-5-trifluoro-methoxybenzoic acid | | 570.06 (M + H) |
| Ib.121 | 2-[2-(2-{3-[(E)-2-(7-Chloro-quinolin-2-yl)-vinyl]-phenyl}-5,5-dimethyl-[1,3]dioxan-2-yl)-ethyl]-5-trifluoro-methoxy-benzoic acid | | 612.10 (M + H) |
| Ib.122 | 2-[2-(2-{3-[(E)-2-(7-Chloro-quinolin-2-yl)-vinyl]-phenyl}-[1,3]dioxolan-2-yl)-ethyl]-5-methoxy-4-nitro-benzoic acid | | 561.03 (M + H) |
| Ib.123 | 2-[2-(2-{3-[(E)-2-(7-Chloro-quinolin-2-yl)-vinyl]-phenyl}-[1,3]dioxan-2-yl)-ethyl]-5-methoxy-4-nitro-benzoic acid | | 575.04 (M + H) |
| Ib.124 | 2-[2-(2-{3-[(E)-2-(7-Chloro-quinolin-2-yl)-vinyl]-phenyl}-[1,3]dioxolan-2-yl)-ethyl]-4,5-difluoro-benzoic acid | | 522.08 (M + H) |
| Ib.125 | 2-[2-(2-{3-[(E)-2-(7-Chloro-quinolin-2-yl)-vinyl]-phenyl}-[1,3]dioxan-2-yl)-ethyl]-4,5-difluoro-benzoic acid | | 536.03 (M + H) |
| Ib.126 | 2-[2-(2-{3-[(E)-2-(7-Chloro-quinolin-2-yl)-vinyl]-phenyl}-5,5-dimethyl-[1,3]dioxan-2-yl)-ethyl]-4,5-difluoro-benzoic acid | | 564.10 (M + H) |
| Ib.127 | 6-[2-(2-{3-[(E)-2-(7-Chloro-quinolin-2-yl)-vinyl]-phenyl}-[1,3]dioxolan-2-yl)-ethyl]-3-methoxy-2-nitro-benzoic acid | | 561.08 (M + H) |
| Ib.128 | 2-(3-{3-[(E)-2-(7-Chloro-quinolin-2-yl)-vinyl]-phenyl}-3,3-dimethoxy-propyl)-4,5-difluoro-benzoic acid | | 492.06 (M + H − 32) |
| Ib.129 | 2-(3-{3-[(E)-2-(7-Chloro-quinolin-2-yl)-vinyl]-phenyl}-3,3-diethoxy-propyl)-4,5-difluoro-benzoic acid | | 478.04 (M + 1 − 76) |
| Ib.130 | 2-[2-(2-{3-[(E)-2-(7-Chloro-quinolin-2-yl)-vinyl]-phenyl}-[1,3]dioxolan-2-yl)-ethyl]-5-methane-sulfonyl-benzoic acid | | 564.03 (M + H) |
| Ib.131 | 2-[2-(2-{3-[(E)-2-(7-Chloro-quinolin-2-yl)-vinyl]-phenyl}-[1,3]dioxan-2-yl)-ethyl]-5-methane-sulfonyl-benzoic acid | | 578.06 (M + H) |
| Ib.132 | 6-[2-(2-{3-[(E)-2-(7-Chloro-quinolin-2-yl)-vinyl]-phenyl}-[1,3]dioxolan-2-yl)-ethyl]-benzo[1,3]dioxole-5-carboxylic acid | | 530.06 (M + H) |

TABLE 2-continued

Compounds of Formula (Ib) and (Ic)

| S. No. | Name | Sign of Rotation | Mass (+) |
|---|---|---|---|
| Ib.133 | 6-[2-(2-{3-[(E)-2-(7-Chloro-quinolin-2-yl)-vinyl]-phenyl}-[1,3]dioxan-2-yl)-ethyl]-benzo[1,3] dioxole-5-carboxylic acid | | 544.09 (M + H) |
| Ib.134 | 6-(3-{3-[(E)-2-(7-Chloro-quinolin-2-yl)-vinyl]-phenyl}-3,3-dimethoxy-propyl)-benzo[1,3] dioxole-5-carboxylic acid | | 486.04 (M + H − 46) |
| Ib.135 | 7-Chloro-2-{(E)-2-[3-(2-{2-[4-methoxy-2-(1H-tetrazol-5-yl)-phenyl]-ethyl}-[1,3]dioxolan-2-yl)-phenyl]-vinyl}-quinoline | | 540.10 (M + H) |
| Ib.136 | 2-[2-(2-{3-[(E)-2-(7-Chloro-quinolin-2-yl)-vinyl]-phenyl}-[1,3]dioxolan-2-yl)-ethyl]-5-ethyl-benzoic acid | | 514.12 (M + H) |
| Ib.137 | 2-[2-(2-{3-[(E)-2-(7-Chloro-quinolin-2-yl)-vinyl]-phenyl}-5,5-dimethyl-[1,3]dioxan-2-yl)-ethyl]-5-ethyl-benzoic acid | | 556.14 (M + H) |
| Ib.138 | 2-[2-(2-{3-[(E)-2-(7-Chloro-quinolin-2-yl)-vinyl]-phenyl}-[1,3]dioxan-2-yl)-ethyl]-5-ethyl-benzoic acid | | 528.05 (M + H) |
| Ib.139 | 7-[2-(2-{3-[(E)-2-(7-Chloro-quinolin-2-yl)-vinyl]-phenyl}-[1,3]dioxolan-2-yl)-ethyl]-2,3-dihydrobenzo[1,4]dioxine-6-carboxylic acid | | 544.08 (M + H) |
| Ib.140 | 7-[2-(2-{3-[(E)-2-(7-Chloro-quinolin-2-yl)-vinyl]-phenyl}-[1,3]dioxan-2-yl)-ethyl]-2,3-dihydro-benzo[1,4]dioxine-6-carboxylic acid | | 558.08 (M + H) |
| Ib.141 | 5-Allyloxy-2-[2-(2-{3-[(E)-2-(7-chloro-quinolin-2-yl)-vinyl]-phenyl}-[1,3]dioxolan-2-yl)-ethyl]-benzoic acid | | 542.09 (M + H) |
| Ib.142 | 2-[2-(2-{3-[(E)-2-(7-Chloro-quinolin-2-yl)-vinyl]-phenyl}-[1,3]dioxolan-2-yl)-ethyl]-terephthalic acid | | 530.05 (M + H) |
| Ib.143 | 2-[2-(2-{3-[(E)-2-(7-Chloro-quinolin-2-yl)-vinyl]-phenyl}-[1,3]dioxan-2-yl)-ethyl]-terephthalic acid | | 544.06 (M + H) |
| Ib.144 | 2-(3-{3-[(E)-2-(7-Chloro-quinolin-2-yl)-vinyl]-phenyl}-3,3-dimethoxy-propyl)-terephthalic acid | | 500.03 (M + H − 32) |
| Ib.145 | 2-(3-{3-[(E)-2-(7-Chloro-quinolin-2-yl)-vinyl]-phenyl}-3-ethoxyimino-propyl)-benzoic acid | | 485.08 (M + H) |
| Ib.146 | 2-(3-{3-[(E)-2-(7-Chloro-quinolin-2-yl)-vinyl]-phenyl}-3-methoxyimino-propyl)-benzoic acid | | 471.07 (M + H) |
| Ib.147 | 2-(3-{3-[(E)-2-(7-Chloro-quinolin-2-yl)-vinyl]-phenyl}-3-methoxyimino-propyl)-5-methoxy-benzoic acid | | 501.09 (M + H) |
| Ib.148 | 2-{1-{3-[(E)-2-(7-Chloro-quinolin-2-yl)-vinyl]-phenyl}-3-[2-(1-hydroxy-1-methyl-ethyl)-phenyl]-propylideneamino-oxy}-propionic acid | ± | 543.16 (M + H) |
| Ib.149 | 4-{1-{3-[(E)-2-(7-Chloro-quinolin-2-yl)-vinyl]-phenyl}-3-[2-(1-hydroxy-1-methyl-ethyl)-phenyl]-propylideneamino-oxy}-butyric acid | | 557.13 (M + H) |
| Ib.150 | 6-[2-(2-{3-[(E)-2-(7-Chloro-quinolin-2-yl)-vinyl]-phenyl}-[1,3]dioxolan-2-yl)-ethyl]-indan-5-carboxylic acid | | 526.10 (M + H) |
| Ib.151 | N-{2-[2-(2-{3-[(E)-2-(7-Chloro-quinolin-2-yl)-vinyl]-phenyl}-[1,3]dioxolan-2-yl)-ethyl]-5methoxy-benzoyl}-benzenesulfonamide | | 655.17 (M + H) |
| Ib.152 | N-{2-[2-(2-{3-[(E)-2-(7-Chloro-quinolin-2-yl)-vinyl]-phenyl}-[1,3]dioxolan-2-yl)-ethyl]-5-methoxy-benzoyl}-4-methylbenzenesulfonamide | | 669.10 (M + H) |
| Ib.153 | 6-[2-(2-{3-[(E)-2-(7-Chloro-quinolin-2-yl)-vinyl]-phenyl}-[1,3]dioxan-2-yl)-ethyl]-indan-5-carboxylic acid | | 540.18 (M + H) |
| Ib.154 | 6-(3-{3-[(E)-2-(7-Chloro-quinolin-2-yl)-vinyl]-phenyl}-3,3-dimethoxy-propyl)-indan-5-carboxylic acid | | 496.16 (M − 32) |
| Ib.155 | 6-(3-{3-[(E)-2-(7-Chloro-quinolin-2-yl)-vinyl]-phenyl}-3,3-diethoxy-propyl)-indan-5-carboxylic acid | | 496.15 (M − 60) |
| Ib.156 | 4-[2-(2-{3-[(E)-2-(7-Chloro-quinolin-2-yl)-vinyl]-phenyl}-[1,3]dioxolan-2-yl)-ethyl]-isophthalic acid | | 530.13 (M + H) |
| Ib.157 | N-{2-[2-(2-{3-[(E)-2-(7-Chloro-quinolin-2-yl)-vinyl]-phenyl}-[1,3]dioxolan-2-yl)-ethyl]-5-methoxy-benzoyl}-methanesulfonamide | | 593.15 (M + H) |
| Ib.158 | N-{2-[2-(2-{3-[(E)-2-(7-Chloro-quinolin-2-yl)-vinyl]-phenyl}-[1,3]dioxolan-2-yl)-ethyl]-5-methoxy-benzoyl}-4-fluoro-benzenesulfonamide | | 673.16 (M + H) |
| Ib.159 | 4-Chloro-N-{2-[(E)-2-(2-{3-[2-(7-chloro-quinolin-2-yl)-vinyl]-phenyl}-[1,3]dioxolan-2-yl)-ethyl]-5-methoxy-benzoyl}-benzene-sulfonamide | | 689.15 (M + H) |

TABLE 2-continued

Compounds of Formula (Ib) and (Ic)

| S. No. | Name | Sign of Rotation | Mass (+) |
|---|---|---|---|
| Ib.160 | 4-Bromo-N-{2-[(E)-2-(2-{3-[2-(7-chloro-quinolin-2-yl)-vinyl]-phenyl}-[1,3]dioxolan-2-yl)-ethyl]-5-methoxy-benzoyl}-benzene-sulfonamide | | 735.11 (M + H) |
| Ib.161 | N-{2-[2-(2-{3-[(E)-2-(7-Chloro-quinolin-2-yl)-vinyl]-phenyl}-[1,3]dioxolan-2-yl)-ethyl]-5-methoxy-benzoyl}-4-trifluoromethyl-benzenesulfonamide | | 723.17 (M + H) |
| Ib.162 | 2-[2-(2-{3-[(E)-2-(6,7-Difluoro-quinolin-2-yl)-vinyl]-phenyl}-[1,3]dioxolan-2-yl)-ethyl]-5-methoxy-benzoic acid | | 518.42 (M + H) |
| Ic.1 | (2-{3-[(E)-2-(7-Chloro-quinolin-2-yl)-vinyl]-phenyl}-2-ethoxy-ethylsulfanyl)-acetic acid | ± | 428.14 (M + H) |
| Ic.2 | (2-{3-[(E)-2-(7-Chloro-quinolin-2-yl)-vinyl]-phenyl}-2-ethoxy-ethoxy)-acetic acid | ± | |
| Ic.3 | (2-{3-[(E)-2-(7-Chloro-quinolin-2-yl)-vinyl]-phenyl}-[1,3]dioxolan-2-ylmethylsulfanyl)-acetic acid | | 442.14 (M + H) |

Representative synthetic methods and reaction conditions are described.

In one embodiment as depicted in Scheme 5, the ester-alcohol intermediate 21 was synthesized from known keto intermediate 20 and then 21 was treated with sulfuric acid in presence of acetonitrile and glacial acetic acid to give the amide 22 involving Ritter reaction. Subsequent acidic hydrolysis of 22 gave an intermediate amino acid 23. Usual esterification of the amino acid 23 gave ester intermediate 24 which on treatment with various electrophiles such as acid chlorides/acidanhydrides/isocyanates/carbamoylchlorides/thiocarbomoyl chlorides/alkyl halides/epoxides/sulphonylchlorides etc (FIG. 1) either in neutral or basic conditions given in general amide methods A, B or C resulted in various ester-amides, hydrolysis of which have given some derivatives shown in table 1. For example 23 directly reacts with some of the cyclic anhydrides such as succinic and phthalic anhydrides to give the di-acid derivatives such as (Ia.04) and (Ia.07) (table 1). In some cases the amino-acid intermediate 23 can directly be reacted with mixed anhydrides derived from caproic acid and pivolyl chloride to give the derivative such as (Ia.09).

Similarly, a known diol intermediate 25 was treated with methanesulfonyl chloride to get mono-mesylated product 26 and treatment of which with sodium azide gave the azido alcohol 27. Reduction of the azido group under triphenyl phosphine (TPP), water-dioxane yielded amino alcohol 28. Further reaction of this amin-ol 28 with different electrophiles as above (FIG. 1) gave some of the compounds described in table 1. For example treatment of 28 with 4,5-dichloro phthalic anhydride gave (Ia.58). When 28 reacted with chloroacetyl chloride resulted in 28a which on further treatment with thioglycollic acid gives a: nucleophilic displacement product (Ia.64). In a similar fashion when chloro-alkyl-amide ester 22a was treated with morpholin as nucleophile and subjected to further alkaline hydrolysis gave (Ia.16) as described in experimental section.

In one strategy, epoxide 30 required herein can be prepared by treating the known aldehyde 29 (JOC, 1989, 54, 3718-3721) in single step using Corey-Chaykowski reaction. Treatment of 30 with phenol 31 prepared from methyl salicylate as shown in the Scheme 6 to result in an oxa-diol 32 which in turn was treated as per the scheme (through azide mediation) to obtain amino-alcohol 35. Amino-alcohol 35 can also be directly obtained by treatment of the mesylate 33 with amine source such as HMTA. Intermediate 35 has been utilized for the synthesis of some of compounds related to Formula (Ia) (see table 1) such as (Ia.109).

Scheme 5

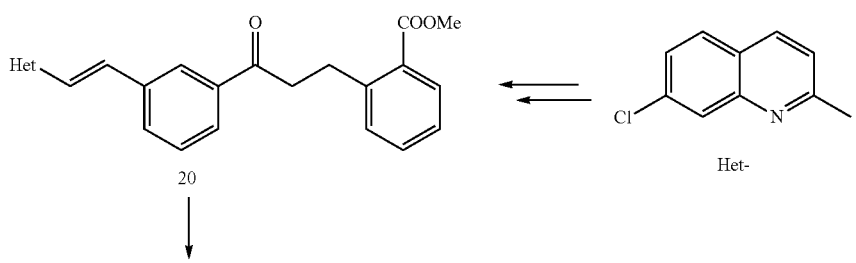

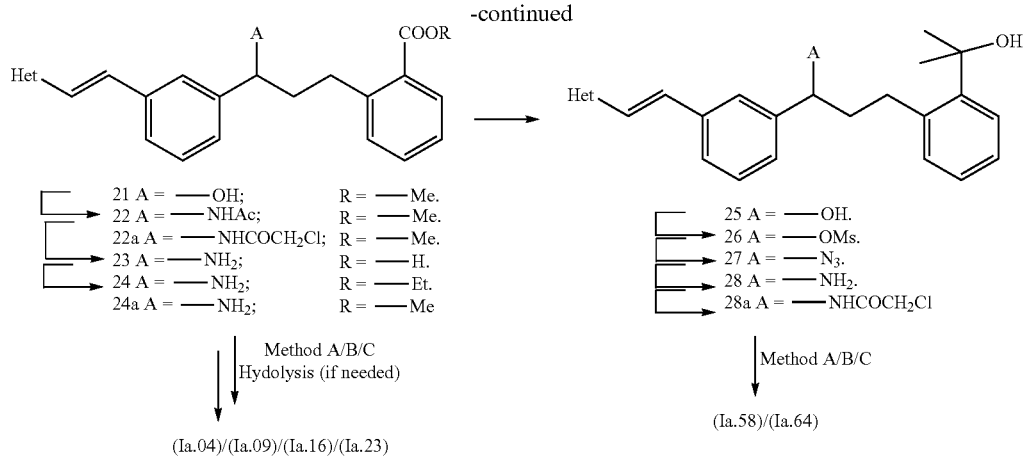
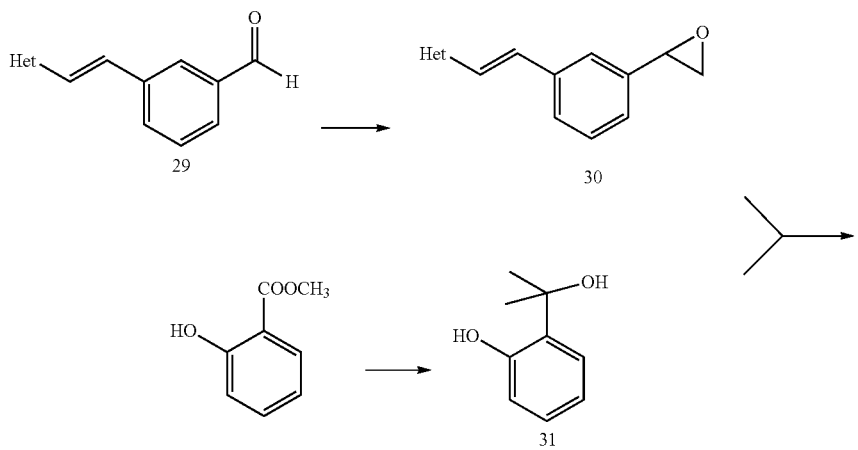
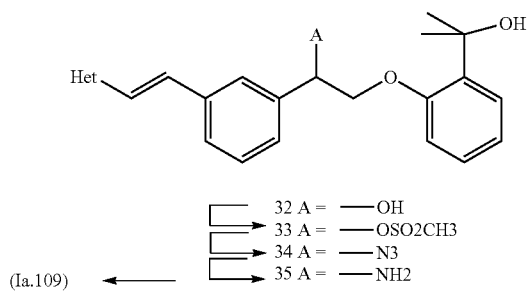
Some of the amide derivatives such as (Ia.38) and (Ia.75) were synthesized according to the Scheme 7 outlined.

Scheme 7

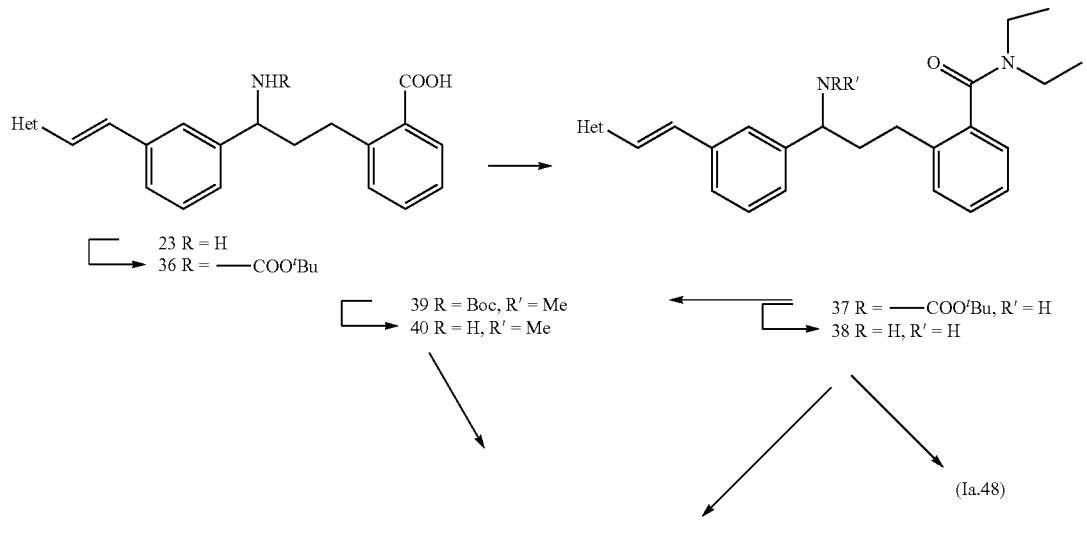

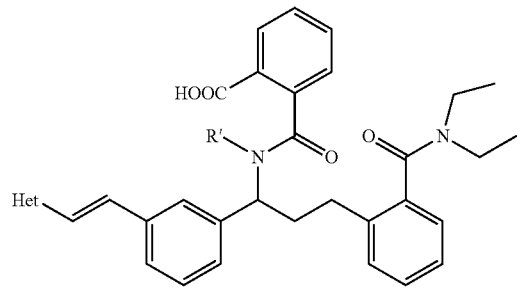

(Ia.38): R' = H
(Ia.75): R' = Me

When the amino acid 23 was protected as tert-butoxy carbonyl (boc) function and amidated under usual conditions to 37, followed by alkylation under basic conditions gave 39. After de-protection of 37 and 39, the resultant amine-amides 38 and 40 were treated with cyclic anhydride such as phthalic anhydride to achieve the compounds of interest. Further esterification of (Ia.38) renders (Ia.48) or otherwise 38 can be converted to (Ia 48) directly.

In another elaboration of the present invention, the ester-amide 22a obtained from Ritter reaction of 21 with chloroacetonitrile (refer scheme 5), was treated with nucleophiles such as morpholin to give the morpholino-ester which on hydrolysis gave the derivative such as (Ia.16).

To obtain the chiral derivatives the racemic amino ester 24/24a was subjected to resolution by fractional crystallization as a diastereomeric salt involving any of the chiral acids such as tartaric acid/camphor sulfonic acid/mandelic acid or any other chiral resolving agent in an appropriate solvent and at appropriate temperature in one or more crystallizations.

In another embodiment as shown in Scheme 8 the known keto ester 20 on acidic treatment with ethylene glycol/ethyl orthoformate in ethanol, to obtain, the cyclic/acyclic ketals 41 or 42 under azeotropic/reflux conditions followed by a base hydrolysis gave certain compounds presented in Formula Ib such as (Ib.04)/(Ib.96). In an extension of the present invention the acids so produced in scheme 8 were converted to amides/esters of choice according to the methods described earlier. The keto intermediate 20 was treat with hydroxylamine to obtain the oxime 43 followed by o-alkylation and concomitant hydrolysis gave the oxime-acids such as (Ib.145) described here in.

In this invention the ketals and ketoxime-ethers were tested for LTD4 binding assays and found to be of particular interest. Further this invention does not confine and may have an extension to those derivatives such as hydrazones also.

Scheme 8

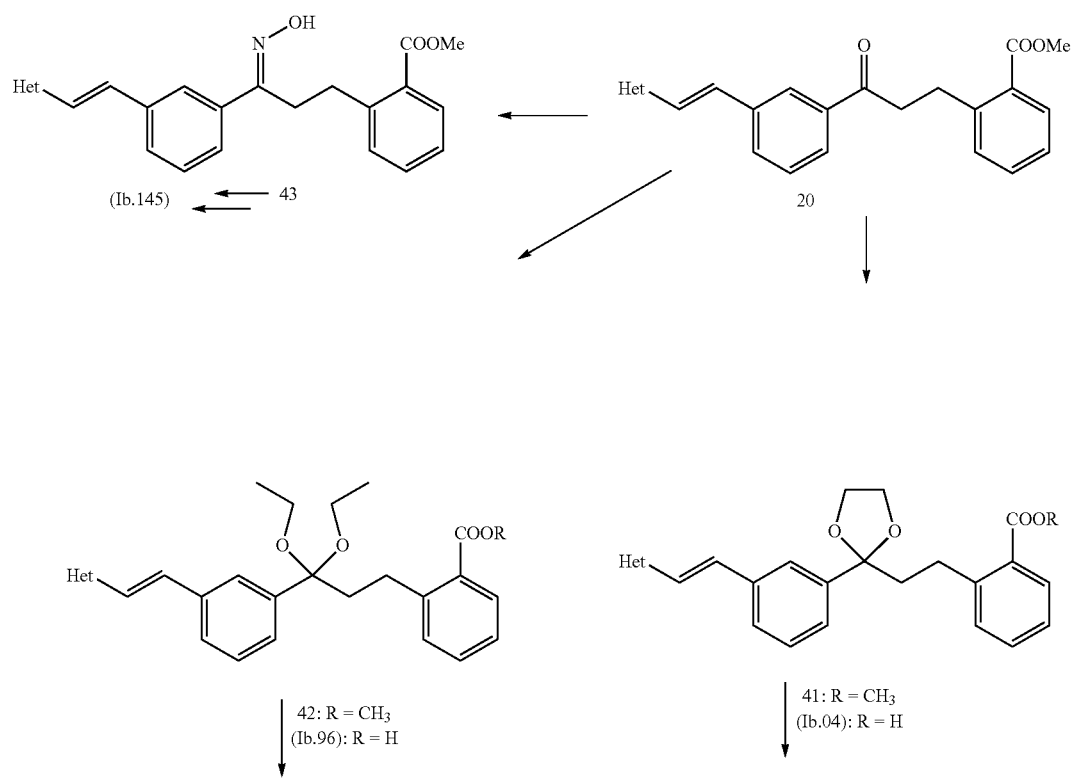

Previously described epoxide 30 was treated in glacial acetic acid/BF3-etherate in presence of various alcohols such as cyclopropyl methanol as outlined in the scheme 9 to obtain the racemic ethereal alcohol 44, which on treatment with methyl salicylate under Mitsunobu condition gave the ester 45. On hydrolysis 45 gave the derivative (Ia.96).

Under basic condition epoxide 30 was opened with thiosalicylate and the alcohol 46 was further oxidized (Swern) to get the intermediate 47 which was used in preparation of some of the derivatives such as (Ib.41). In a similar fashion aliphatic thioesters would open the epoxide 30 to give corresponding aliphatic derivatives (Formula 1c).

Scheme 9

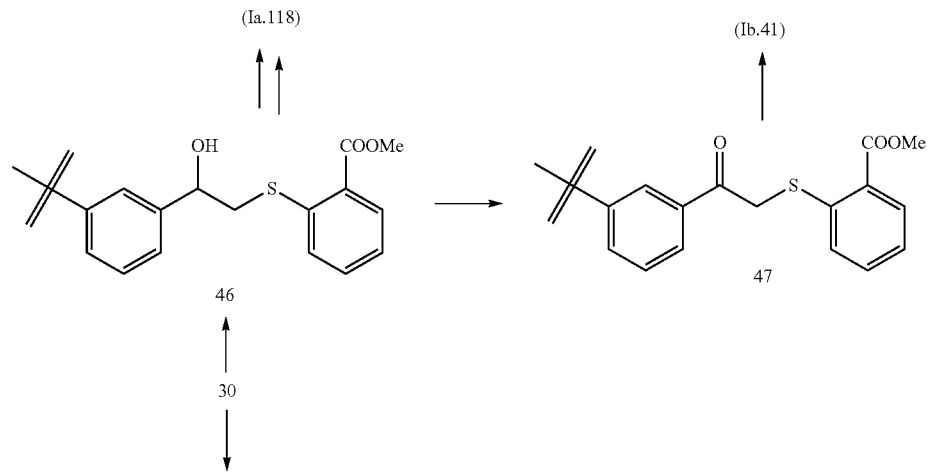

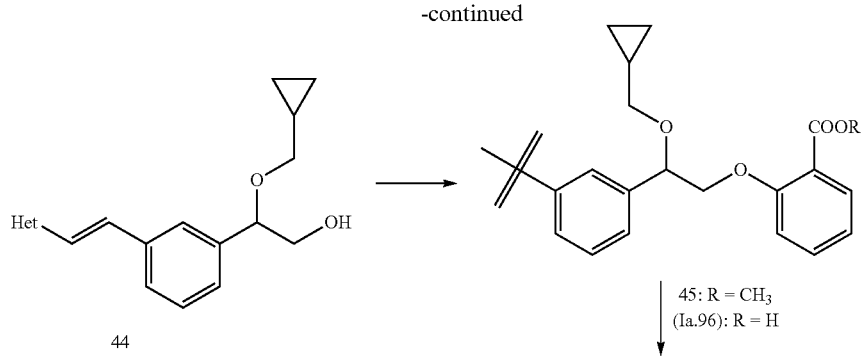

Ketal-amide such as (Ib.36) can be synthesized according to the scheme 10. Accordingly, hydroxyacid 48 was lactonized under mild conditions to obtain the lactone 49. Treatment of the lactone with various amines such as pyrrolidine resulted in the intermediate alcohol-amide 50. Oxidation of 50 under Swern conditions to 51 followed by ketalization under standard condition described earlier gave (Ib.36)

Scheme 10

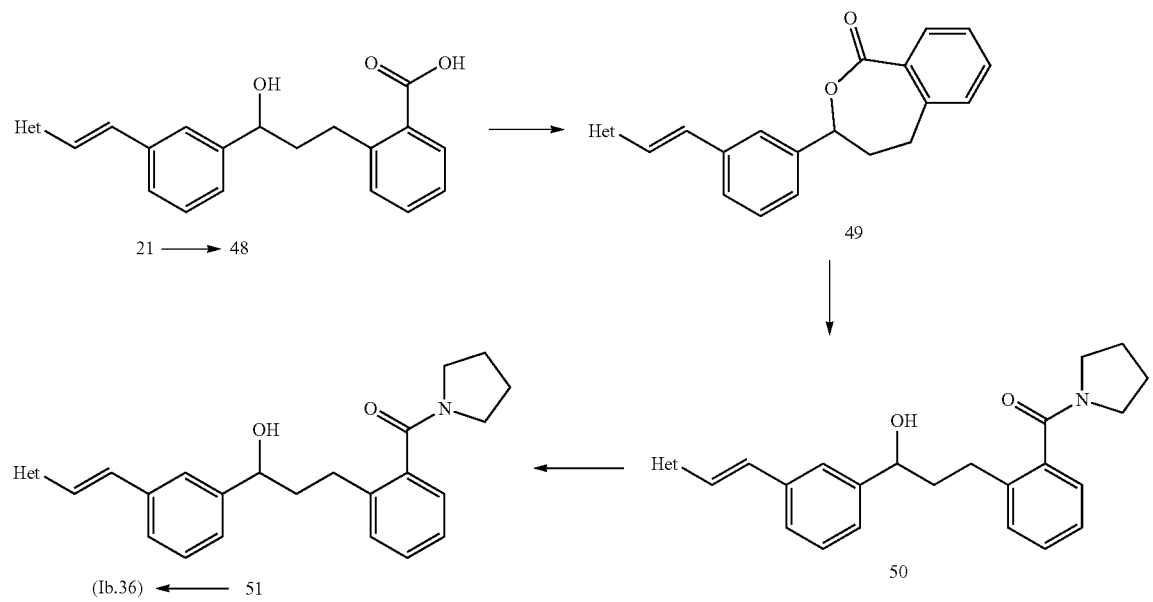

Scheme 11

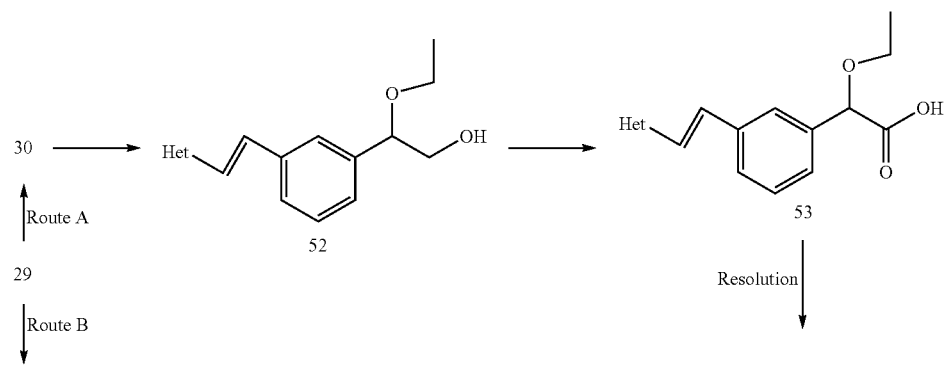

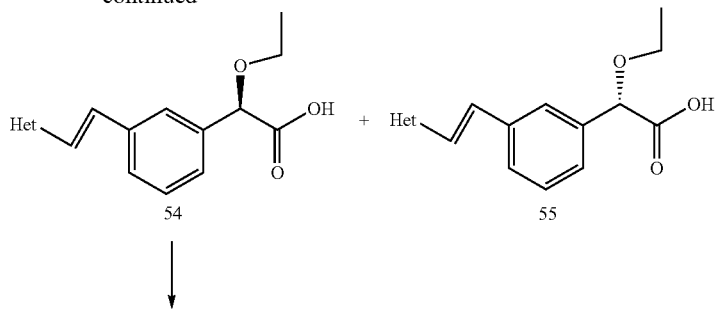

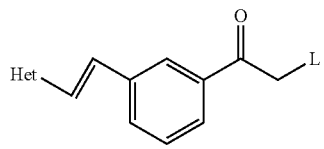

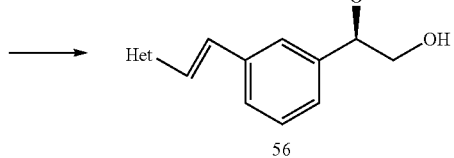

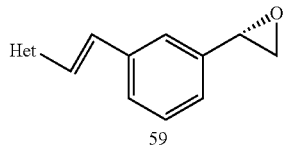

Chiral derivatives present in the invention can be synthesized according to following methods involving chiral resolution processes or asymmetric synthesis of the chiral alcohols required as described in Scheme 11. In route A, a representative oxidation reaction of the alcohol 52 gives the substituted mandelic acid such as 53 as a racemic mixture of enantiomers which on chemical resolution gives the separation of (+) and (−) isomers in one or few crystallization processes. Reduction of the acid gives back the chiral alcohol 54 which on Mitsunobu reaction and hydrolysis gives the compound such as (Ia.166) as a chiral derivative. In route B, the aldehyde 29 (JOC, 1989, 54, 3718-3721) is converted to methyl ketone 57 under Swern oxidative conditions and then brominated with NBS to give the keto-bromide 58. Chiral reduction of the keto-bromo compound 58 under (+) DIP chloride/CBS catalyst followed by base treatment resulted the chiral epoxide 59. Above described ring-opening of epoxide under acidic/Lewis acidic conditions in ethanol 59 resulted in the chiral alcohol 56 with the inverse configuration. Resolutions may be best carried out at an intermediate stage as shown here or occasionally in the final compounds. Alternatively many of the final derivatives can be prepared as racemic mixture of acids from racemic epoxides and separation of the isomers can be done on the final product by chiral column chromatography.

In yet another embodiment as described in Scheme 12 extended compounds of the present invention (Formula-I) can be synthesized, where —Z— is a radical represented by —C=C— (either cis or trans and preferably trans one) or —O—CH2- groups

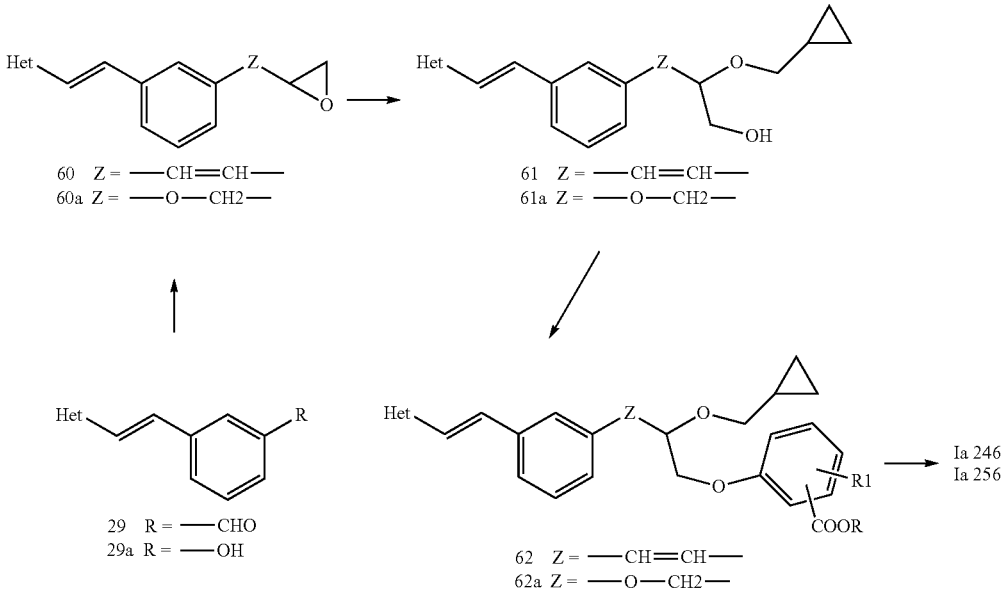

Accordingly, the known aldehyde 29 was treated with acetone under alkaline conditions and the condensation product, further on bromination with NBS, followed by reduction with sodium borohydride and successive treatment with alkali afforded the epoxide intermediate 60. Usual opening of the epoxide under lewis acidic condition (BF3-etherate) with alcohol such as cyclopropyl methanol resulted in an ether-alcohol 61. Further treatment of alcohol with various substituted phenols under Mitsunobu reaction described earlier and subsequent hydrolysis result in some of the compounds described such as Ia-246 and Ia-247 on chiral separation of racemic mixture.

In another extension of the strategy known phenol 29a was treated with epichlorohydrin to covert to the required intermediate epoxide 60a which on acidic ring opening gave the ether-alcohol intermediate 61a. Further chemical transformation as according to the current strategy resulted into the compounds Ia-256 and Ia-257. This invention does not confine to the examples mentioned herein but to prepare such class of compounds as LTD4 antagonists.

EXPERIMENTAL

Most of the compounds presented herein were analytically characterized by $^1$H-NMR, Mass spectroscopic techniques. The term 'usual workup' in the experimental section refers to taking the organic matter into a water immiscible solvent and washing the organic phase with water, brine followed by drying with sodium sulphate and concentrating before subjecting to Flash Chromatography (FC).

General Procedures for Amides in Formula Ia:

Method A:

To a solution of amine (1.0 g) in dichloromethane (20 ml), add triethylamine (1.5 equiv.) followed by acid chloride reagent from FIG. 1. Stir at room temperature, add water and extract in to dichloromethane, wash with water, brine and dry over sodium sulfate (Usual work up) and subject to FC to obtain the product of Formula 1a.

Method B:

To a solution of amine (1.0 g) in dichloromethane (20 ml), an anhydride from FIG. 1. Stir at room temperature, add water and extract in to dichloromethane, wash with water, brine and dry over sodium sulfate and subject to FC to obtain the product of Formula 1a.

Method C:

To a solution of amine (1 g) in a solvent (20 ml), add a solution of mixed-anhydride, prepared by taking the acid (1.1 equiv.), pivolyl chloride (1.1 equiv.) and triethyl amine (1.2 equiv.) also in same solvent (10 ml). Stir at room temperature, add water and extract in to dichloromethane, wash with water, brine and dry over sodium sulfate and subject to FC to obtain the product of product of Formula 1a.

Example 1

2-(3-{3-[(E)-2-(7-chloro-quinalin-2-yl)-vinyl-phenyl}-3-hydroxy-propyl)-benzoic acid methyl ester 21: To a solution of keto-ester 20 (10 g, 21.9 mmol) in (1:2) mixture of methanol:dichlormethane (150 ml) was added sodium borohydride (626 mg, 16.5 mmol) under nitrogen. The reaction mixture was stirred at ambient condition for 1 hour. Water (50 mL) was added to the above mixture and stirred further for 20 minutes. To the resulting mixture dichloromethane (100 ml) was added, the organic phase was separated followed by usual workup, concentration and FC to give off white racemic solid 21 (8.0 g, 80%).

Example 2

2-(3-Acetyl amino-3-{3-[(E)-2-(7-chloro-quinolin-2-yl)-vinyl-phenyl}-propyl)-benzoic acid methyl ester 22: To a stirred solution of 21 (1.0 g, 2.18 mmol) in glacial acetic acid (5 ml) was added acetonitrile (20 ml), a solution of con. sulfuric acid (0.58 mL) in glacial acetic acid (5 ml) at 0° C. and stirred for 10 minutes. The reaction mixture was warmed to room temperature and kept for 24 hours. The reaction mixture was poured in to water (100 ml), basified to pH 12 with aq. NaOH and extracted into ethyl acetate, followed by usual workup, concentration and FC to give compound 22 (0.7 g, 64%) as an off-white solid.

Example 3

2-(3-Acetyl amino-3-{3-[(E)-2-(7-chloro-quinolin-2-yl)-vinyl-phenyl}-propyl)-benzoic acid methyl ester 22a: Prepared according to the procedure described for compound 22 using chloroacetonitrile in place of acetonitrile, yield 22a (51%)

Example 4

2-(3-Amino-3-{3-[(E)-2-(7-chloro-quinolin-2-yl)-vinyl-phenyl}-propyl)-benzoic acid 23: A stirred solution of ester-acetamide 22 (100 mg, 0.2 mmol) in 1,4-dioxane (10 mL) was treated with 4M aq. hydrochloric acid (10 ml) at reflux temperature (110° C.) overnight. The resulting mixture was poured into water (100 ml), basified with aq. NaOH to pH 8.0-10.0, neutralized with aq. acetic acid and filtered. The residue obtained was dried to give amino-acid 23 (30 mg, 34%) as a white solid.

Example 5

(Method B): 2-(3-(3-Carboxy-propionylamino)-3-{3-[(E)-2-(7-chloro-quinolin-2-yl)-vinyl]-phenyl}-propyl)-benzoic acid (Ia.04): To a stirred solution of amino-acid 23 (0.5 g, 1.13 mmol) in dichloromethane was added succinic anhydride (0.34 g, 3.39 mmol) under nitrogen. The reaction mixture was stirred for 1.5 hours at room temperature and filtered to get the solid residue. The residue was washed with to dichloromethane (2×5 ml), followed by washing with n-hexane (2×10 ml) and dried under suction to afford the diacid product (Ia. 04) (0.2 g, 31%) as an off white solid.

Example 6

(Method C): 2-(3-{3-[(E)-2-(7-Chloroquinolin-2-yl)-vinyl]-phenyl}-3-hexanoylamino-propyl)-benzoic acid (Ia.09): To a stirred solution of caproic acid (262 mg, 2.26 mmol) in dichloromethane (10 ml) was added triethylamine (0.62 ml, 4.52 mmol) and pivolyl chloride (0.3 ml, 2.48 mmol) under nitrogen. The resulting mixture was stirred for 15 minutes, amino acid 23 (500 mg, 1.13 mmol) as a solution in dichloromethane (10 ml) was added and stirred for 24 hours. The reaction mixture was quenched with water (50 ml) and acidified to pH 6 using acetic acid. The resulting mixture was extracted with dichloromethane followed by usual workup and FC to give Ia.09 (150 mg, 25%) as an off-white solid.

Example 7

2-[3-{3-[(E)-2-(7-Chloro-quinolin-2-yl)-vinyl]-phenyl}-3-(2-morpholin-4-yl-acetyl amino)-propyl)-benzoic acid (Ia.16)

Step 1:

2-[3-{3-[(E)-2-(7-Chloro-quinolin-2-yl)-vinyl]-phenyl}-3-(2-morpholin-4-yl-acetyl amino)-propyl)-benzoic acid methyl ester: To a stirred solution of chloro-ester 22a (1.0 g, 0.0019 moles) in THF (25 ml) was added morpholin (0.38 ml, 0.0028 moles), tetra butyl ammonium iodide (25 mg) and stirred overnight. The resulting mixture was concentrated and subjected to FC to give morpholino-ester (0.8 g, 73.39%) as colorless oil.

Step 2:

To a stirred solution of morpholino-ester (0.8 g, 0.0014 moles) in dioxane (30 mL) was added 10% aq. NaOH (5.5 ml, 0.014 moles). The reaction mixture was heated at 100° C. for 3 hours, cooled to ambient condition followed by addition of acetic acid (10 ml). The solvents were evaporated followed by addition of ethyl acetate (100 ml) and water (35 ml). The organic layer was separated followed by usual work up. The solvent was evaporated completely to get the residue which was titurated with diethyl ether and filtered to give the acid (Ia.16) (0.388 g, 49.74%) as solid.

Example 8

Ethyl-2-(3-Amino-3-{3-[(E)-2-(7-chloro-quinolin-2yl)-vinyl)-phenyl}-propyl benzoate 24: To a stirred solution of amino-acid 23 (4.0 g, 9.0 mmol) in absolute ethanol (40 ml), conc. sulfuric acid (2.0 ml) was added drop-wise. The mixture was refluxed for 3 hours and concentrated under vacuum. The residual oil obtained was dissolved in dichloromethane (100 ml), washed with aq. sodium carbonate (pH=8.0), water and brine, dried over sodium sulphate and concentrated to obtain amino-ester 24 (5.0 g, 94%) as a yellow oil.

Example 9

(Method A): 2-[3-{3-[(E)-2-(7-chloro-quinolin-2-yl)-vinyl-phenyl}-3-(cyclohexanecarbonyl-amino)-propyl]-benzoic acid (Ia.23): To a stirred solution of amino-ester 24 (1.0 g, 2.19 mmol) in dichloromethane (25 ml) was added cyclohexane carbonylchloride (0.35 ml, 2.63 mmol). The reaction mixture was stirred for 1 hour at room temperature, diluted with dichloromethane (100 ml), washed with 10% aq. sodiumcarbonate solution (pH=8 to 9) and water, dried, evaporated to get the residue. The residue was titurated with diethylether (20 ml) to give crude amide ester (600 mg, 48%), which on usual alkaline hydrolysis gave (Ia.23) (72%) as an off-white solid.

Example 10

2-[2-(3-Azido-3-{3-[(E)-2-(7-chloro-quinolin-2-yl)-phenyl}-propyl)-phenyl]-propan-2-ol 27: To a suspension of diol 25 (7.3 g, 21.8 mmol) in toluene (30 ml) and acetonitrile (70 ml) under nitrogen were added DIEA (5.0 ml, 28.4 mmol) and mesyl chloride (2.0 ml, 26.2 mmol) at −25° C. The reaction mixture was stirred for 3 hours and allowed to cool to −60° C. Hexane (50 ml) was added to the above mixture and stirred for 1 hour. The resulted crude mesylate solid 26 was filtered under nitrogen and transferred to another flask containing DMF (50 ml). Sodium azide (7.0 g, 109 mmol) was added to the flask and the contents were stirred at ambient condition for 12 hours. Water (100 ml) was added to quench the reaction mass. The resulting mixture was extracted with dichloromethane. The organic layer was washed with water (50 ml), dried, concentrated and subjected to FC to give azide 27 (5.0 g, 63%) as a yellow solid.

Example 11

2-[2-3-Amino-3-{3-[(E)-2-(7-chloro-quinolin-2-yl)-phenyl}-propyl)-phenyl]-propan-2-ol 28: To a solution of azido-alcohol 27 (4.0 g, 8.0 mmol) in THF (25 ml) was added TPP (2.317 g, 8.83 mmol) and water (2.0 ml). The reaction mixture was stirred at ambient condition for 36 hours. To the resulting mixture dichloromethane was added. The organic phase was separated, concentrated and subjected to FC to give amino-alcohol 28 (2.5 g, 66%) as a yellow solid.

Example 12

2-Chloro-N-{1-{3-[(E)-2-(7-chloro-quinolin-2-yl)-vinyl]-phenyl}-3-[2-(1-hydroxy-1-methyl-ethyl)-phenyl]-propyl}-acetamide 28a: To a well stirred solution of amino-alcohol 28 (1.0 g, 2.18 mmol) in dichloromethane (25 ml) was added triethylamine (0.365 ml, 2.29 mmol) and chloracetyl chloride (0.182 ml, 2.62 mmol) and stirred for 12-13 hours. To the resulting mixture was added 50% aq. Sodium bicarbonate (100 ml) solution. The aqueous layer was extracted with dichloromethane (2×50 ml) and the combined organic layer was washed with water (2×50 ml), dried, evaporated and crystallized from ether:hexane (50 ml:75 ml) to give 28a (0.850 g, 73%) as an off white solid.

Example 13

4,5-Dichloro-N-{1-{3-[(E)-2-(7-chloro-quinolin-2-yl)-vinyl]-phenyl}-3-[2-(1-hydroxy-1-methyl-ethyl)-phenyl]-propyl}-phthalamic acid (Ia.58): To a stirred solution of amine 28 (0.2 g, 0.00043 mol) in dichloromethane (1.0 ml) at 25-30° C. was added 3,4-dichlorophthalic anhydride (98 mg, 0.00045 mol). The reaction mixture was stirred for 3 hours and filtered. The residue was washed and dried under vacuum to obtain acid (Ia 58) (0.2 g, 69%) as an yellow solid.

Example 14

3-({1-{3-[(E)-2-(7-Chloro-quinolin-2-yl)-vinyl]-phenyl}-3-[2-(1-hydroxy-1-methyl-ethyl)-phenyl]-propylcarbamoyl}-methylsulfanyl)-propionic acid: (Ia.64): To a stirred solution of chloro-amide 28a (0.5 g, 0.93 mmol) in tetrahydrofuran (20 ml) kept under nitrogen was added 2-mercaptoaceticacid (0.130 g, 1.87 mmol) and potassium tert-butoxide (0.210 g, 1.87 mmol). The reaction mass was stirred for 5 hours, poured into water (100 ml) and acidified with glacial acetic acid (10 ml) followed by usual workup in ethylacetate and evaporation to give the residue. The resulted residue was purified by FC followed by trituration with hexane to afford (Ia.64) (0.2 g, 36%) as a pale yellow solid.

Example 15

7-Chloro-2-[(E)-2-(3-oxiranyl-phenyl)-vinyl]-quinoline 30: To a solution of trimethylsulphonium iodide (7.66 g, 37.54 mmol) in dry DMSO (50 ml), under nitrogen was added 50% sodium hydride (1.8 g, 37.54 mmol). The solution was cooled to 10° C. A suspension of 3-[(E)-2-(7-chloro-quinolin-2-yl)-vinyl]-benzaldehyde 29 (10.0 g, 34.12 mmol) in THF (50 ml) was added to the above solution in one portion. The reaction mixture was stirred at ambient conditions for 2 hours and poured into water (1.0 L) followed by usual work in ethyl acetate, and FC to give the epoxide 30 (7.0 g, 66%) as a cream colored solid.

Example 16

2-(1-Hydroxy-1-methyl-ethyl)-phenol 31: To a stirred solution of methyl magnesium chloride (134 ml, 3M in THF) kept under nitrogen, at 0° C. was added a solution of 2-hydroxy acetophenone (50 g, 367 mmol) in anhydrous THF (100 ml). The reaction mixture was stirred. After completion of the reaction, the reaction mixture was treated with 4M acetic acid (500 ml) followed by usual workup in dichloromethane and FC to give hydroxy phenol 31 (25 g, 45%) as a colorless oil.

Example 17

2-[2-(2-{3-[(E)-2-(7-Chloro-quinolin-2-yl)-vinyl]-phenyl}-2-hydroxy-ethoxy)-phenyl]-propan-2-ol 32: To a stirred solution of epoxide 30 (10.0 g, 32.57 mmol) in DMF (30 ml) was added alcohol 31 (7.425 g, 48.85 mmol), potassium carbonate (8.99 g, 65.14 mmol). The reaction mixture was stirred overnight at 120-130° C. The resulted mixture was treated with 10% aq. acetic acid, diluted further with water followed by usual workup in ethyl acetate and FC to give diol 32 (7.0 g, 46%).

Example 18

Methanesulfonic acid 1-{3-[(E)-2-(7-chloro-quinolin-2-yl)-vinyl]-phenyl}-3-[2-(1-hydroxy-1-methyl-ethyl)-phenyl]-propyl ester 33: To a stirred solution of diol 32 (1.0 g, 2.17 mmol) in dry THF (10 ml), at 0° C. was added TEA (0.45 ml, 3.26 mmol) and mesyl chloride (0.18 mL, 2.38 mmol). The reaction mixture was stirred for 2 hours. To the resulting mixture was added saturated solution of sodium bicarbonate (20 ml) and water (50 ml). Above mixture was extracted using dichloromethane. Dichloromethane layer was concentrated to give off-white foam of mesylate 33 (1.0 g, 86%) which was used in the next step without further purification.

Example 19

2-[2-(2-Azido-2-{3-[(E)-2-(7-chloro-quinolin-2-yl)-vinyl]phenyl}-ethoxy)-phenyl]-propan-2-ol 34: To a stirred solution of mesylate 33 (1.0 g, 1.85 mmol) in DMF (10 ml), at ambient condition was added sodium azide (483 mg, 7.43 mmol). The reaction mixture was stirred over night, followed by usual workup in ethyl acetate and FC to give Azide 34 (0.5 g, 55%) as a yellow solid.

Example 20

2-[2-(3-Amino-3-{3-[(E)-2-(7-chloro-quinolin-2-yl)-vinyl]-phenyl}-propyl)-phenyl]-propan-2-ol 35: Following the procedure described for compound 28, amino-alcohol 35 (72% yield) was obtained as a yellow solid in about 24 hours.

Example 21

2-{1-{3-[(E)-2-(7-Chloro-quinolin-2-yl)-vinyl]-phenyl}-2-[2-(1-hydroxy-1-methyl-ethyl)-phenoxy]-ethylcarbamoyl}-cyclopent-1-enecarboxylic acid (Ia.109): To a stirred solution of amine 35 (0.2 g, 0.436 mmol) in dichloromethane (5.0 ml) was added 1-cyclopentene-1,2-dicarboxylicanhydride (0.057 g, 0.436 mmol). The reaction mixture was stirred for 12 hours under mild nitrogen. To the resulting mixture hexane (5 ml) was added, stirred for 15 minutes and filtered. The solid residue obtained was dried under suction to give (Ia. 109) (0.150 g, 58%) as an off white solid.

Example 22

2-(3-tert.-Butoxycarbonyl amino-3-{3-[(E)-2-(7-chloro-quinolin-2-yl)-vinyl]-phenyl}-propyl)-benzoic acid 36: To a stirred solution of amino-acid 23 (6.0 g, 0.0136 moles) in acetonitrile (30 ml) and water (30 ml) at ambient condition, was added TEA (2.26 mL, 0.0163 moles) and (boc)anhydride (3.94 ml, 0.0163 moles). The reaction mixture was stirred for 30 minutes. 1N HCl was added to neutralize the reaction mixture, followed by usual workup in dichloromethane and concentration to give boc-protected 36 (7.0 g, 95.23%) as an off white solid.

Example 23

[1-{3-[(E)-2-(7-chloro-quinolin-2-yl)-vinyl]-phenyl}-3-(2-diethyl-carba moyl-phenyl)-propyl]-carbamic acid tert-butyl ester 37: To a stirred solution of N-Boc-acid 36 (6.0 g, 0.011 mole) in acetonitrile (60 ml) at ambient condition was added triethyl amine (1.85 ml, 0.0133 mol) and pivaloyl chloride (1.5 ml, 0.0122 mole). The reaction mixture was stirred for 30 minutes, treated with diethyl amine (1.37 ml, 0.0133 mol) and further stirred at ambient condition for 3 hour, followed by usual workup in dichloromethane and FC to give the amide 37 (2.4 g, 34.3%) as an off-white solid.

Example 24

2-(3-Amino-3-{3-[(E)-2-(7-chloro-quinolin-2-yl)-vinyl]-phenyl}-propyl)-N,N-diethyl-benzamide 38: Following the De-boc procedure as mentioned below for compound 40, compound 38 was obtained.

Example 25

N-[1-{3-[(E)-2-(7-Chloro-quinolin-2-yl)-vinyl]-phenyl}-3-(2-diethyl-carbamoyl-phenyl)-propyl]-phthalamic acid: (Ia.38): To a stirred solution of amine-amide 38 (300 mg, 0.00059 mol) in dichloromethane (3 ml) was added phthalic anhydride (96.5 mg, 0.00065 mol). The reaction mixture was stirred at room temperature for 1 hour, concentrated and subjected to FC. Product rich fractions were concentrated and recrystallized using toluene to give acid-amide (Ia.38) (120 mg, 10 to 31.5%) as an off-white solid.

Example 26

N-[1-{3-[(E)-2-(7-Chloro-quinolin-2-yl)-vinyl]-phenyl}-3-(2-diethyl-carbamoyl-phenyl)-propyl]-phthalamic acid methyl ester: (Ia.48): To a stirred solution of methyl-hydrogen phthalate (150 mg, 0.00083 mol) in acetonitrile (1.5 ml) was added triethyl amine (0.14 ml) and pivaloyl chloride (0.12 ml). The resulting mixture was stirred for 30 minutes at room temperature. A solution of amine-amide 38 (450 mg, 0.00085 mol) in dichloromethane (1.5 ml) was added to the above solution and the resulting mixture was stirred for 1 hour followed by complete distillation of the solvent and FC. The residue obtained after FC was triturated with diethyl ether, stirred for 0.5 hours and filtered to give di-amide (Ia.48) (140 mg, 25.6%) as an off-white solid.

Example 27

[1-{3-[(E)-2-(7-Chloro-quinolin-2-yl)-vinyl]-phenyl}-3-(2-diethyl carbamoyl-phenyl)-propyl]-methyl-carbamic acid tert. butyl ester 39: To a stirred solution of N-Boc amide 37 (2.4 g, 0.0038 mol) in a mixture of THF (24 ml) and DMF (2 ml) was added NaH (760 mg, 0.019 mol). The resulting mixture was heated at 60° C. for 30 minutes. To the above mixture was added methyl iodide (1.89 ml, 0.030 mol) and stirred for 2-3 hours. The reaction mass was neutralized with acetic acid and diluted with water, followed by usual work up with dichloromethane and FC to give methylated compound 39 (500 mg, 20.4%).

Example 28

2-(3-{3-[(E)-2-(7-Chloro-quinolin-2yl)-vinyl]-phenyl}-3-methyl amino-propyl)-N,N-diethyl benzamide 40: To a stirred solution of N-boc amide 39 (400 mg, 0.62 mmol) in dichloromethane was added conc. $H_2SO_4$ (1.0 ml) drop wise. The reaction mixture was stirred at ambient condition for about 1 hour. The resulting mixture was neutralized with triethyl amine and diluted with water followed by usual work up using dichloromethane and FC to give amine amide 40 (330 mg, 97.6%).

Example 29

N-[1-{3-[(E(-2-(7-Chloro-quinolin-2-yl)-vinyl]-phenyl}-3-(2-diethyl carbamoyl-phenyl)-propyl]-N-methyl-phthaliamic acid (Ia.75): Method B was followed using compound 40 (300 mg). At the end of the reaction diethyl ether was added to the reaction mass followed by filtration to give solid (Ia.75) (300 mg, 69.44%).

Example 30

Methyl-2-[2-(2-{3-[(E)-2-(7-chloro-quinolin-2-yl)-vinyl]-phenyl}-[1,3]dioxolan-2yl)-ethyl]-benzoate 41: To a stirred solution of anhydrous PTSA (333 mg, 1.75 mmol) in dry toluene (50 ml) was added Keto-ester 20 (1.0 g, 2.2 mmol), ethylene glycol (0.732 ml, 13.15 mmol) and additional dry toluene (25 ml). The reaction mixture was refluxed and water-toluene was removed with a Dean-Stark apparatus. After 10 hours, the reaction mixture was poured in to 5% aq. sodium bicarbonate (18.5 ml, 8.77 mmol). The resulted mixture was extracted twice with toluene and the combined organic phase was worked up usually and subjected to FC to give the Ketal-ester 41 (0.7 g, 70%) as an off-white solid. General Procedure of Ester Hydrolysis is as Described in the Following Example.

Example 31

2-[2-(2-{3-[(E)-2-(7-Chloro-quinolin-2yl)-vinyl]phenyl}-[1,3]dioxolan-2yl)-ethyl]-benzoic acid (Ib. 4): To a stirred solution of Ketal ester 41 (0.5 g, 1.0 mmol) in 1,4-dioxane (5.0 ml) was added 20% aq. NaOH (0.4 g, 10.0 mmol). The reaction mixture was refluxed at 100° C. for 12 hours, concentrated to remove dioxane, diluted with water (25 ml) and acidify with 4M acetic acid (3.75 ml, 15 mmol). The resulted precipitates were filtered, washed with water and dried to give pale yellow ketal-acid (Ib. 4) (0.3 g, 61%).

Example 32

Methyl-2-(3-{3-[(E)-2-(7-chloro-quinolin-2-yl)-vinyl]-phenyl}-3,3-diethoxy-propyl)-benzoate 42: To a stirred solution of Keto-ester 20 (1.0 g, 0.0022 mmol) in ethanol (10.0 ml) was added triethyl orthoformate (5.0 ml) and PTSA (0.42 g, 0.002 mmol) at ambient condition. The reaction mixture was refluxed for 4 hours. The resulting mixture was poured into 2% aq. sodium bicarbonate and extracted into dichloromethane (25 ml), followed by usual workup and FC to give Ketal-ester 42 (0.65 g, 56%) as an off-white solid.

Example 33

2-(3-{3-[(E)-2-(7-Chloro-quinolin-2-yl)-vinyl]-phenyl}-3,3-diethoxy-propyl)-benzoic acid (Ib.96): To a stirred solution of Ketal-ester 42 (0.65 g, 1.29 mmol) in 1,4-dioxane (10.0 ml) was added a solution of Sodium hydroxide (0.6 g, 15 mmol). The reaction mixture was heated at 80° C. for 18 hours. The resulting mixture was concentrated to remove dioxane, diluted with water (25 ml) and acidify with acetic acid, followed by usual workup with dichloromethane and FC to give (Ib.96) (0.35 g, 55%).

Example 34

Methyl-2-(3-{3-[(E)-2-(7-chloro-quinolin-2-yl-)-vinyl]-phenyl}-3-hydroxyimino-propyl)-benzoate 43: To a stirred solution of hydroxylamine.hydrochloride (3.05 g, 0.044 mol) in water (40 ml) was added sodium acetate (7.21 g, 0.088 mol) and stirred for 5 minutes. To the above aqueous solution was added Keto-ester 20 (10 g, 0.022 mol), ethanol (200 ml) and heated to 75-80° C. for 5 hours. The reaction mixture was cooled to room temperature and filtered. The solid separated by filtration was dried under vacuum to obtain the oxime-ester 43 (8.5 g) as an off-white solid.

Example 35

2-(3-{3-[(E)-2-(7-chloro-quinolin-2-yl-)-vinyl]-phenyl}-3-hydroxy-imino-propyl)-benzic acid (Ib.145): To a stirred suspension of the oxime-ester 43 (1.45 g, 003 mol) in DMF (30 ml) was added sodium hydride (0.222 g, 0.009 mol) at room temperature followed by ethyl bromide (0.46 ml, 0.006). The reaction mixture was stirred for 2 hours. The resulting mixture was poured into water, stirred for 15 minutes and extracted into ethyl acetate, followed by usual workup and FC. The eluent obtained after FC was concentrated to dryness to obtain the acid-oxime ether (Ib.145) (0.28 g, 18.8%).

Example 36

2-{3-[(E)-2-(7-chloro-quinolin-2-yl)-vinyl]-phenyl}-2-cyclopropyl methoxy-ethanol 44: To a solution of epoxide 30 (3.0 g, 0.0098 mol) in dichloromethane (30.0 ml) was added cyclopropyl methanol (60.0 ml) at ambient condition and stirred for 5 minutes. To the above solution was added boron trifluoride-ethyl ether complex (3.0 ml, 0.0238 mol) slowly at such a rate so as to maintain the temperature of reaction between 25° C. to 30° C. The reaction was stirred at ambient temperature for 18 hours. A saturated aqueous solution of sodium carbonate (3.0 g) was added carefully and the resulting mixture was extracted with dichloromethane (30 ml). The organic phase was separated followed by usual workup and FC to give ether-alcohol 44 (1.5 g, 40.5%).

Example 37

2-(2-{3-[(E)-2-(7-Chloro-quinolin-2-yl)-vinyl]-phenyl}-2-cyclopropyl-methoxy-ethoxy)-benzoic acid methyl ester 45: To a suspension of ether-alcohol 44 (0.9 g, 0.0024 mol) in THF (5 ml) was added triphenyl phosphene (0.93 g, 0.0035 mol) and methyl salicylate (0.54 ml, 0.0036 mol). The resulting mixture was stirred at ambient temperature for 5 minutes and diisopropyl azodicarboxilate (0.71 g, 0.0035 mol) was added drop wise to the mixture. The reaction mixture was stirred at the same temperature for seven days. Dichloromethane (30 ml) was added to the mixture followed by drying of the resulted solution over sodium sulfate, evaporation of the solvents and FC to give ester 45 (0.12 g, 9.62%).

Example 38

2-(2-{3-[(E)-2-(7-Chloro-quinolin-2-yl)-vinyl]-phenyl}-2-cyclopropyl-methoxy-ethoxy)-benzoic acid (Ia.96): A stirred solution of ester 45 (1.0 g, 0.0019 mol) in THF (10.0 ml) was treated with a 20% aqueous solution of tetra-n-butylammonium hydroxide (2.5 ml), at ambient temperature for 15 hours. The solvents were evaporated, the resulting mixture was diluted with aqueous acetic acid and extracted with dichloromethane (30 ml) followed by usual workup and FC to give (Ia.96) (0.8 g, 79%).

Example 39

Methyl-2-(2-{3-[(E)-2-(7-chloro-quinolin-2-yl)-vinyl]-phenyl}-2-hydroxy-ethylsulfanyl)-benzoate 46: To a stirred solution of epoxide 30 (37 g, 0.120 mol) in a mixture of dimethylformamide (140 ml) and acetonitrile (200 ml) was added methyl-2-mercaptobenzoate (20.0 g, 0.145 mol), followed by addition of anhydrous potassium carbonate (19.8 g, 0.145 mol). The reaction mixture was stirred overnight, filtered and concentrated. The resulting mixture was poured into water (2.0 L), stirred and extracted with ethylacetate (1.0 L). The organic layer was washed with water (500 ml) and brine (500 ml), dried over anhydrous sodium sulphate, evaporated and subjected to FC (EtOAc/hexanes) to afford product as a pale yellow solid 46 (18.0 g, 31% yield).

Example 40

Methyl-2-(2-{3-[(E)-2-(7-chloro-quinolin-2-yl)-vinyl]-phenyl}-2-oxo-ethylsulfanyl)-benzoate 47: To a stirred solution of hydroxy compound 46 (10.0 g, 0.021 mol) in dichloromethane (100 ml) was added in single lot pyridinium chlorochromate (13.44 g, 0.035 mol) and allowed to stir at ambient temperature for 2 hours. The resulting mixture was filtered through a bed of highflow. The residue was washed with dichloromethane (500 ml). The combined filtrate layer was evaporated and subjected to FC to give pale yellow solid 47 (8.0 g, 80%).

Example 41

2-(2-Acetoxy-2-{3-[(E)-2-(7-chloro-quinolin-2-yl)-vinyl]-phenyl}-ethylsulfanyl)-benzoic acid (Ia.118)

Step 1:
Compound 46 (1.0 g) was hydrolyzed according to the process given in example 25 in dioxane:water using alkali to obtain alcohol-acid (0.9 g)
Step 2:
To a stirred solution of above alcohol-acid (0.9 g, 0.002 mol) in tetrahydrofuran (2.0 ml) was added pyridine (1 ml), acetic anhydride (2.0 ml) and stirring was continued for 12 hours at room temperature followed by evaporation of the solvents, FC and crystallization of the product obtained after FC in diethyl ether (25 ml) and hexane (50 ml) to give the acyl-acid (Ia.118) (0.58 g, 58.76%) as a yellow solid.

Example 42

2-(2-{3-[(E)-2-(7-Chloro-quinolin-2-yl)-vinyl]-phenyl}-[1,3]dioxolan-2-yl-methylsulfanyl)-benzoic acid (Ib.41): Prepared by following the procedure as described in example 30.

Example 43

2-(3-{3-[(E)-2-(7-Chloro-quinolin-2-yl)-vinyl]-phenyl}-3-hydroxy-propyl)-benzoic acid 48: To a stirred solution of 21 (30.0 g, 65.6 mmol) in 1,4-dioxan (160 ml) was added sodium hydroxide flakes (7.87 g, 196 mmol) and water (70 ml). The reaction mixture was heated to reflux and concentrated in vacuo. Water (1 L) was added to the remaining mixture followed by acidification with glacial acetic acid to pH 6.0 and stirred for 15 minutes. The resulting mixture was filtered and the solid residue obtained was dissolved in ethylacetate (400 ml). The resulting solution was dried over anhydrous sodium sulphate, concentrated to dryness. Hexane (400 ml) was added to the residue and the resulting suspension was filtered to separate the solid which was dried in vacuo to give 48 (24.0 g, 82%) as a pale yellow solid.

Example 44

3-{3-[(E)-2-(7-Chloro-quinolin-2-yl)-vinyl]-phenyl}-4,5-dihydro-3H-benzo[c]-oxepin-1-one 49: To a stirred solution of hydroxy-acid 48 (24.0 g, 54.06 mmol) in dichloromethane (500 ml) was added 4-dimethylamino pyridine (13.23 g, 108 mmol) and stirred for 15 minutes. To the above mixture dicyclohexylcarbodiimide (14.53 g, 70.2 mmol) was added and stirred for 24 hours. The precipitated DCU was filtered off and the filtrate was concentrated. The residue obtained after concentration was suspended in THF (150 ml) and filtered to remove any residual DCU followed by washing the residue with additional THF (2×50 ml). The combined filtrate was concentrated in vacuo and subjected to FC. The residue obtained after concentration of the eluent was triturated with hexane (200 ml) and filtered to give solid lactone 49 (20.0 g, 80%).

Example 45

[2-(3-{3-[(E)-2-(7-Chloro-quinolin-2-yl)-vinyl]-phenyl}-3-hydroxy-propyl)-phenyl]-pyrrolidin-1-yl-methanone 50: A stirred solution of lactone 49 (21.0 g, 49.0 mmol) in pyrrolidine (20 ml, 241 mmol) was heated at 90° C. for 3 hours. Excess pyrrolidine was distilled off and the residue was dissolved in dichloromethane (200 ml) followed by FC to give desired hydroxy pyrrolidinamide 50 (15.0 g, 61%) as a pale yellow solid.

Example 46

1-{3-[(E)-2-(7-chloro-quinolin-2-yl)-vinyl]-phenyl}-3-[2-(pyrrolidine-1-carbanyl)-phenyl]-propan-1-one 51: To a stirred solution of oxalylchloride (2.47 ml, 28.7 mmol) in dichloromethane (33.74 ml) was added a solution of dimethyl sulfoxide (4.4 ml, 62.6 mmol) in dichloromethane (14.2 ml) during 5 minutes period At −60° C. The resulting mixture was stirred for 30 minutes and a solution of hydroxy pyrrolidinamide 50 (13.0 g, 26.1 mmol) in dichloromethane (40 ml) was added drop-wise. The reaction mixture was stirred for 40 minutes and di-isopropylethylamine (22.3 ml, 130 mmol) was added dropwise and further stirred for additional 45 minutes. The reaction was allowed to warm to ambient temperature and stirred for 1 hour. Water (200 ml) was added to the above mixture and followed by extraction using dichloromethane (2×200 ml), usual workup and FC. Evaporation of the eluent gave keto-amide 51 (7.0 g, 54%) as an off-white solid.

Example 47

{2-[2-(2-{3-[(E)-2-(7-Chloro-quinolin-2-yl)-vinyl]-phenyl}-[1,3]-dioxolan-2-yl)-ethyl]-phenyl}-pyrrolidin-1-yl-methanone (Ib.36): Prepared according to the procedure as described in example 30.

Example 48

2-{3-[(E)-2-(7-Chloro-quinolin-2-yl)-vinyl]-phenyl}-2-ethoxy-ethanol 52: Prepared as described in example 36 using ethanol, 30 and in presence of Lewis acid $BF_3$-etherate.

Example 49

{3-[(E)-2-(7-Chloro-quinolin-2-yl)-vinyl]-phenyl}-ethoxy-acetic acid 53: To a stirred solution of ethoxy-alcohol 52 (30 g, 0.085 mol) in dichloromethane (300 ml) was added catalytic TEMPO (0.265 g, 0.0017 mol) and stirred for 10 minutes. To the above solution 100 ml aqueous solution containing mixture of sodium chlorite (23 g, 0.25 mol) and potassium bromide (5 g, 0.0425 mol) was added and stirred for 5 minutes. To this reaction mixture was added aq. acetic acid (5 ml, 20%) and stirring was continued for 12 hour at ambient temperature. The reaction mixture was filtered and the solid was washed with D.M. Water (500 ml) followed by washing with dichloromethane (200 ml). Toluene (400 ml) was added to the solid obtained and the resulting mixture was concentrated azeotropically till the volume of mixture remains to 150 ml and cooled in ice bath. The resulting suspension was filtered. The solid obtained was washed with hexane and dried in vacuum to yield ethoxy-acid 53 (25 g, 80.6%).

Example 50

(R)-{3-[(E)-2-(7-Chloro-quinolin-2-yl)-vinyl]-phenyl}-ethoxy-acetic acid 54. To a stirred suspension of racemic ethoxy-acid 53 (100 g, 0.27 mol) in acetone:water mixture (9:1, 900 ml) was added a solution of R-(+)-alpha methylbenzylamine (35 ml, 0.27 mol) acetone:water (9:1, 100 ml) in a dropwise manner. The resulting mixture was stirred for 16-17 hours, filtered to separate the solid and neutralise with acetic acid. The process was repeated several times to get (−)-ethoxy acid 54 (18 g, 98-99% e.e by HPLC).

Example 51

(S)-{3-[(E)-2-(7-Chloro-quinolin-2-yl)-vinyl]-phenyl}-ethoxy-acetic acid 55: Use S-(−)-alphamethyl benzylamine in the above procedure to obtain (+)-ethoxy acid 55.

Example 52

(R)-2-{3-[(E)-2-(7-Chloro-quinolin-2-yl)-vinyl]-phenyl}-2-ethoxy-ethanol 56

Step 1:
To a suspension of ethoxy acid 54 (5.3 g, 0.01 mol) in methanol (100 ml) cooled to 5-10° C., was added thionyl chloride (8.0 ml, 0.13 mol) in drop wise manner. The reaction mixture was refluxed for 2 hours and cooled to ambient temperature. The solvent was evaporated completely and to the residue was added dichloromethane (150 ml) and saturated aqueous sodium bicarbonate solution (150 ml). The resulting mixture was stirred for 15 minutes and the organic layer was separated which on usual workup and complete evaporation of the solvent gave the ester (6.5 g) as colorless oil, which was used in the next step without purification.
Step 2:
To a stirred solution of above ester (6.5 g, 0.017 moles) in methanol cooled to 5-10° C., was added sodium borohydride (2.5 g, 0.068 mol) portion wise and stirred for 2 hours at ambient temperature. The solvent was evaporated completely and dichloromethane (100 ml) and D.M. Water (100 ml) were added to the residue. The organic phase was separated and washed with 5% aqueous solution of acetic acid followed by usual workup and evaporation of the solvent completely. Toluene (100 ml) was added to the above mixture and subjected to azetropic distillation till the volume of the mixture remains to approx. 25 ml. The concentrated mixture was cooled to ambient temperature, stirred for 2 hours and filtered to isolate the solid chiral alcohol 56 (4.0 g 66.66%).

Example 53

1-{3-[(E)-2-(7-Chloro-quinolin-2-yl)-vinyl]-phenyl}-ethanone 57

Step 1:
A 3M solution of methylmagnesium chloride (12.46 ml, 37.4 mmol) in THF was added dropwise to a well stirred suspension of aldehyde 29 (10 g, 34 mmol) in toluene (80 ml) kept at −10° C. under nitrogen and stirred for 2 hours. To the resulting mixture was added 10% aq. ammonium chloride (52.65 ml) solution in a dropwise manner. The reaction mixture was warmed to room temperature, water (27.5 ml) was added and stirred for 30 minutes. The resulting suspension was filtered, washed with water (2×30 ml) and isopropyl alcohol (10 ml) and dried to give the alcohol (8.2 g, 78%) as an off-white solid.
Step 2:
To a cold (−78° C.) and stirred solution of oxalylchloride (3.08 g, 24.2 mmol) in anhydrous THF (44 ml) was added a solution of dimethylsulfoxide (4.42 g, 56.5 mmol) in THF (6 ml) in drop-wise manner to maintain the temperature in the range −78° C.±5° C. The resulting mixture was stirred for 30 minutes and treated with a suspension of above alcohol (5 g, 16.1 mmol) in a mixture of (1:1) dichloromethane:THF (100 ml). The reaction mixture was stirred reaction for 45 minutes. Triethylamine (9.63 g, 95 mmol) was added dropwise and stirring was continued for 30 minutes. The reaction mixture was warm to 5° C., water (125 ml) was added and stirred for 15 minutes. The resulting mixture was extracted with dichloromethane (100 ml) followed by usual work up and concentration to give ketone 57 (3.0 g, 60% yield) as an off white solid.

Example 54

2-Bromo-1-{3-[(E)-2-(7-chloro-quinolin-2-yl)-vinyl]-phenyl}-ethanone 58. To a warm (90° C.) and stirred solution of ketone 57 (5 g, 0.016 mol) in a mixture of 4:1 toluene and acetonitrile (125 ml) was added methane sulfonic acid (2.64 ml, 0.041 mole) and stirred for 1 hour. The reaction mixture was cooled to 68° C., NBS (3.19 g, 0.018 mol) was added at once and stirred the contents at 65° C. for 4 hour followed by stirring at RT for 18 hour. The solid from the reaction mixture was collected by filtration and dissolved in dichloromethane (100 ml). dichloromethane layer was washed with 10% aq. sodium carbonate and subjected to usual workup and concentration to obtain alpha bromo-ketone 58 (3.0 g, 48%) as an off-white solid.

Example 55

(−) 7-Chloro-2-[(E)-2-((S)-3-oxiranyl-phenyl)-vinyl]-quinoline 59

Step 1:
2-Bromo-1-{3-[(E)-2-(7-chloro-quinolin-2-yl)-vinyl]-phenyl}-ethanol: To a cold (−25° C.) and stirred suspension of bromo-ketone 58 (5 g, 0.013 mol) in anhydrous THF (60 ml) was added diisopropylethylamine (0.83 g, 0.005 mol) followed by addition of (+)DIP chloride (21 ml, 60-65% solution in Hexane) at −25° C. The resulting mixture was stirred at −20° C. for 30 minutes, followed by stirring at −15° C. for 3 hour. The resulted hazy reaction mixture was stirred at 0° C. for 1 hour. Acetone was added to the mixture and stirred at room temperature for 18 hours. Above mixture was again cooled to 0° C. and to it, was added 20% aq. solution potassium-sodium-tartarate (110 ml). The resulted mixture was stirred and extracted into THF. The organic phase was washed with 90% brine and THF was evaporated followed by crystallization of the crude solid in ethylacetate:heptane (1:2), to give bromo-alcohol (3.9 g, 78%) as an off-white to pale-yellow solid.

Step 2:

To a stirred solution of above bromo-alcohol (8 g, 0.021 mol) in 1,4-dioxane 80 ml) was added a solution of aq NaOH (1.65 g, 0.04 mol). The reaction mixture was stirred at room temperature for 2 hours and diluted with toluene (160 ml). The organic phase was washed with D.M. Water and, separated followed by usual workup and concentration to give epoxide 59 (5.1 g, 81%) as an off-white solid.

Example 56

7-Chloro-2-{(E)-2-[3-((E)-2-oxiranyl-vinyl)-phenyl]-vinyl}-quinoline 60

Step 1:

To a solution of aldehyde 29 (15 g, 0.0519 mol) in a mixture of 200 ml of Acetone:THF (1:1) was added 10% aq. NaOH solution and stirred for 3 hours. Dilute acetic acid was added till pH of mixture was acidic. The reaction mixture was evaporated to half volume and poured into water (200 ml). The solid separated out was filtered to yield (E)-4-{3-[(E)-2-(7-Chloro-quinolin-2-yl)-vinyl]-phenyl}-but-3-en-2-one (13 g, 76.47%) as a yellow solid.

Step 2:

To a solution of above enone (3 g, 0.009 mol) in 80 ml Acetonitrile:Toluene (1:1) was added methanesulfonic acid (2.16 g, 0.02252 mol) and NBS (1.67 g, 0.00945 mol) and heated to 85° C. for 3 hours. Sat. NaHCO₃ (100 ml) and ethylacetate (100 ml) were added to the above mixture. The organic layer was separated and subjected to purification by column chromatography to afford bromo-product [(E)-1-Bromo-4-{3-[(E)-2-(7-chloro-quinolin-2-yl)-vinyl]-phenyl}-but-3-en-2-one] (1.2 g, 32.43%) as a yellow solid.

Step 3:

To a solution of above bromo product (6 g, 0.14556 mol) in a mixture of 200 ml of methanol:dichloromethane (1:1) was added sodium borohydride portion wise and stirred for 1 hour at ambient temperature. Water (25 ml) was added to the above mixture and stirred for 15 minutes. The organic layer was separated, washed with D.M. Water, brine and dried over sodium sulphate. The solvent was completely evaporated to give 8.0 g of brown oil [(E)-1-Bromo-4-{3-[(E)-2-(7-chloro-quinolin-2-yl)-vinyl]-phenyl}-but-3-en-2-one] which was used directly in the next step without further purification.

Step 4:

To a solution of the above oil (8.0 g, 0.01932 mol) in 100 ml dioxane was added 2N aq. NaOH (100 ml). The resulting mixture was stirred overnight. The organic layer was separated, washed with D.M. Water (100 ml) and dried over sodium sulphate. The solvent was completely evaporated and the residue obtained was titurated with diethyl ether (25 ml), stirred for 15 minutes and filtered to give title Epoxide-60 (3.8 g, 59.37%) as an off-white solid.

Example 57

(E)-4-{3-[(E)-2-(7-Chloro-quinolin-2-yl)-vinyl]-phenyl}-2-cyclopropyl methoxy-but-3-en-1-ol 61: Prepared according to the process described in Example 30 to afford ether-alcohol 61 (50%) as a yellow solid.

Example 58

2-((E)-4-{3-[(E)-2-(7-Chloro-quinolin-2-yl)-vinyl]-phenyl}-2-cyclo propylmethoxy-but-3-enyloxy)-5-methoxy-benzoic acid methyl ester 62: A solution of ether-alcohol 61 (2 g, 0.0049 mol) in dioxane (20 ml) was prepared, stirred for 15 minutes and added to another solution of ADDP (2.48 g, 0.0099 mol) and Triphenylphosphine (2.58 g, 0.0099 mol) in dioxane (10 ml). The resulting mixture was stirred for 5 minutes. To the above mixture was added 2-hydroxy-5-methoxybenzoic acid methyl ester and stirred overnight. To the resulting mixture D.M. Water (0.1 ml), acetic acid (0.1 ml) were added and stirred for 5 minutes. The solvents were evaporated completely and the residue obtained was titurated with diethyl ether, stirred for 15 minutes and filtered. The filtrate was subjected to FC (hexane:ethyl acetate) to afford ester-62 (1.87 g) as an oil.

Example 59

2-((E)-(S)-4-{3-[(E)-2-(7-Chloro-quinolin-2-yl)-vinyl]-phenyl}-2-cyclo propylmethoxy-but-3-enyloxy)-5-methoxy-benzoic acid Ia246 and its enantiomer Ia247: To a stirred solution of above ester-62 in ethanol (100 ml) was added aq. NaOH (1.22 g in 50 ml) and stirred overnight at ambient temperature. The solvent was evaporated completely from the above mixture. To the residue D.M. Water (100 ml) was added and stirred for 15 minutes followed by addition of dilute acetic acid. The resulting mixture was extracted in Ethyl acetate (100 ml). The organic layer was separated and washed with D.M. Water, brine and dried over sodium sulphate. The solvent was evaporated completely to obtain the racemic acid (1.2 g, 68.6%) as yellow oil which was further separated into chiral isomers Ia246 (190 mg) and Ia247 (120 mg) by chiral chromatography.

Example 60

7-Chloro-2-[(E)-2-(3-oxiranylmethoxy-phenyl)-vinyl]-quinoline 60a: To a solution of phenol 29a (12 g, 0.043 mol) in dioxane (100 ml) was added epichlorohydrin (33 ml, 0.43 mol), D.M. Water (50 ml) and NaOH (2 g, 0.05 mol). The reaction mixture was heated at 80° C. overnight, cooled to ambient temperature and extracted in ethyl acetate. The organic layer was washed with water, brine, dried over sodium sulphate and subjected to column chromatography to afford 60a (8.0 g, 55.70%) as a yellow solid.

Example 61

3-{3-[(E)-2-(7-Chloro-quinolin-2-yl)-vinyl]-phenoxy}-2-cyclopropylmethoxy-propan-1-ol 61a: As described in Example 30 using 60a to afford ether-alcohol 61a (41.2%) as a yellow solid.

Example 62

2-(3-{3-[(E)-2-(7-Chloro-quinolin-2-yl)-vinyl]-phenoxy}-2-cyclopropyl methoxy-propoxy)-5-methoxy-benzoic acid methyl ester 62a: As described in Example 52 using 61a to afford the ester 62a (76%) as a yellow oil.

Example 67

2-((S)-3-{3-[(E)-2-(7-Chloro-quinolin-2-yl)-vinyl]-phenoxy}-2-cyclo propylmethoxy-propoxy)-5-methoxy-benzoic acid Ia256 and enantiomer Ia257

As described in the Example 53 using ester 62a in hydrolysis to racemic mixture of acids (72.4%), which on chiral separation gave Ia256 and Ia257 as a pale yellow solids.

Biological Assay Methods:

The primary in-vitro biological screening for the compounds carried-out involving receptor radio-ligand-binding assay (Tritiated LTD4 as the ligand) by known methods described in literature [a]. Mong et al. European Journal of Pharmacology (102); 1984 1-11b). Jones et al; Journal of Physiology & Pharmacology (73); 1994, 191-201 c). MDS Pharma Services: 250460 Leukotriene, Cysteinyl CysLT1]. Accordingly, Guinea pig lung membrane (100 ug) is incubated with 0.2 nM 3H LTD4 in presence of Reference Standard/Test item/Vehicle Control. Non Specific Binding is determined by incubating the membrane with 0.2 nM 3H LTD4 in presence of 1 uM of unlabeled LTD4. The samples are incubated at 26° C. for 30 minutes and are vacuum filtered on a membrane to separate the bound and free radioligand. The membrane is counted in a liquid scintillation counter to calculate the bound radioactivity. Specific Binding in Vehicle treated and Reference Standard/Test item treated set is compared to evaluate the % Inhibition values. Some of the compounds have shown >50% inhibition in the presence of ≤3 nano-molar concentration of the compounds of present invention as shown in the following table.

| Selected entry | % Inhbition (in nM) | | |
|---|---|---|---|
| | 1 | 3 | 10 |
| Ia.11 | 46 | 56 | 71 |
| Ia.12 | 5 | 35 | 56 |
| Ia.38 | 0.3 | 51 | 69 |
| Ia.48 | 35 | 56 | 65 |
| Ia.54 | 50 | 60 | 74 |
| Ia.69 | 34 | 56 | 72 |
| Ia.73 | 40 | 67 | 72 |
| Ia.76 | 37 | 61 | 67 |
| Ia.80 | 43 | 64 | 65 |
| Ia.118 | 33 | 46 | 52 |
| Ia.127 | 50 | 69 | 73 |
| Ia.143 | 32 | 56 | 74 |
| Ia.157 | 62 | 72 | 80 |
| Ia.172 | 50 | 77 | 88 |
| Ia.185 | 57 | 60 | 84 |
| Ia.192 | 38 | 54 | 74 |
| Ia.199 | 76 | 88 | 97 |
| Ia.205 | 46 | 49 | 70 |
| Ib.4 | 33 | 41 | 62 |
| Ib.11 | 32 | 60 | 74 |
| Ib.26 | 34 | 53 | 56 |
| Ib.36 | 49 | 91 | 99 |
| Ib.42 | 31 | 41 | 49 |
| Ib.59 | 64 | 74 | 97 |
| Ib.67 | 72 | 86 | 89 |
| Ib.79 | 67 | 78 | 86 |
| Ib.86 | 6 | 38 | 53 |
| Ib.93 | 14 | 20 | 60 |
| Ib.101 | 17 | 55 | 74 |
| Ib.111 | 65 | 84 | 91 |
| Ib.113 | 48 | 68 | 85 |
| Ib.123 | 58 | 81 | 86 |
| Ib.133 | 41 | 57 | 80 |

-continued

| Selected entry | % Inhbition (in nM) | | |
|---|---|---|---|
| | 1 | 3 | 10 |
| Ib.135 | 56 | 77 | 86 |
| Ib.139 | 28 | 52 | 82 |
| Ib.142 | 15 | 49 | 80 |
| Ib.148 | 20 | 16 | 31 |

All publications and patent applications cited in this application are herein incorporated by reference to the same extent as if each individual publication or patent application was specifically and individually indicated to be incorporated herein by reference.

We claim:

1. A compound of formula (Ia), or a pharmaceutically acceptable salt thereof,

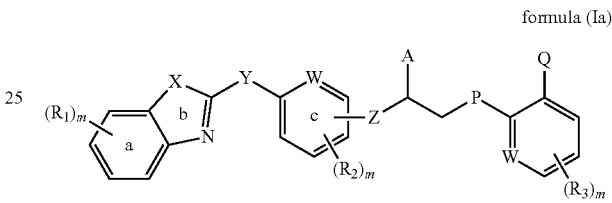

formula (Ia)

wherein at each occurrence $R_1$, $R_2$ and $R_3$ are independently selected from the group consisting of hydrogen, halogen, —OH, —CN, —$NO_2$, —$NH_2$, —$C_{1-10}$ alkyl, —$C_{3-10}$ cycloalkyl, —O—$C_{1-8}$ alkyl, —O—$C_{1-8}$ alkyl (alkoxy), —O—$C_{3-8}$ cycloalkyl (cyclalkoxy), —S—$C_{1-8}$ alkyl (thioalkoxy), —C(O)—$C_{1-8}$ alkyl, —COOH, —C(O)$NH_2$, —C(O)NH—$C_{1-8}$ alkyl, —C(O)N($C_{1-8}$ alkyl)$_2$, —C(O)O—$C_{1-8}$ alkyl, —$C_{1-8}$ haloalkyl (haloalkoxy), —$C_{3-8}$ alkenyl, —$C_{3-8}$ alkynyl, —OC(O)—$NH_2$, —OC(O)—NH($C_{1-8}$ alkyl), —OC(O)—N($C_{1-8}$ alkyl)$_2$, —NH($C_{1-8}$ alkyl), —N($C_{1-8}$ alkyl)$_2$, —NH—$SO_2$—$C_{1-8}$ alkyl, —N($C_{1-8}$ alkyl)-$SO_2$—$C_{1-8}$ alkyl, —NH—C(O)—($C_{1-8}$ alkyl), —N($C_{1-8}$ alkyl)-C(O)—($C_{1-8}$ alkyl), —NH—C(O)O—$C_{1-8}$ alkyl, —N($C_{1-8}$ alkyl)-C(O)O—$C_{1-8}$ alkyl, —NH—C(O)—$NH_2$, —NH—C(O)—NH($C_{1-8}$ alkyl), —N($C_{1-8}$ alkyl)-C(O)—NH($C_{1-8}$ alkyl), —N($C_{1-8}$ alkyl)-C(O)—N($C_{1-8}$ alkyl)$_2$, —NH—C(O)—NH—$SO_2$—$C_{1-8}$ alkyl, —N($C_{1-8}$ alkyl)-C(O)—NH$SO_2$—$C_{1-8}$ alkyl, —N($C_{1-8}$ alkyl)-C(O)—N($C_{1-8}$ alkyl)-$SO_2$—$C_{1-8}$ alkyl, —S—$C_{1-8}$ alkyl, —S(O)—$C_{1-8}$ alkyl, —$SO_2$—$C_{1-8}$ alkyl, —S-aryl, —S(O)-aryl, $SO_2$-aryl, —$SO_2NH_2$, —$SO_2$NH—($C_{1-8}$ alkyl), and —$SO_2$N($C_{1-8}$ alkyl)$_2$;

W represents a group selected from =CH and N;

X represents a group selected from —CH=CH— and —N=CH—, wherein the nitrogen of the —N=CH— is directly bonded to ring 'a';

Y represents a group selected from —CH=CH— and —C≡C—;

Z represents a bond or group selected from —(CH$_2$)$_n$—, —O—CH$_2$—, and —CH=CH—;

A is a group selected from the group consisting of —OR, —O(CH$_2$)$_n$ aryl, —O(CH$_2$)$_n$ heteroaryl, —OCOR, and —OCO-aryl;

P is selected from the group consisting of —O— and —CH$_2$—;

Q is a group selected from the group consisting of
—COOR wherein R is selected from the group consisting of hydrogen, —$C_{1-6}$ alkyl, —$C_{3-6}$ cycloalkyl, —$C_{1-3}$ alkyl (cycloalkyl), —$C_{3-6}$ alkenyl and —$C_{3-6}$ alkynyl;
n at each occurrence is an integer selected from 1, 2, and 3; and
m at each occurrence is an integer selected from 0, 1, 2, 3, and 4.

2. The compound according to claim 1, or the salt thereof, wherein W is CH.

3. The compound according to claim 1, or the salt thereof, wherein X is —CH=CH—.

4. The compound according to claim 1, or the salt thereof, wherein Y is —CH=CH—.

5. The compound according to claim 1, or the salt thereof, wherein Z represents a bond.

6. The compound according to claim 1, or the salt thereof, wherein $R_1$ and $R_2$ are selected from hydrogen and halogen.

7. The compound according to claim 1, or the salt thereof, wherein A is —OR and P is —O—.

8. A compound of formula (Id), or a pharmaceutically acceptable salt or esters thereof formula (Id)

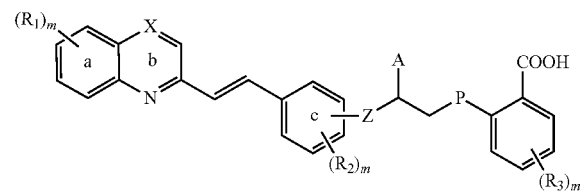

wherein
at each occurrence $R_1$, $R_2$, and $R_3$ are independently selected from the group consisting of hydrogen, halogen, —OH, —CN, —$NO_2$, —$NH_2$, —$C_{1-10}$ alkyl, —$C_{3-10}$ cycloalkyl, —O—$C_{1-8}$ alkyl, —O—$C_{1-8}$ alkyl (alkoxy), —O—$C_{3-8}$ cycloalkyl (cyclalkoxy), —S—$C_{1-8}$ alkyl (thioalkoxy), —C(O)—$C_{1-8}$ alkyl, —COOH, —C(O)$NH_2$, —C(O)NH—$C_{1-8}$ alkyl, —C(O)N($C_{1-8}$ alkyl)$_2$, —C(O)O—$C_{1-8}$ alkyl, —$C_{1-8}$ haloalkyl (haloalkoxy), —$C_{3-8}$ alkenyl, —$C_{3-8}$ alkynyl, —OC(O)—$NH_2$, —OC(O)—NH($C_{1-8}$ alkyl), —OC(O)—N($C_{1-8}$ alkyl)$_2$, —NH($C_{1-8}$ alkyl), —N($C_{1-8}$ alkyl)$_2$, —NH—$SO_2$—$C_{1-8}$ alkyl, —N($C_{1-8}$ alkyl)-$SO_2$—$C_{1-8}$ alkyl, —NH—C(O)—($C_{1-8}$ alkyl), —N($C_{1-8}$ alkyl)-C(O)—($C_{1-8}$ alkyl), —NH—C(O)O—$C_{1-8}$ alkyl, —N($C_{1-8}$ alkyl)-C(O)O—$C_{1-8}$ alkyl, —NH—C(O)—$NH_2$, —NH—C(O)—NH($C_{1-8}$ alkyl), —N($C_{1-8}$ alkyl)-C(O)—NH($C_{1-8}$ alkyl), —N($C_{1-8}$ alkyl)-C(O)—N($C_{1-8}$ alkyl)$_2$, —NH—C(O)—NH—$SO_2$—$C_{1-8}$ alkyl, —N($C_{1-8}$ alkyl)-C(O)—NHSO$_2$—$C_{1-8}$ alkyl, —N($C_{1-8}$ alkyl)-C(O)—N($C_{1-8}$ alkyl)-$SO_2$—$C_{1-8}$ alkyl, —S—$C_{1-8}$ alkyl, —S(O)—$C_{1-8}$ alkyl, —$SO_2$—$C_{1-8}$ alkyl, —S-aryl, —S(O)-aryl, $SO_2$-aryl, —$SO_2NH_2$, —$SO_2$NH—($C_{1-8}$ alkyl), and —$SO_2$N($C_{1-8}$ alkyl)$_2$;
X represents a group selected from CH and N;
Z represents a bond or group selected from —(CH$_2$)$_n$—, —O—CH$_2$—, and —CH=CH—;
A is a group selected from —OR, —O(CH$_2$)$_n$ aryl, —O(CH$_2$)$_n$ heteroaryl, —OCOR, and —OCO-aryl, wherein R is independently selected from the group consisting of —$C_{1-6}$ alkyl, —$C_{3-6}$ cycloalkyl, —$C_{1-3}$ alkyl (cycloalkyl), —$C_{3-6}$ alkenyl, and —$C_{3-6}$ alkynyl,
or R along with the atom to which it is attached together form a substituted or unsubstituted 5 to 8 membered cyclic ring
P is selected from the group consisting of —O— and —CH$_2$—
at each occurrence n is an integer selected from 1, 2, and 3;
at each occurrence m is an integer selected from 0, 1, 2, 3, and 4.

9. The compound according to claim 8, or the salt thereof, selected from the group consisting of:

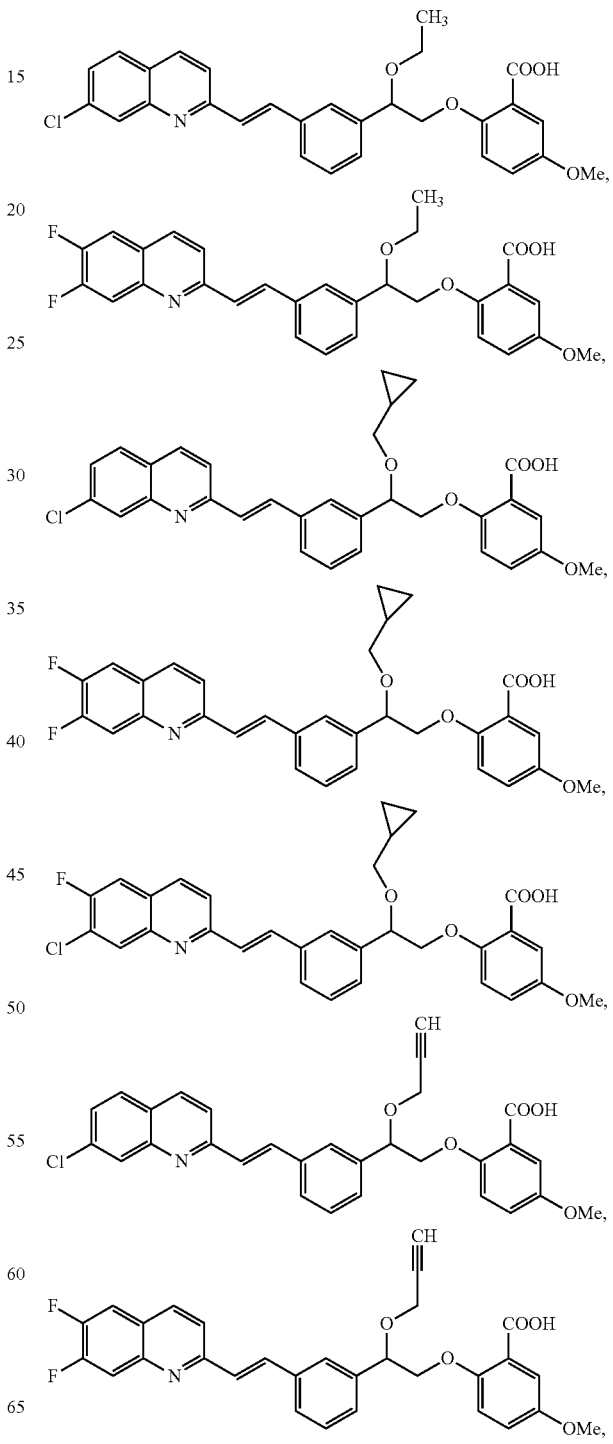

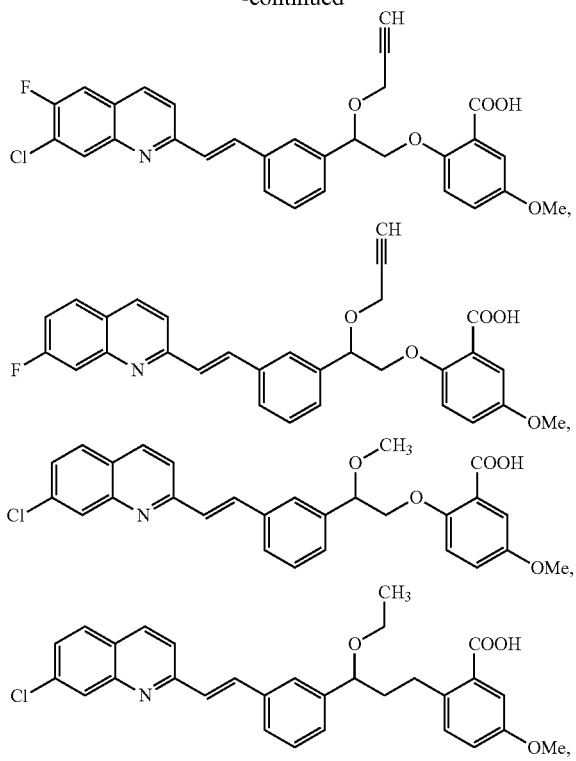
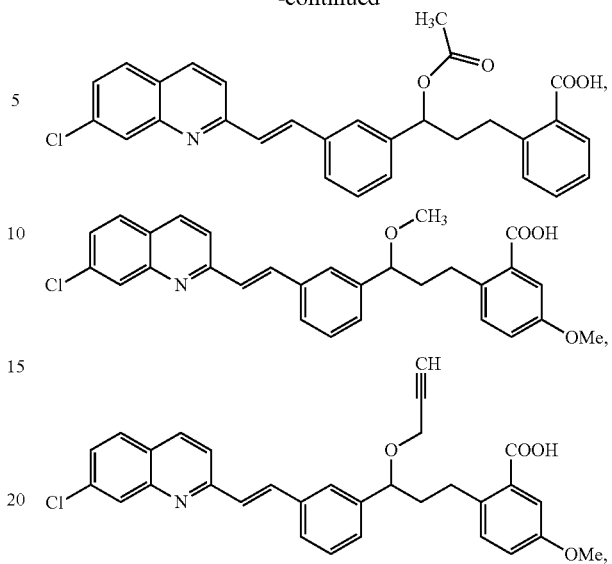
and a pharmaceutically acceptable salt of any one thereof.
* * * * *